US009595681B2

(12) United States Patent
Mujica-Fernaud et al.

(10) Patent No.: US 9,595,681 B2
(45) Date of Patent: *Mar. 14, 2017

(54) COMPOUNDS AND ORGANIC ELECTROLUMINESCENT DEVICES

(71) Applicant: Merck Patent GmbH, Darmstadt (DE)

(72) Inventors: Teresa Mujica-Fernaud, Darmstadt (DE); Elvira Montenegro, Weinheim (DE); Amir Hossain Parham, Frankfurt am Main (DE); Arne Buesing, Frankfurt am Main (DE); Frank Voges, Bad Duerkheim (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/416,749

(22) PCT Filed: Jun. 27, 2013

(86) PCT No.: PCT/EP2013/001891
§ 371 (c)(1),
(2) Date: Jan. 23, 2015

(87) PCT Pub. No.: WO2014/015937
PCT Pub. Date: Jan. 30, 2014

(65) Prior Publication Data
US 2015/0179953 A1  Jun. 25, 2015

(30) Foreign Application Priority Data

Jul. 23, 2012  (EP) ..................... 12005369

(51) Int. Cl.
| *C07C 217/94* | (2006.01) |
|---|---|
| *H01L 51/00* | (2006.01) |
| *C07F 7/08* | (2006.01) |
| *C07D 333/76* | (2006.01) |
| *C07D 307/91* | (2006.01) |
| *C07C 209/10* | (2006.01) |
| *C07D 209/86* | (2006.01) |
| *C07D 219/02* | (2006.01) |
| *C07C 213/02* | (2006.01) |
| *C07D 405/12* | (2006.01) |
| *C07C 211/61* | (2006.01) |
| *C09K 11/06* | (2006.01) |
| *H05B 33/14* | (2006.01) |
| *H01L 51/50* | (2006.01) |

(52) U.S. Cl.
CPC ........ *H01L 51/0068* (2013.01); *C07C 209/10* (2013.01); *C07C 211/61* (2013.01); *C07C 213/02* (2013.01); *C07C 217/94* (2013.01); *C07D 209/86* (2013.01); *C07D 219/02* (2013.01); *C07D 307/91* (2013.01); *C07D 333/76* (2013.01); *C07D 405/12* (2013.01); *C07F 7/083* (2013.01); *C07F 7/0818* (2013.01); *C09K 11/06* (2013.01); *H01L 51/0059* (2013.01); *H01L 51/0065* (2013.01); *H01L 51/0067* (2013.01); *H01L 51/5056* (2013.01); *H05B 33/14* (2013.01); *C07C 2103/18* (2013.01); *C07C 2103/94* (2013.01); *C09K 2211/1011* (2013.01); *C09K 2211/1014* (2013.01)

(58) Field of Classification Search
CPC ... C07C 217/94; C07C 209/10; C07C 213/02; C07C 211/61; C07C 2103/94; C07C 2103/18; C09K 2211/1014; C09K 2211/1011; C09K 11/06; H05B 33/14; C07F 7/0818; C07F 7/083; H01L 51/0065; H01L 51/0067; H01L 51/5056; H01L 51/0068; H01L 51/0059; C07D 209/86; C07D 333/76; C07D 405/12; C07D 307/91; C07D 219/02
USPC .................... 546/102; 549/43, 460; 548/444; 556/413; 564/308
See application file for complete search history.

(56) References Cited

U.S. PATENT DOCUMENTS

| 7,998,597 B2 | 8/2011 | Saitoh et al. |
|---|---|---|
| 2006/0166034 A1 | 7/2006 | Saitoh et al. |
| 2010/0033081 A1 | 2/2010 | Yamada et al. |
| 2011/0198581 A1* | 8/2011 | Yabunouchi ......... C07D 209/56 257/40 |
| 2012/0161615 A1 | 6/2012 | Hong et al. |
| 2012/0248426 A1 | 10/2012 | Kato |
| 2013/0207046 A1 | 8/2013 | Pflumm et al. |
| 2015/0179940 A1* | 6/2015 | Mujica-Fernaud . H01L 51/0052 252/519.21 |

(Continued)

FOREIGN PATENT DOCUMENTS

| DE | 102010045405 A1 | 3/2012 |
|---|---|---|
| EP | 0879868 A2 | 11/1998 |

(Continued)

OTHER PUBLICATIONS

International Search Report for PCT/EP2013/001891 mailed Dec. 4, 2013.
English Abstract of Woo, H-S., et al., "Organic Semiconductor—Technology and Application", Industrial Chemistry Outlook, 2006, vol. 9, No. 3, pp. 8-17.
Woo, H-S., et al., "Organic Semiconductor—Technology and Application", Industrial Chemistry Outlook, 2006, vol. 9, No. 3, pp. 8-17.

*Primary Examiner* — Noble Jarrell
*Assistant Examiner* — Daniel Carcanague

(57) ABSTRACT

The present invention concerns particular fluorenes, the use of the compound in an electronic device, and an electronic device containing at least one of these compounds. The present invention further concerns a method for producing the compound and a formulation and composition containing one or more of the compounds.

14 Claims, No Drawings

(56) References Cited

U.S. PATENT DOCUMENTS

2015/0207075 A1\* 7/2015 Mujica-Fernaud .... C09K 11/06
  252/500

FOREIGN PATENT DOCUMENTS

| | | | |
|---|---|---|---|
| EP | 2415752 A1 | | 2/2012 |
| JP | 05303221 | \* | 11/1993 |
| JP | H1095972 A | | 4/1998 |
| JP | 11219787 | \* | 8/1999 |
| JP | 2001196177 | \* | 7/2001 |
| JP | 2004091350 A | | 3/2004 |
| JP | 3824385 B2 | | 9/2006 |
| JP | 2008019238 A | | 1/2008 |
| JP | 2011173973 | \* | 9/2011 |
| JP | 4795268 B2 | | 10/2011 |
| KR | 20080077288 A | | 8/2008 |
| KR | 20090114716 A | | 11/2009 |
| KR | 20090117078 | \* | 11/2009 |
| KR | 101072817 | \* | 10/2011 |
| KR | 20120066076 A | | 6/2012 |
| KR | 20120111670 | \* | 10/2012 |
| KR | 20130024521 | \* | 3/2013 |
| WO | WO-2004020387 A1 | | 3/2004 |
| WO | WO-2007072838 A1 | | 6/2007 |
| WO | WO-2007086701 A1 | | 8/2007 |
| WO | WO-2012034627 A1 | | 3/2012 |

\* cited by examiner

COMPOUNDS AND ORGANIC ELECTROLUMINESCENT DEVICES

CROSS-REFERENCE TO RELATED APPLICATIONS

This application is a national stage application (under 35 U.S.C. §371) of PCT/EP2013/001891, filed Jun. 27, 2013, which claims benefit of European Application No. 12005369.9, filed Jul. 23, 2012, both of which are incorporated herein by reference in their entirety.

The present invention relates to novel organic compounds, to the use of compound in an electroluminescent device, and to an electroluminescent device comprising at least one of the compounds. The present invention furthermore relates to a process for the preparation of the compounds and to compositions and formulations comprising at least one of the compounds.

The development of functional compounds for use in electroluminescent devices is currently the subject of intensive research. The aim here is, in particular, the development of compounds with which improved properties of the electroluminescent devices in one or more relevant points can be achieved, such as, for example, power efficiency, lifetime or colour coordinates of the emitted light.

The term electroluminescent device is in accordance with the present invention taken to mean, inter alia, organic light-emitting transistors (OLETs), organic field-quench devices (OFQDs), organic light-emitting electrochemical cells (OLECs, LECs or LEECs), organic laser diodes (O-lasers) and organic electroluminescent devices (OLEDs).

Of particular interest is the provision of compounds for use in the last-mentioned electronic devices called OLEDs (organic light-emitting diodes). The general structure and the functional principle of OLEDs are well known to the person skilled in the art and are described, inter alia, in U.S. Pat. Nos. 4,539,507, 5,151,629, EP 0676461 and WO 1998/27136.

Still further improvements are necessary with regard to the performance data of OLEDs, in particular in view of broad commercial use, for example in display devices or as light sources. Of particular importance in this connection are the lifetime, the efficiency and the operating voltage of the OLEDs and the colour values achieved. In addition, it is desirable for the compounds for use as functional materials in electronic devices to have high thermal stability and a high glass-transition temperature and to be sublimable without decomposition.

In this connection, there is a need, in particular, for alternative hole-transport materials. In the case of hole-transport materials in accordance with the prior art, the voltage generally increases with increasing layer thickness of the hole-transport layer. In practice, a greater layer thickness of the hole-transport layer would frequently be desirable, but this often has the consequence of a higher operating voltage and worse performance data. In this connection, there is a need for novel hole-transport materials which have high charge-carrier mobility, enabling thicker hole-transport layers to be achieved with only a slight increase in the operating voltage.

The prior art describes the use of various fluorenes as charge-transport material in electronic and electroluminescent devices.

The compounds described in the prior art are generally compounds which have an asymmetrical substitution in position 9 of the fluorene.

JP 05303221 discloses fluorenes which may be substituted by an amine group in position 2 or 4. The compounds containing the amine group in position 4 of the fluorene contain phenyl radicals. A few of these compounds exhibit an asymmetrical substitution in position 9 of the fluorene. The compounds are employed as photoreceptors.

In spite of the compounds that are already known, there continues to be a need for novel hole-transport and hole-injection materials for use in OLEDs. In particular, there is a need for materials with which the above-mentioned, highly desired improvements in the performance data and properties of the OLEDs can be achieved.

There is likewise a need for novel matrix materials for use in OLEDs and in other electronic devices. In particular, there is a need for matrix materials for phosphorescent dopants and for matrix materials for mixed-matrix systems which preferably result in good efficiency, a long lifetime and a low operating voltage of the electronic devices.

The present invention is thus based on the object of providing electroluminescent devices and compounds which are suitable for use in electroluminescent devices, such as, for example, in fluorescent or phosphorescent OLEDs, and which can be employed, in particular, as hole-injection materials and/or hole-transport material in a hole¬transport or exciton-blocking layer or as matrix material in an emitting layer.

In the course of the present invention, it has surprisingly been found that compounds of the formula (1) shown below are extremely suitable for the above-mentioned uses in electroluminescent devices.

The invention thus relates to an electroluminescent device comprising at least one compound of the formula (1)

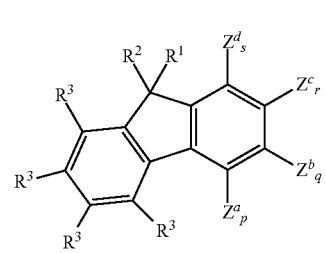

formula (1)

where the following applies to the symbols and indices used:

p, q, r, s
are 0 or 1, where p+q+r+s=1, preferably p=1 or r=1 or s=1 very preferably p=1 or r=1;

$Z^a_0$, $Z^b_0$, $Z^c_0$, $Z^d_0$
are, identically or differently on each occurrence, equal to $R^4$ $Z^a_1$, $Z^b_1$, $Z^c_1$, $Z^d_1$ are equal to

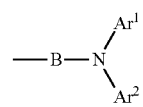

B is a single bond, a divalent aryl group having 6 to 30 ring atoms or a divalent heteroaryl group having 5 to 30 ring atoms, each of which may be substituted by one or more radicals $R^6$, preferably a single bond or a phenylene, biphenylene, terphenylene, naphthylene, pyridinylene, pyrimidinylene, pyrazinylene, pyridazinylene, triazinylene, dibenzofuranylene, dibenzothiophenylene fluorenylene, or carbazoylene group, which may be substituted by one or more radicals $R^6$, very preferably a single bond or a phenylene, biphenylene, terphenylene, naphthylene, dibenzofuranylene or dibenzothiophenylene fluorenylene, or carbazoylene group, which may be substituted by one or more radicals $R^6$, B is very particularly preferably a single bond or a phenylene group, which may be substituted by one or more radicals $R^6$, B is especially preferably a single bond, where, if B is a single bond, the nitrogen atom is bonded directly to the fluorene;

$Ar^1$, $Ar^2$
are on each occurrence, identically or differently, an aryl group having 10 to 60 ring atoms or a heteroaryl group 10 to 60 ring atoms, which may be substituted by one or more radicals $R^5$, which are identical to or different from one another, where both groups $Ar^1$ or $Ar^2$ each contain at least two or more aromatic or heteroaromatic rings, where two of the aromatic or heteroaromatic rings in $Ar^1$ and/or two of the aromatic or heteroaromatic rings in $Ar^2$ may be condensed, they are preferably in uncondensed form, and where two of the aromatic or heteroaromatic rings in $Ar^1$ may be bridged by a divalent group —O—, —S—, —Si($R^5$)$_2$—, —C($R^5$)$_2$ or —$NR^5$— or two of the aromatic or heteroaromatic rings in $Ar^2$ may be bridged by a divalent group —O—, —S—, —Si($R^5$)$_2$—, —C($R^5$)$_2$,— or —$NR^5$—, where unbridged rings are preferred and where an aromatic or heteroaromatic ring from $Ar^1$ may be bridged to an aromatic or heteroaromatic ring from $Ar^2$ by a divalent group —O—, —S—, —Si($R^5$)$_2$—, —$NR^5$— or —C($R^5$)$_2$—, where unbridged groups $Ar^1$ and $Ar^2$ are preferred;

$R^1$, $R^2$, $R^3$, $R^4$, and $R^5$
are H, D, F, Cl, Br, I, C(=O)$R^6$, CN, Si($R^6$)$_3$, NO$_2$, N($R^6$)$_2$, P(=O)($R^6$)$_2$, S(=O)$R^6$, S(=O)$_2R^6$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals $R^6$ and where one or more CH$_2$ groups in the above-mentioned groups may be replaced by —$R^6$C=C$R^6$—, —C≡C—, Si($R^6$)$_2$, C=O, C=S, C=$NR^6$, —C(=O)O—, —C(=O)$NR^6$—, P(=O)($R^6$), —O—, —S—, SO or SO$_2$ and where one or more H atoms in the above-mentioned groups may be replaced by D, F, Cl, Br, I, CN or NO$_2$, or an aromatic or heteroaromatic ring system having 6 to 30 aromatic ring atoms, which may in each case be substituted by one or more radicals $R^6$, or an aryloxy group having 5 to 60 aromatic ring atoms, which may be substituted by one or more radicals $R^6$, or an aralkyl group having 5 to 60 aromatic ring atoms, which may in each case be substituted by one or more radicals $R^6$, where the radicals $R^1$ and $R^2$ cannot be identical and the radicals $R^3$ to $R^5$ may on each occurrence be identical or different, but may be identical to either $R^1$ or to $R^2$;

$R^6$ is on each occurrence, identically or differently, H, D, F, Cl, Br, I, C(=O)$R^7$, CN, Si($R^7$)$_3$, NO$_2$, P(=O)($R^7$)$_2$, S(=O)$R^7$, S(=O)$_2R^7$, N($R^7$)$_2$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals $R^7$ and where one or more CH$_2$ groups in the above-mentioned groups may be replaced by —$R^7$C=C$R^7$—, —C≡C—, Si($R^7$)$_2$, C=O, C=S, C=$NR^7$, —C(=O)O—, —C(=O)$NR^7$—, P(=O)($R^7$), —O—, —S—, SO or SO$_2$ and where one or more H atoms in the above-mentioned groups may be replaced by D, F, Cl, Br, I, CN or NO$_2$, or an aromatic or heteroaromatic ring system having 5 to 30 aromatic ring atoms, which may in each case be substituted by one or more radicals $R^7$, or an aryloxy or heteroaryloxy group having 5 to 30 aromatic ring atoms, which may be substituted by one or more radicals $R^7$, where two or more adjacent substituents $R^6$ may form a mono- or polycyclic ring system with one another;

$R^7$ is selected from the group consisting of H, D, F, an aliphatic hydrocarbon radical having 1 to 20 C atoms or an aromatic or heteroaromatic ring system having 5 to 30 C atoms, in which one or more H atoms may be replaced by D or F, where two or more adjacent substituents $R^7$ may form a mono- or polycyclic ring system with one another.

In a preferred embodiment, the compound of the formula (1) contains no condensed aromatic or heteroaromatic ring systems having more than 10 ring atoms.

The asymmetrical substitution in position 9 of the fluorene results, in the case of suitable substitution of the fluorene in the other positions, in a chiral molecule. In the present invention, the racemates are also covered besides the enantiomerically pure R and S forms. The electroluminescent devices according to the invention therefore comprise either at least one of the compound of the formula (1) in the R or S form or as racemate, preferably as racemate.

The numbering on the fluorene is defined as follows,

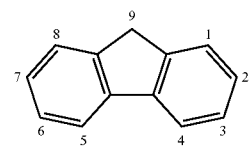

An aryl group in the sense of this invention contains 6 to 60 aromatic ring atoms; a heteroaryl group in the sense of this invention contains 5 to 60 aromatic ring atoms, at least one of which is a heteroatom. The heteroatoms are preferably selected from N, O and S. This represents the basic definition. If other preferences are indicated in the description of the present invention, for example with respect to the number of aromatic ring atoms or the heteroatoms present, these apply.

An aryl group or heteroaryl group here is taken to mean either a simple aromatic ring, i.e. benzene, or a simple heteroaromatic ring, for example pyridine, pyrimidine or thiophene, or a condensed (annellated) aromatic or heteroaromatic polycycle, for example naphthalene, phenanthrene, quinoline or carbazole. A condensed (annellated) aromatic or heteroaromatic polycycle in the sense of the present application consists of two or more simple aromatic or heteroaromatic rings condensed with one another.

An aryl or heteroaryl group, which may in each case be substituted by the above-mentioned radicals and which may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aryloxy group in accordance with the definition of the present invention is taken to mean an aryl group, as defined above, which is bonded via an oxygen atom. An analogous definition applies to heteroaryloxy groups.

An aromatic ring system in the sense of this invention contains 6 to 60 C atoms in the ring system. A heteroaromatic ring system in the sense of this invention contains 5 to 60 aromatic ring atoms, at least one of which is a heteroatom. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an $sp^3$-hybridised C, Si, N or O atom, an $sp^2$-hybridised C or N atom or an sp-hybridised C atom. Thus, for example, systems such as 9,9'-spirobifluorene, 9,9'-diarylfluorene, triarylamine, diaryl ether, stilbene, etc., are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl or heteroaryl groups are linked to one another via single bonds are also taken to be aromatic or heteroaromatic ring systems in the sense of this invention, such as, for example, systems such as biphenyl, terphenyl or diphenyltriazine.

An aromatic or heteroaromatic ring system having 5-60 aromatic ring atoms, which may in each case also be substituted by radicals as defined above and which may be linked to the aromatic or heteroaromatic group via any desired positions, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenylene, quaterphenyl, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or combinations of these groups.

For the purposes of the present invention, a straight-chain alkyl group having 1 to 40 C atoms or a branched or cyclic alkyl group having 3 to 40 C atoms or an alkenyl or alkynyl group having 2 to 40 C atoms, in which, in addition, individual H atoms or $CH_2$ groups may be substituted by the groups mentioned above under the definition of the radicals, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

It is furthermore preferred for B in the compound of the formula (1) to be an o-phenylene, m-phenylene or p-phenylene group, a 1,4-naphthylene, 2,4-naphthylene, 1,5-naphthylene or 2,5-naphthylene group, a 3,7-dibenzofuranylene group or a 3,7-dibenzothiophenylene group, where it is very preferred for B to be an o-phenylene, m-phenylene or p-phenylene group and it is very particularly preferred for B to be a p-phenylene group, where the groups may be substituted by one or more radicals $R^4$, which may be identical or different on each occurrence, where the groups are preferably unsubstituted.

For the purposes of the present invention, preference is given to an electroluminescent device comprising at least one compound of the general formula (2)

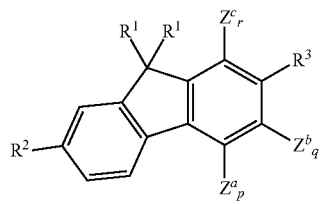

formula (2)

where the above definitions apply to the indices and symbols used

Preference is furthermore given to an electroluminescent device comprising at least one compound of the general formula (1) or (2), characterised in that the radicals $R^1$ and $R^2$, which are different from one another, are a straight-chain alkyl or alkoxy group having 1 to 20 C atoms or a branched or cyclic alkyl or alkoxy group having 3 to 20 C atoms, where the above-mentioned groups may each be substituted by one or more radicals $R^6$, or from an aromatic or heteroaromatic ring system having 5 to 30 aromatic ring atoms, which may in each case be substituted by one or more radicals $R^6$, or an aryloxy group having 6 to 60 aromatic ring atoms, which may be substituted by one or more radicals $R^6$, or an aralkyl group having 5 to 60 aromatic ring atoms, which may in each case be substituted by one or more radicals $R^6$.

It is furthermore very preferred if the radicals $R^1$ and $R^2$, which are different from one another, are a straight-chain alkyl group having 1 to 20 C atoms or a branched or cyclic alkyl group having 3 to 20 C atoms, where the above-mentioned groups may each be substituted by one or more radicals $R^6$, or an aromatic or heteroaromatic ring system having 6 to 30 aromatic ring atoms, which may in each case be substituted by one or more radicals $R^6$.

It is furthermore very particularly preferred if one of the two radicals $R^1$ and $R^2$ is a straight-chain alkyl group having 1 to 20 C atoms or a branched or cyclic alkyl group having 3 to 20 C atoms, where the above-mentioned groups may each be substituted by one or more radicals $R^6$, where it is especially preferred if one of the two radicals $R^1$ and $R^2$ is a methyl, ethyl, n-/i-propyl or n-/i-/t-butyl group and the other of the two radicals $R^1$ and $R^2$ is an aromatic or heteroaromatic ring system having 6 to 30 aromatic ring atoms, which may in each case be substituted by one or more radicals $R^6$, where the ring system is especially preferably selected from the group consisting of a phenyl, biphenyl, terphenyl or pyridyl group.

Preference is furthermore given to an electroluminescent device comprising at least one compound of the general formula (1) or (2), characterised in that $R^3$ is selected on each occurrence, identically or differently, preferably identically, from H, D, F, Cl, Br, I, $N(R^6)_2$, a straight-chain alkyl or alkoxy group having 1 to 20 C atoms or a branched or cyclic alkyl or alkoxy group having 3 to 20 C atoms or an alkenyl or alkynyl group having 2 to 20 C atoms, where the above-mentioned groups may each be substituted by one or more radicals $R^6$ and where one or more H atoms in the above-mentioned groups may be replaced by D, F, Cl, Br, I, CN or $NO_2$, or an aromatic or heteroaromatic ring system having 6 to 30 aromatic ring atoms, which may in each case be substituted by one or more radicals $R^6$, or an aryloxy group having 5 to 60 aromatic ring atoms, which may be substituted by one or more radicals $R^6$, or an aralkyl group having 5 to 60 aromatic ring atoms, which may in each case be substituted by one or more radicals $R^6$, where two or more radicals $R^3$ may be linked to one another and form a ring.

It is furthermore very preferred if the radical $R^3$ is selected on each occurrence, identically or differently, preferably identically, from H, D, F, Cl, Br, I, $N(R^6)_2$, a straight-chain alkyl group having 1 to 20 C atoms or a branched or cyclic alkyl group having 3 to 20 C atoms, where the above-mentioned groups may each be substituted by one or more radicals $R^6$ and where one or more H atoms in the above-mentioned groups may be replaced by D, F, Cl, Br, I, CN or $NO_2$, or an aromatic or heteroaromatic ring system having 6 to 30 aromatic ring atoms, which may in each case be substituted by one or more radicals $R^6$. Some of the particularly preferred aromatic or heteroaromatic ring systems for the radicals $R^3$ are selected from the group consisting of a phenyl, biphenyl, terphenyl, quarterphenyl, pyridyl, triazinyl, naphthyl, fluorenyl, dibenzothiophenyl, dibenzofuranyl group, where the respective groups may be substituted by one or more radicals $R^6$.

In a very particularly preferred embodiment, the present invention relates to an electroluminescent device comprising at least one compound of the general formula (1) which is characterised in that $R^3$ is equal to H.

In a further very particularly preferred embodiment, the present invention relates to an electroluminescent device comprising at least one compound of the general formula (1) which is characterised in that $R^3$ is a straight-chain alkyl group having 1 to 20 C atoms or a branched or cyclic alkyl group having 3 to 20 C atoms.

In still a further very particularly preferred embodiment, the present invention relates to an electroluminescent device comprising at least one compound of the general formula (1) which is characterised in that $R^3$ represents an aromatic or heteroaromatic ring system having 6 to 30 aromatic ring atoms.

Preference is furthermore given to an electroluminescent device comprising at least one compound of the general formula (1) or (2), characterised in that $R^4$ is selected on each occurrence, identically or differently, from H, D, F, Cl, Br, I, $N(R^6)_2$, a straight-chain alkyl or alkoxy group having 1 to 20 C atoms or a branched or cyclic alkyl or alkoxy group having 3 to 20 C atoms, where the above-mentioned groups may each be substituted by one or more radicals $R^6$ and where one or more H atoms in the above-mentioned groups may be replaced by D, F, Cl, Br, I, CN or $NO_2$, or an aromatic or heteroaromatic ring system having 6 to 30 aromatic ring atoms, which may in each case be substituted by one or more radicals $R^6$, or an aryloxy group having 5 to 60 aromatic ring atoms, which may be substituted by one or more radicals $R^6$, or an aralkyl group having 5 to 60 aromatic ring atoms, which may in each case be substituted by one or more radicals $R^6$, where two or more radicals $R^4$ may be linked to one another and may form a ring, where it is preferred if the radicals $R^4$ do not form a ring closure.

In a preferred embodiment, the present invention relates to an electroluminescent device comprising at least one compound of the general formula (3)

formula (3)

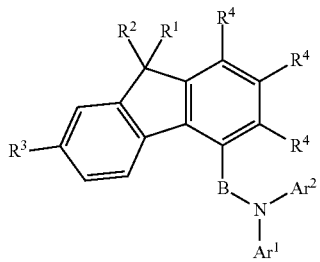

where the above definitions apply to the symbols and indices used.

In a very preferred embodiment, the present invention relates to an electroluminescent device comprising at least one compound of the general formula (4)

formula (4)

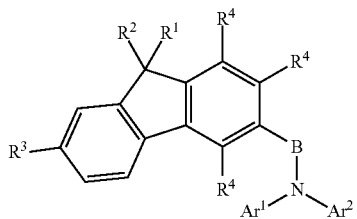

where the above definitions apply to the symbols and indices used.

In a furthermore preferred embodiment, the present invention relates to an electroluminescent device comprising at least one compound of the general formula (5)

formula (5)

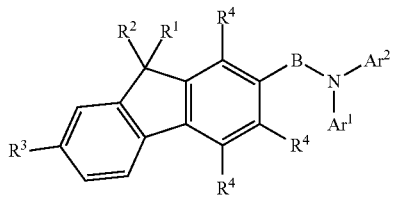

where the above definitions apply to the symbols and indices used.

In a furthermore preferred embodiment, the present invention relates to an electroluminescent device comprising at least one compound of the general formula (6)

formula (6)

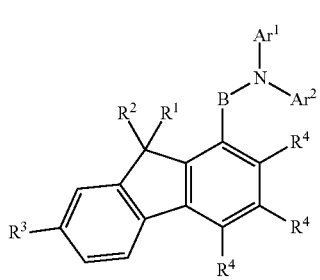

where the above definitions apply to the symbols and indices used,

In a furthermore preferred embodiment, the present invention relates to an electroluminescent device comprising at least one compound of the general formula (7)

formula (7)

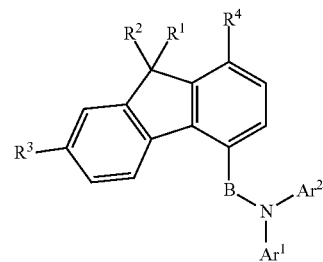

where the above definitions apply to the symbols and indices used.

In a furthermore very preferred embodiment, the present invention relates to an electroluminescent device comprising at least one compound of the general formula (8)

formula (8)

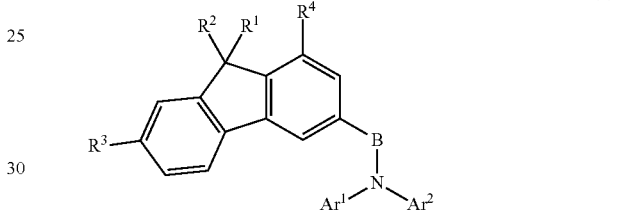

where the above definitions apply to the symbols and indices used.

In a furthermore very preferred embodiment, the present invention relates to an electroluminescent device comprising at least one compound of the general formula (9)

formula (9)

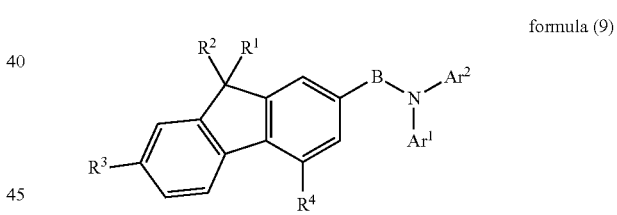

where the above definitions apply to the symbols and indices used.

In a very particularly preferred embodiment, the present invention relates to an electroluminescent device comprising at least one compound of the general formula (10)

formula (10)

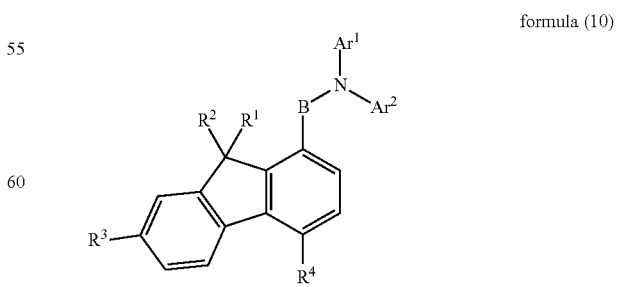

where the above definitions apply to the symbols and indices used.

In a furthermore very preferred embodiment, the present invention relates to an electroluminescent device comprising at least one compound of the general formula (11)

formula (11)
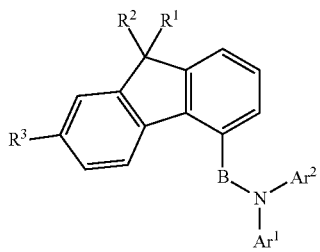

where the above definitions apply to the symbols and indices used.

In a furthermore very preferred embodiment, the present invention relates to an electroluminescent device comprising at least one compound of the general formula (12)

formula (12)
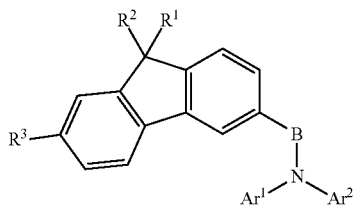

where the above definitions apply to the symbols and indices used.

In a furthermore very preferred embodiment, the present invention relates to an electroluminescent device comprising at least one compound of the general formula (13)

formula (13)
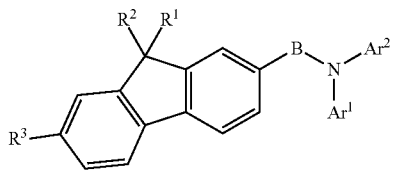

where the above definitions apply to the symbols and indices used.

In a very particularly preferred embodiment, the present invention relates to an electroluminescent device comprising at least one compound of the general formula (14)

formula (14)
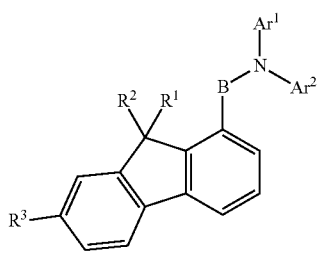

where the above definitions apply to the symbols and indices used.

Preference is furthermore given to a compound of the formulae (1) to (14) indicated above in which B is selected from the groups of the formulae (15) to (36), where these groups may also be substituted by one or more radicals $R^6$, which are independent of one another, and where $R^6$ is defined as indicated above:

formula (15)
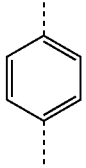

formula (16)
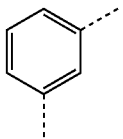

formula (17)
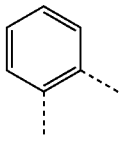

formula (18)
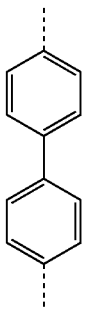

formula (19)
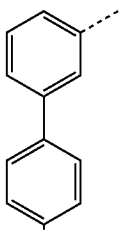

formula (20)
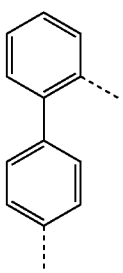

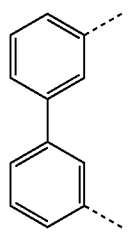
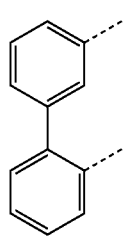
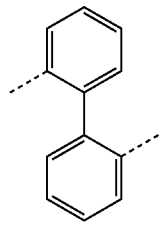
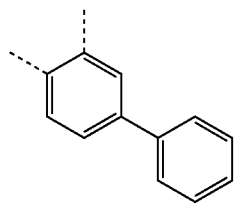
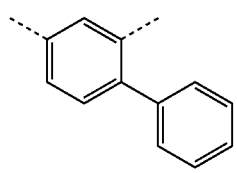
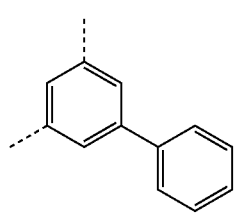
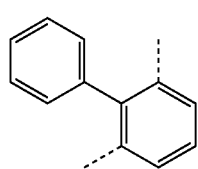
formula (21)
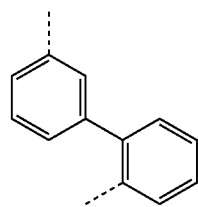
formula (22)
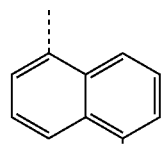
formula (23)
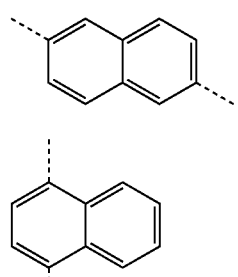
formula (24)
formula (25)
formula (26)
formula (27)
formula (28)
formula (29)
formula (30)
formula (31)
formula (32)
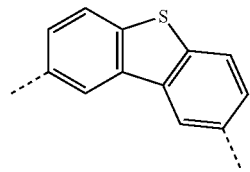
formula (33)
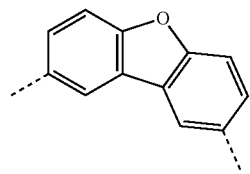
formula (34)
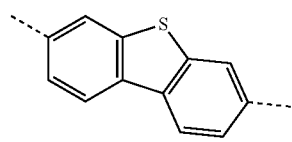
formula (35)
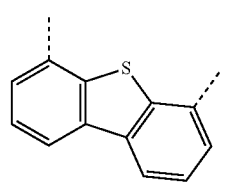
formula (36)

-continued

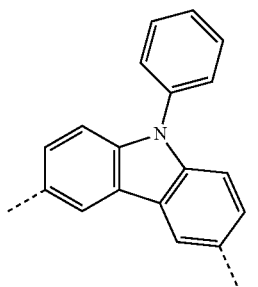

formula (37)

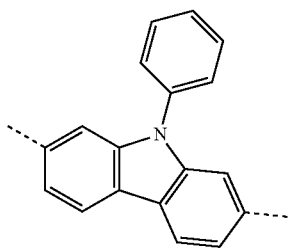

formula (38)

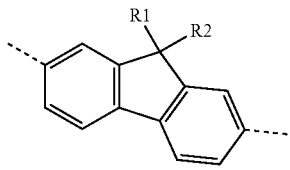

formula (39)

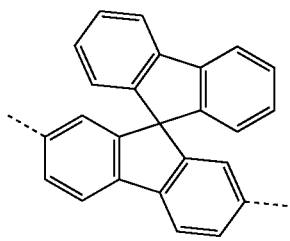

formula (40)

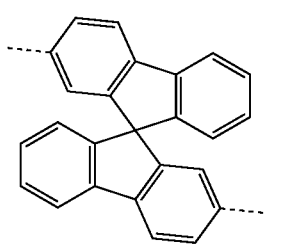

formula (41)

where the dashed lines denote the linking positions.

Particular preference is given to a compound of the formulae (1) to (14) indicated above in which B is selected from the groups of the formulae (15) to (41), where these groups are unsubstituted.

Very particular preference is given to a compound of the formula (1) to (14) indicated above in which B conforms to the formula (15), where this group is unsubstituted.

Especial preference is given to a compound of the formulae (1) to (14), characterised in that B is a single bond, in which case the nitrogen atom is bonded directly to the fluorene via a single bond.

Ar$^1$ and Ar$^2$ are preferably selected, identically or differently on each occurrence, from a phenylpyridyl, phenylnaphthyl, biphenyl, terphenyl or waterphenyl group, which may be substituted by one or more radicals R$^6$, which may be identical to or different from one another, where two of the aromatic or heteroaromatic rings in Ar$^1$ may be bridged by a divalent group —O—, —S—, —C(R$^5$)$_2$— or —Si(R$^5$)$_2$— or two of the aromatic or heteroaromatic rings in Ar$^2$ may be bridged by a divalent group —O—, —S—, —C(R$^5$)$_2$— or —Si(R$^5$)$_2$—, where unbridged rings are preferred, and where an aromatic or heteroaromatic ring from Ar$^1$ may be bridged to an aromatic or heteroaromatic ring from Ar$^2$ by a divalent group —O—, —S—, —Si(R$^5$)$_2$—, —NR$^5$— or —C(R$^5$)$_2$—, where unbridged groups Ar$^1$ and Ar$^2$ are preferred.

In a very preferred embodiment of the present invention, Ar$^1$ and Ar$^2$ are selected, identically or differently on each occurrence, from the following groups of the formulae (42) to (142), which may be substituted by one or more radicals R$^5$:

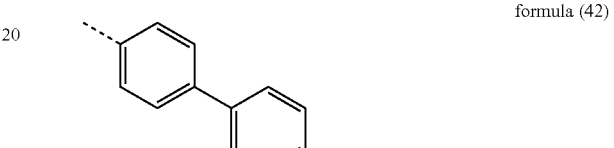

formula (42)

formula (43)

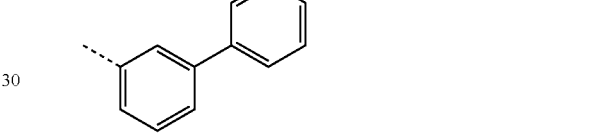

formula (44)

formula (45)

formula (46)

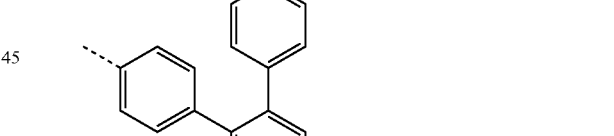

formula (47)

formula (48)
formula (49)
formula (50)
formula (51)
formula (52)
formula (53)
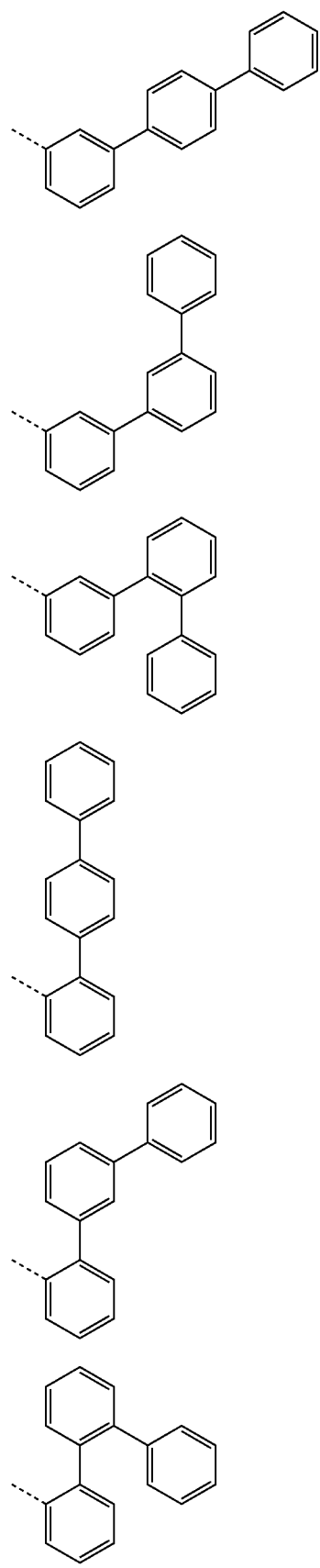
formula (54)
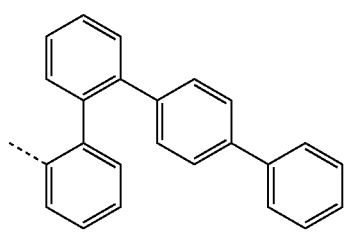
formula (55)
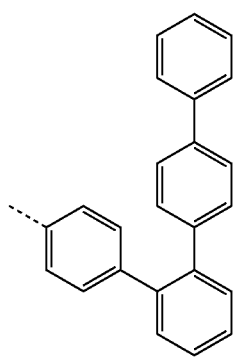
formula (56)
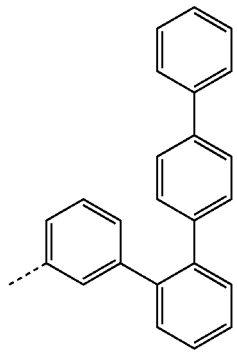
formula (57)
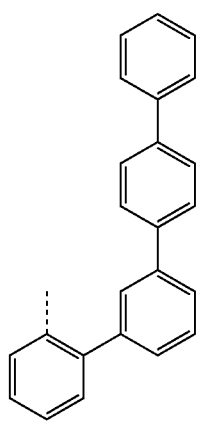

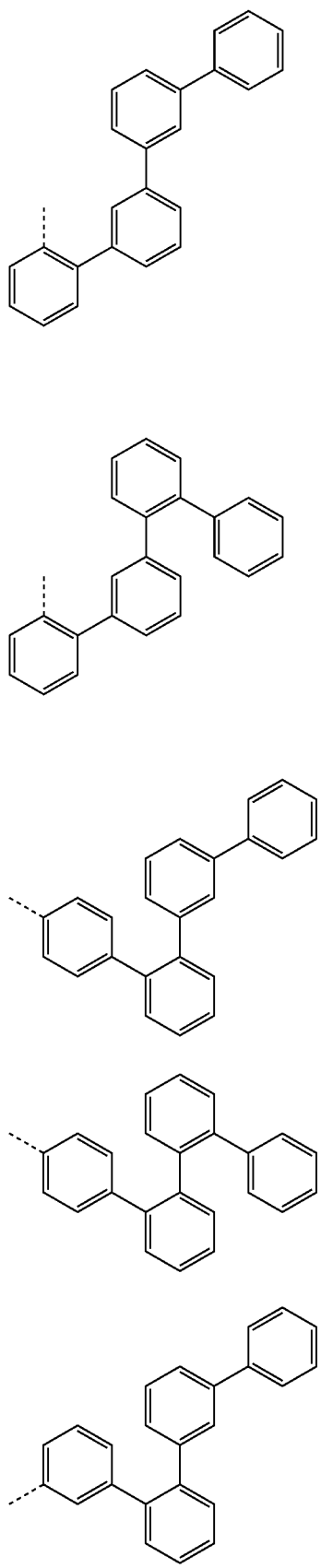
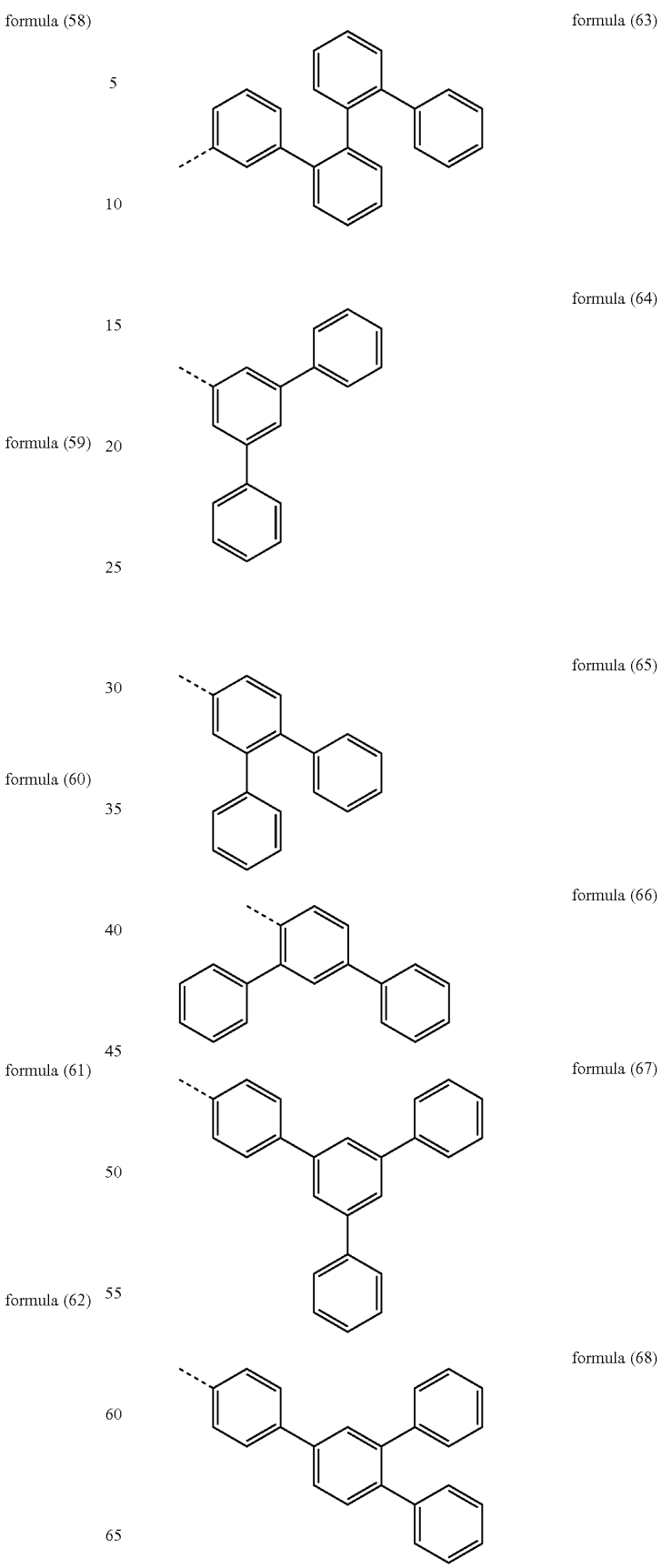

formula (69)
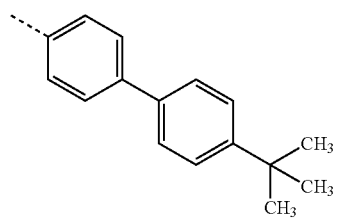
formula (70)
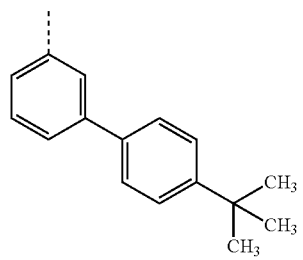
formula (71)
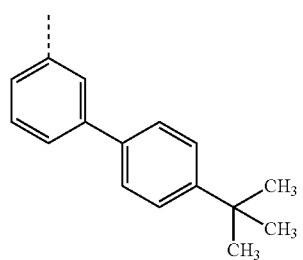
formula (72)
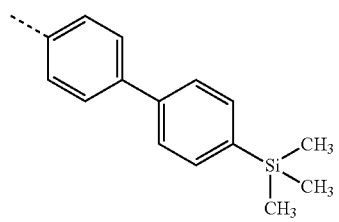
formula (73)
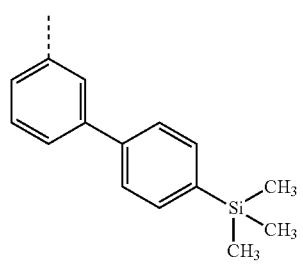
formula (74)
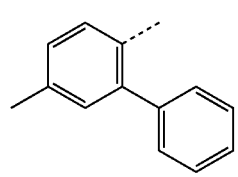
formula (75)
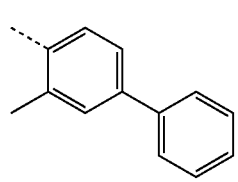
formula (76)
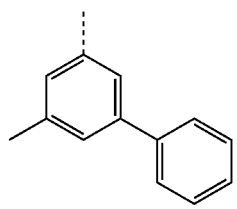
formula (77)
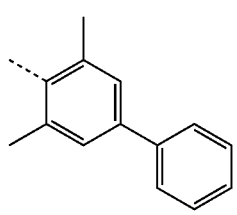
formula (78)
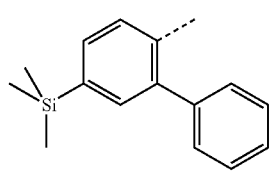
formula (79)
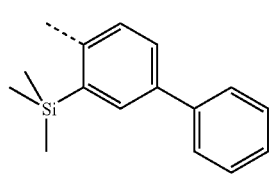
formula (80)
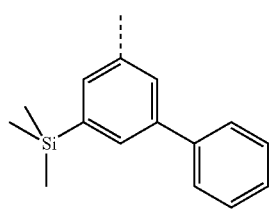
formula (81)
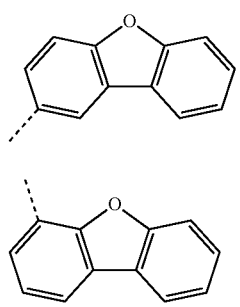
formula (82)
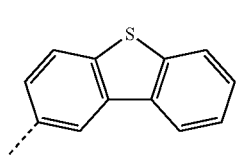
formula (83)
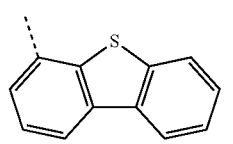
formula (84)

formula (85)
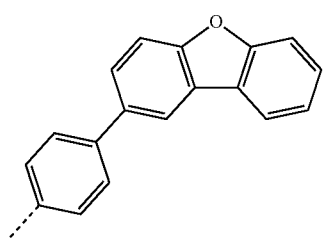
formula (86)
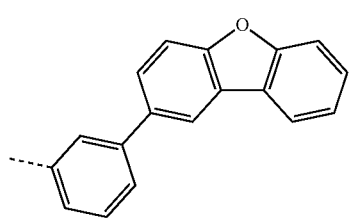
formula (87)
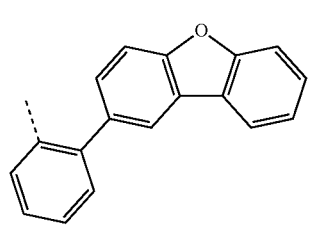
formula (88)
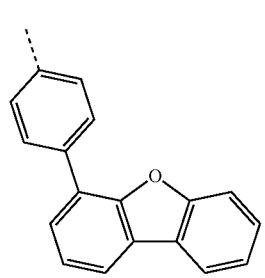
formula (89)
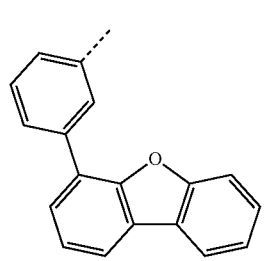
formula (90)
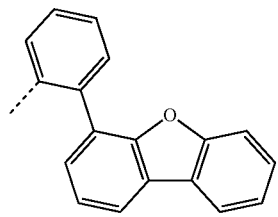
formula (91)
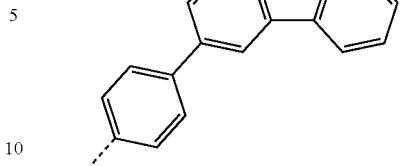
formula (92)
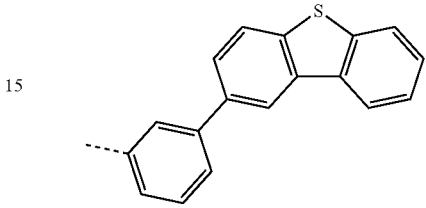
formula (93)
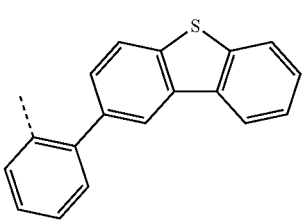
formula (94)
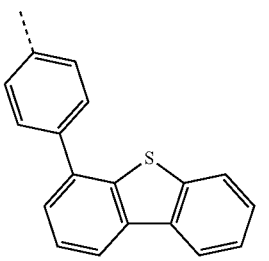
formula (95)
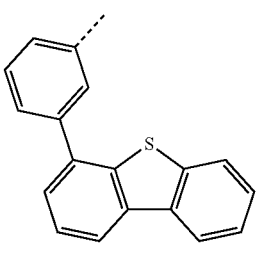
formula (96)
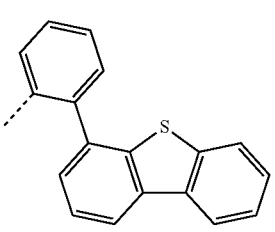
formula (97)
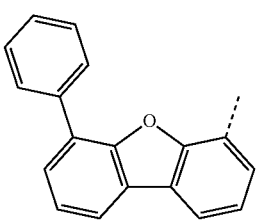

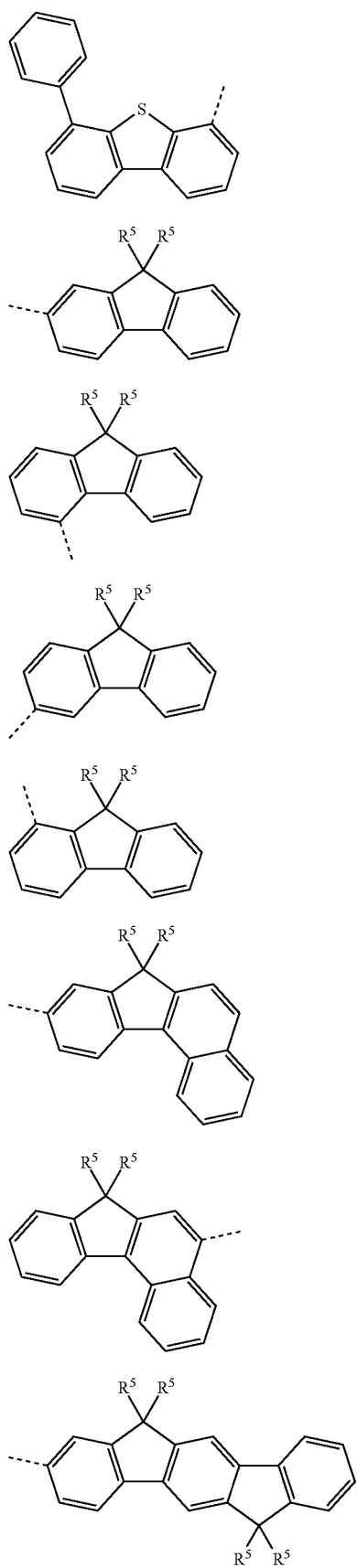
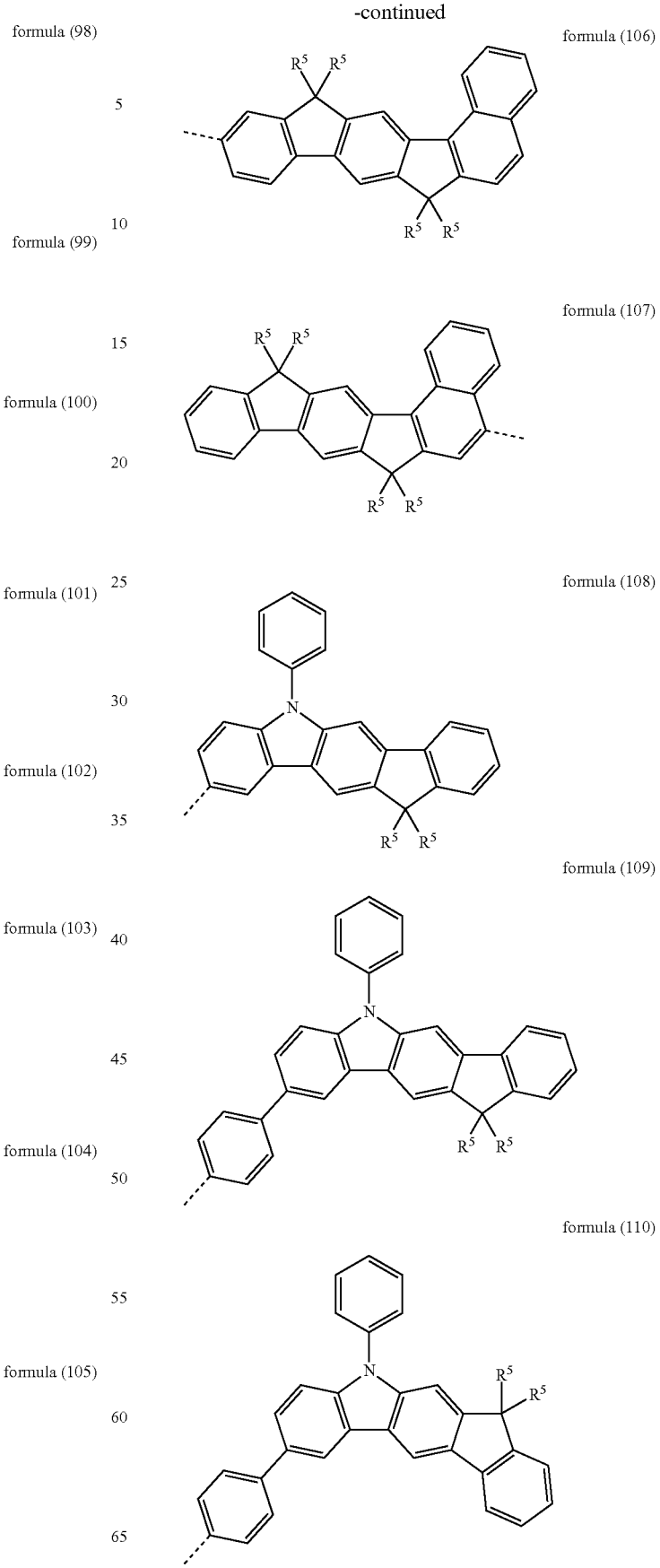

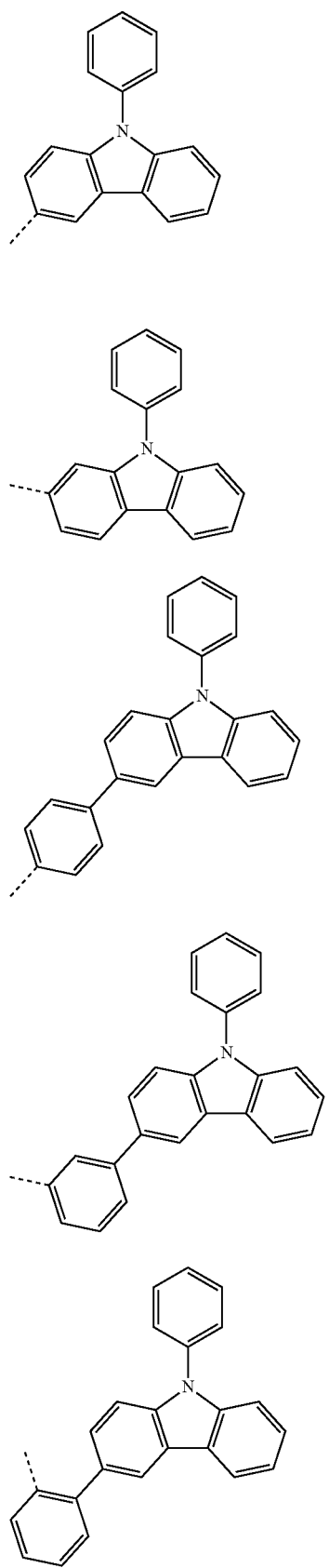
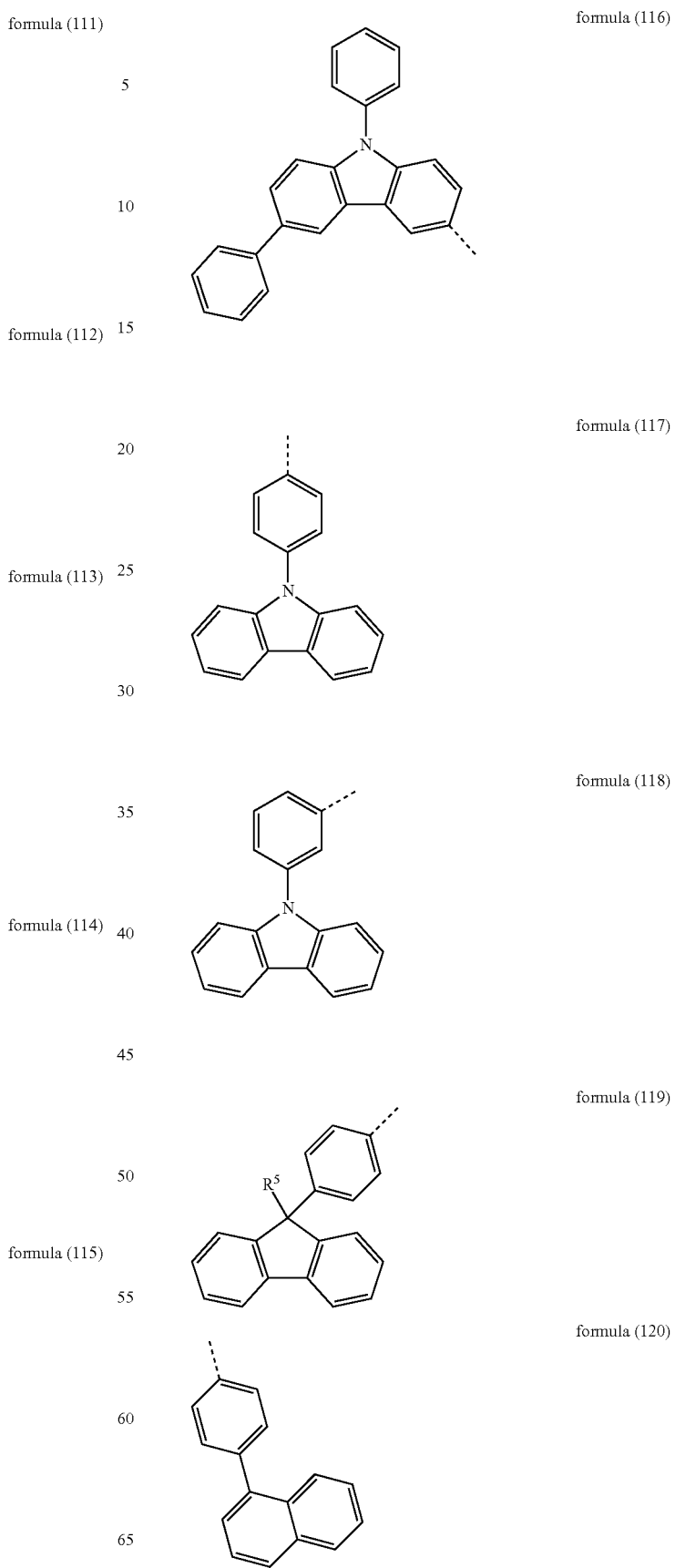
formula (111)
formula (112)
formula (113)
formula (114)
formula (115)
formula (116)
formula (117)
formula (118)
formula (119)
formula (120)

formula (121)
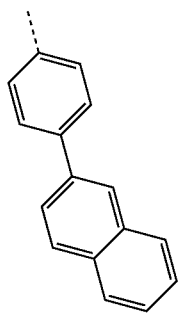
formula (122)
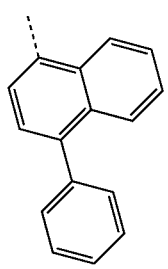
formula (123)
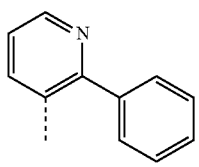
formula (124)
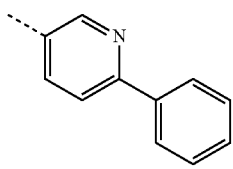
formula (125)
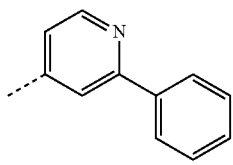
formula (126)
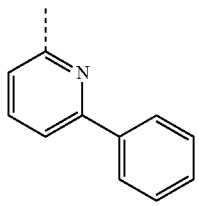
formula (127)
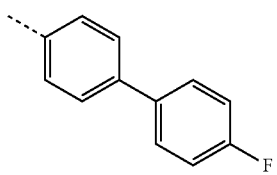
formula (128)
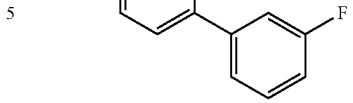
formula (129)
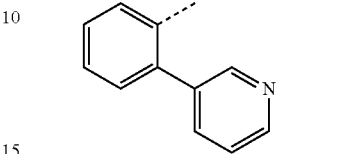
formula (130)
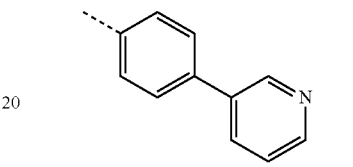
formula (131)
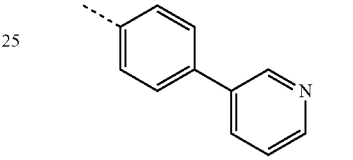
formula (132)
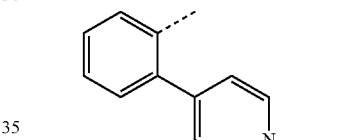
formula (133)
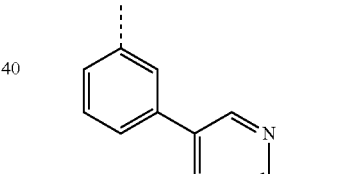
formula (134)
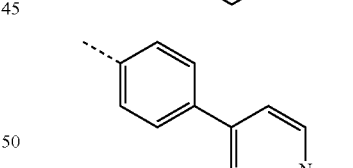
formula (135)
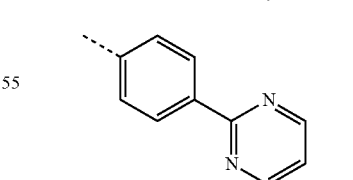
formula (136)
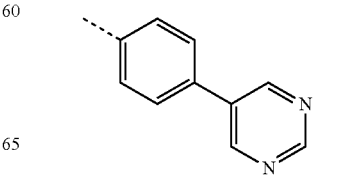

-continued formula (137)
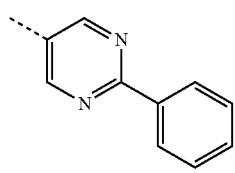

formula (138)
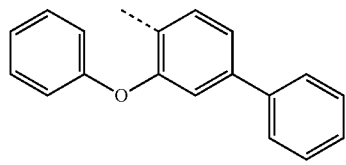

formula (139)
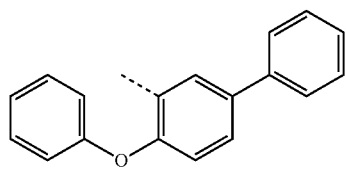

formula (140)
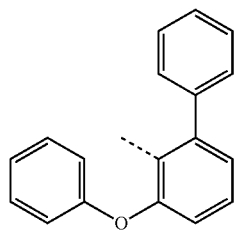

formula (141)
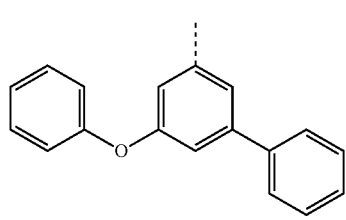

formula (142)
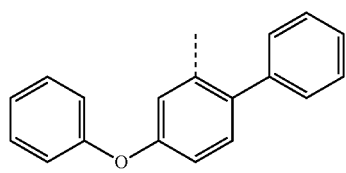

where the dashed line denotes the linking position to the nitrogen atom.

Especial preference is given to an electroluminescent device comprising at least one compound of the formula (143) to (145), where the above definitions apply to the symbols used and where h and i may be, independently of one another, 0, 1, 2, 3 and 4 and j and k may be, independently of one another, 0, 1, 2, 3, 4 and 5.

formula (143)
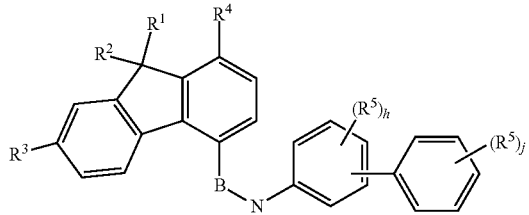

formula (144)
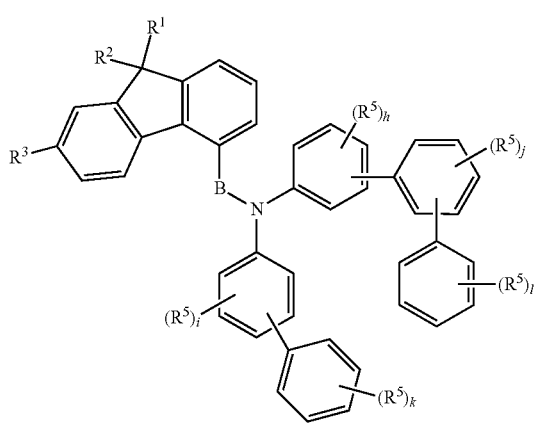

formula (145)
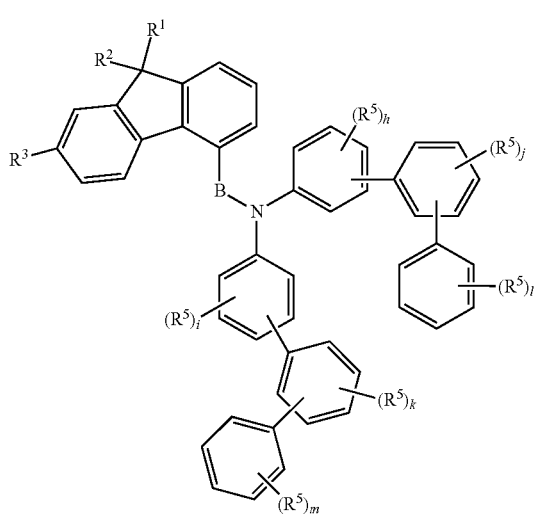

It is still more preferred if the following applies to the symbols used in the compounds of the formulae (143) to (145):

$R^1$ and $R^2$,
which are different from one another, are a straight-chain alkyl group having 1 to 20 C atoms or a branched or cyclic alkyl group having 3 to 20 C atoms, where the above-mentioned groups may each be substituted by one or more radicals $R^6$, or an aromatic or heteroaromatic ring system having 6 to 30 aromatic ring atoms, which may in each case be substituted by one or more radicals $R^6$, where it is especially preferred for one of the two radicals $R^1$ and $R^2$ to be a straight-chain alkyl group having 1 to 20 C atoms or a branched or cyclic alkyl group having 3 to 20 C atoms, where the above-mentioned groups may each be substituted by one or more radicals $R^6$, where it is furthermore preferred for one of the two radicals $R^1$ and $R^2$ to be a methyl, ethyl, n-/i-propyl or n-/i-/t-butyl group and for the other of the two radicals $R^1$ and $R^2$ to be an aromatic or heteroaromatic ring system having 6 to 30 aromatic ring atoms, which may in each case be substituted by one or more radicals $R^6$, where the ring system is especially preferably selected from the group consisting of a phenyl, biphenyl, terphenyl or pyridyl group;

$R^3$ is H, D, F, Cl, Br, I, a straight-chain alkyl group having 1 to 20 C atoms or a branched or cyclic alkyl group having 3 to 20 C atoms, where the above-mentioned groups may each be substituted by one or more radicals $R^6$ and where one or more H atoms in the above-mentioned groups may be replaced by D, F, Cl, Br, I, CN or $NO_2$, or an aromatic or heteroaromatic ring system having 6 to 30 aromatic ring atoms, which may in each case be substituted by one or more radicals $R^6$, $R^3$ is especially preferably equal to H;

B is a single bond or a phenylene, biphenylene, terphenylene, naphthylene, dibenzofuranylene or dibenzothiophenylene fluorenylene, or carbazoylene group, which may be substituted by one or more radicals $R^6$, B is especially preferably a single bond;

and where $R^6$ is defined as indicated above, where it is especially preferred for $R^6$ to be equal to H.

Especial preference is also given to an electroluminescent device comprising at least one compound of the formula (146) to (148), where the above definitions apply to the symbols used and where h and i may be, independently of one another, 0, 1, 2, 3 and 4 and j and k may be, independently of one another, 0, 1, 2, 3, 4 and 5.

formula (146)

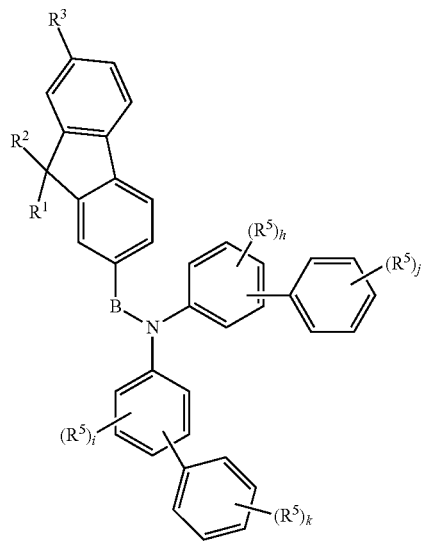

formula (147)

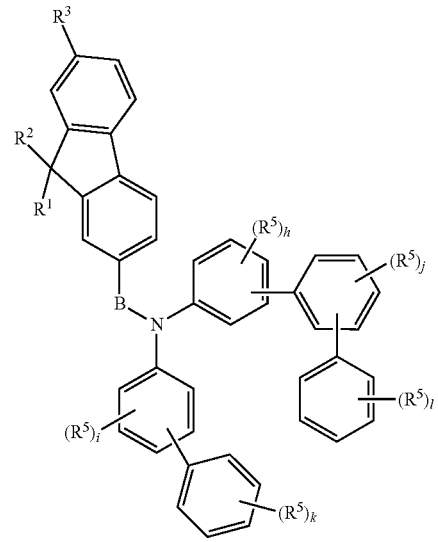

formula (148)

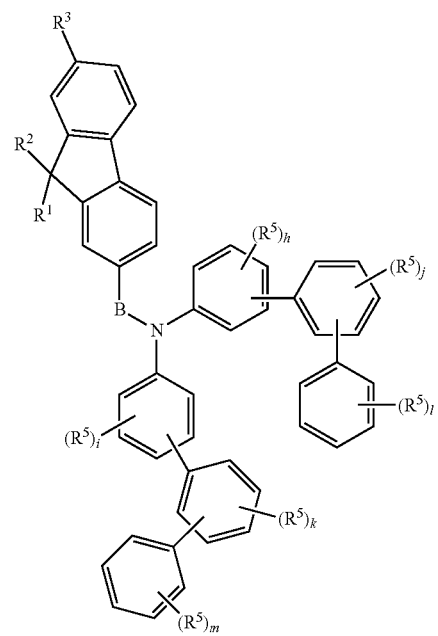

It is still more preferred if the following applies to the symbols used in the compounds of the formulae (146) to (148):

$R^1$ and $R^2$, which are different from one another, are a straight-chain alkyl group having 1 to 20 C atoms or a branched or cyclic alkyl group having 3 to 20 C atoms, where the above-mentioned groups may each be substituted by one or more radicals $R^6$, or an aromatic or heteroaromatic ring system having 6 to 30 aromatic ring atoms, which may in each case be substituted by one or more radicals $R^6$, where it is especially preferred for one of the two radicals $R^1$ and $R^2$ to be a straight-chain alkyl group having 1 to 20 C atoms or a branched or cyclic alkyl group having 3 to 20 C atoms, where the above-mentioned groups may each be substituted by one or more radicals $R^6$, where it is furthermore preferred for one of the two radicals $R^1$ and $R^2$ to be a methyl, ethyl, n-/i-propyl or n-/i-/t-butyl group and for the other of the two radicals $R^1$ and $R^2$ to be an aromatic or heteroaromatic ring system having 6 to 30 aromatic ring atoms, which may in each case be substituted by one or more radicals $R^6$, where the ring system is especially preferably selected from the group consisting of a phenyl, biphenyl, terphenyl or pyridyl group;

$R^3$ is H, D, F, Cl, Br, I, a straight-chain alkyl group having 1 to 20 C atoms or a branched or cyclic alkyl group having 3 to 20 C atoms, where the above-mentioned groups may each be substituted by one or more radicals $R^6$ and where one or more H atoms in the above-mentioned groups may be replaced by D, F, Cl, Br, I, CN or $NO_2$, or an aromatic or heteroaromatic ring system having 6 to 30 aromatic ring atoms, which may in each case be substituted by one or more radicals $R^6$, $R^3$ is especially preferably equal to H;

B is a single bond or a phenylene, biphenylene, terphenylene, naphthylene, dibenzofuranylene or dibenzothiophenylene fluorenylene, or carbazoylene group, which may be substituted by one or more radicals $R^6$, B is especially preferably a single bond;

and where $R^5$ is defined as indicated above, where it is especially preferred for $R^6$ to be equal to H.

In a very particularly preferred embodiment, the present invention relates to compounds of the general formula (1) characterised in that it is a monoamine or diamine compound, especially preferably a monoamine compound.

The device according to the invention can be any electroluminescent device. For the purposes of the present invention, the electroluminescent device is preferably an organic light-emitting transistor (OLETs), an organic field quench device (OFQDs), an organic light-emitting electrochemical cells (OLECs, LECs or LEECs), an organic laser diode (O-laser) and organic light-emitting diode (OLEDs). It is very preferably an organic light-emitting electrochemical cells (OLECs, LECs or LEECs) or an organic light-emitting diode (OLEDs). The electroluminescent device according to the invention is very particularly preferably an organic light-emitting diode (OLEDs).

The compounds of the general formula (1) are employed, in particular, in the following layers and with the following function in the electroluminescent devices:

as hole-transport material in a hole-transport or hole-injection layer as exciton-blocking material, as electron-blocking material, as matrix material in an emitting layer, as emitting material in an emitting layer The synthesis of the compounds can be prepared by processes which are known to the person skilled in the art from the prior art. The preparation can be carried out, for example, by means of halogenation, Buchwald coupling and Suzuki coupling.

The following reaction scheme shows a preferred synthetic route for the preparation of the compounds of the formula (1). For the synthesis of the compounds, on the fluorene compound A is reacted in a Buchwald coupling to an amine B of the formula $Ar^1$—NH—$Ar^2$

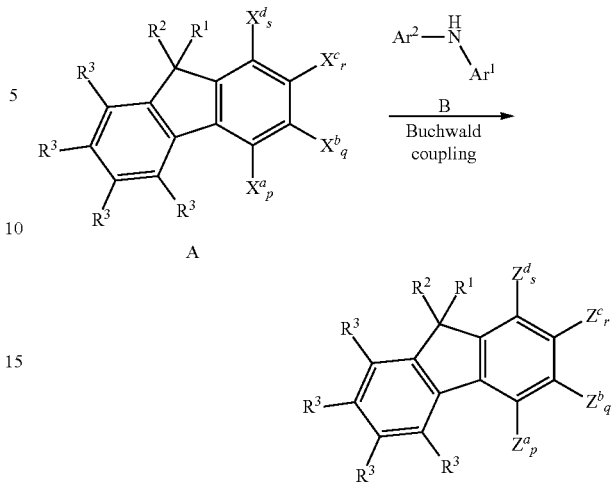

where the above definitions apply to the symbols and indices used and where $X^a_0$, $X^b_0$, $X^c_0$, $X^d_0$ are, identically or differently on each occurrence, equal to $R^4$ and $X^a_1$, $X^b_1$, $X^c_1$, $X^d_1$ are equal to —B—Y, where Y is a leaving group, for example halogen.

Another preferred synthetic route for the preparation of the compounds is depicted in the following reaction scheme. The synthetic route comprises two coupling reactions: firstly, the fluorene compound A is reacted with an amine B of the formula $Ar^1$—$NH_2$ in a first Buchwald coupling. Finally, a second Buchwald coupling is carried out to a compound D, for example with a bromoaryl compound,

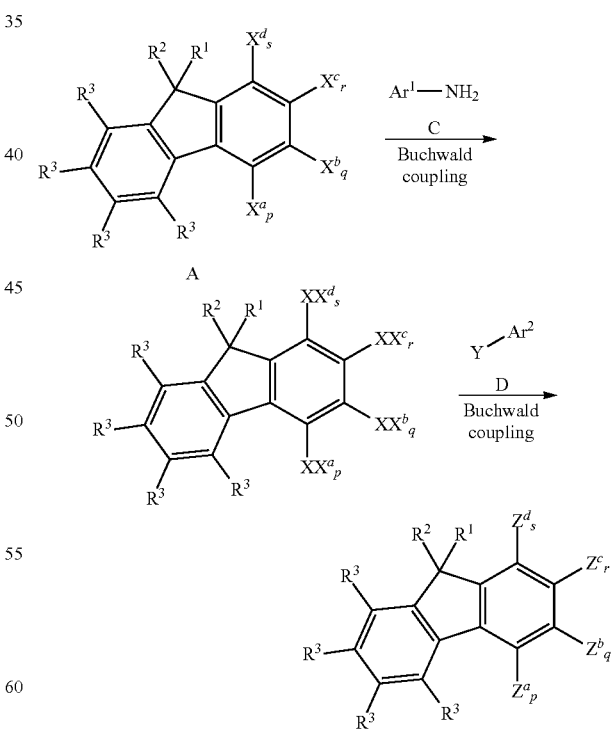

where Y is again a leaving group, for example halogen; and where $XX^a_0$, $XX^b_0$, $XX^c_0$, $XX^d_0$ are, identically or differently on each occurrence, equal to $R^3$ and $XX^a_1$, $XX^b_1$, $XX^c_1$, $XX^d_1$ are equal to -B—NH—$Ar^1$.

Synthetic routes for the starting compounds A, B, C and D which are employed in the synthesis of the compounds are familiar to the person skilled in the art. Furthermore, some explicit synthetic processes are described in detail in the working examples.

Preferred coupling reactions for the preparation of the compounds of the general formula (1) are Buchwald couplings.

Preferred compounds for electroluminescent devices are shown by way of example in the following table:

formula (149)

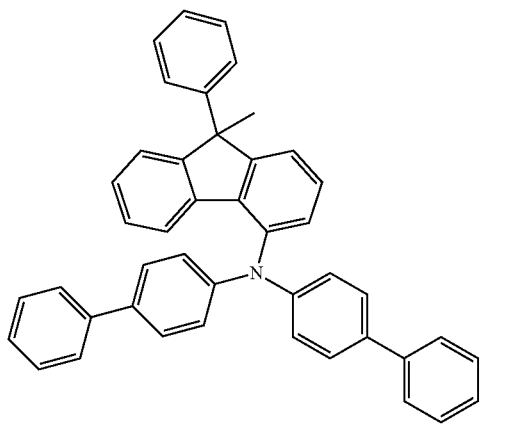

formula (150)

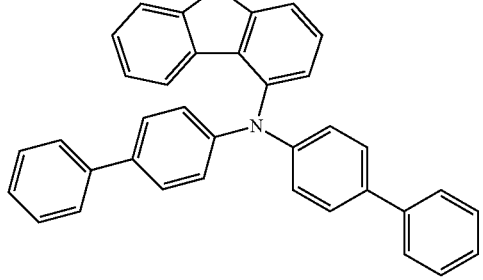

formula (151)

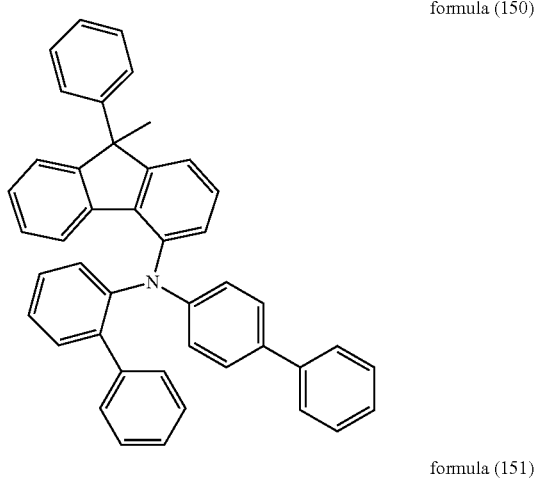

formula (152)

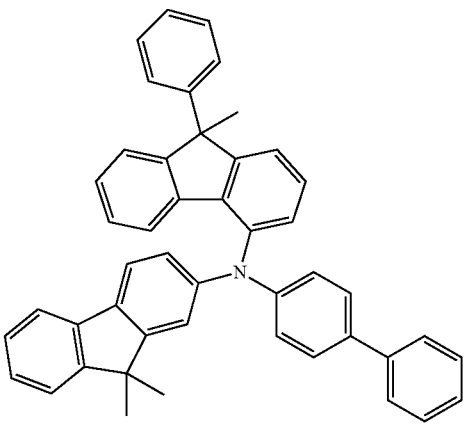

formula (153)

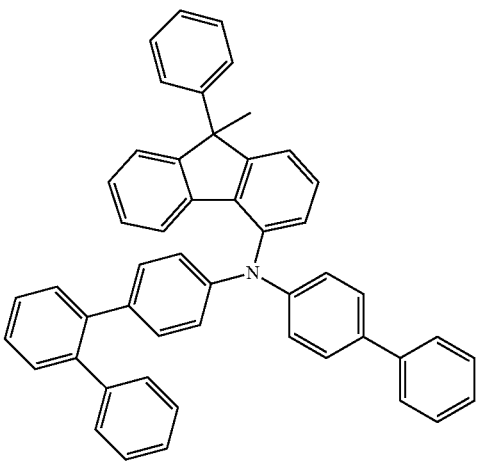

formula (154)

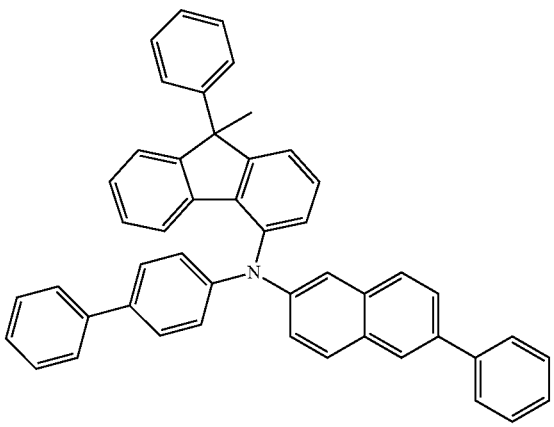

formula (155)
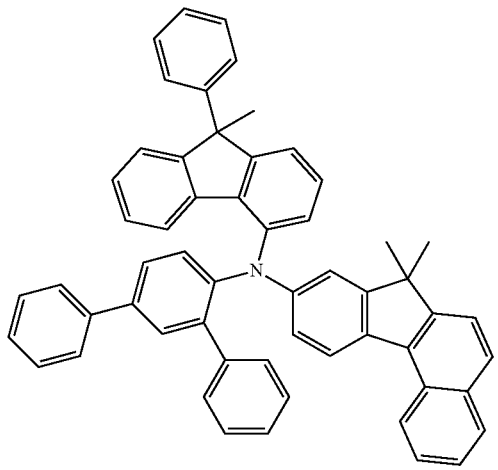
formula (156)
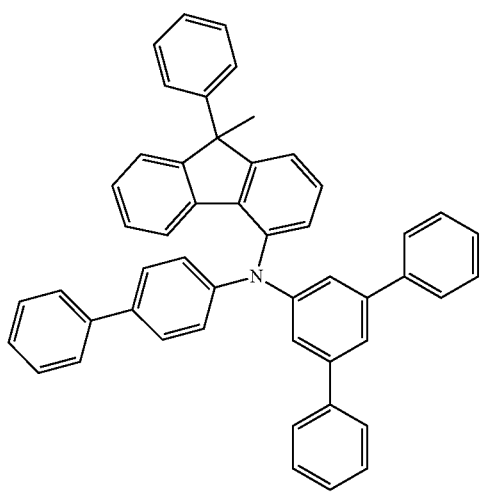
formula (157)
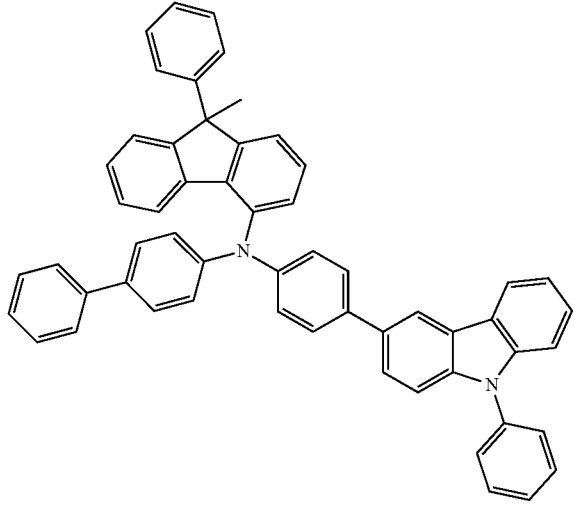
formula (158)
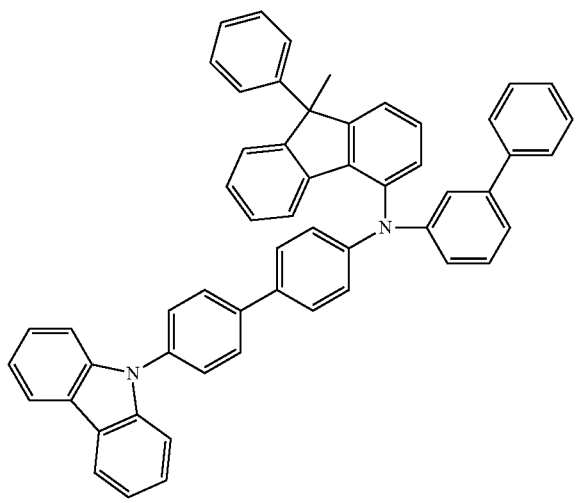
formula (159)
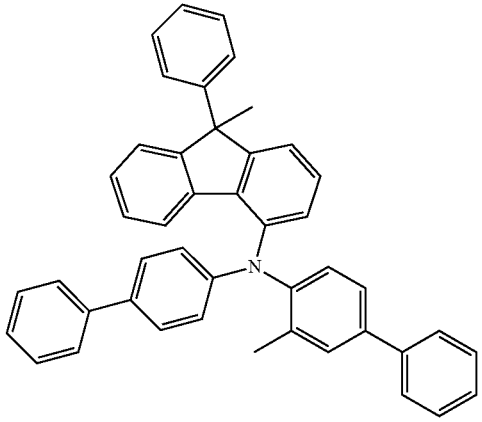
formula (160)
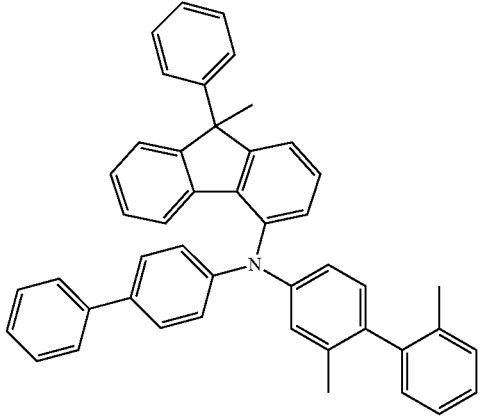

formula (161)
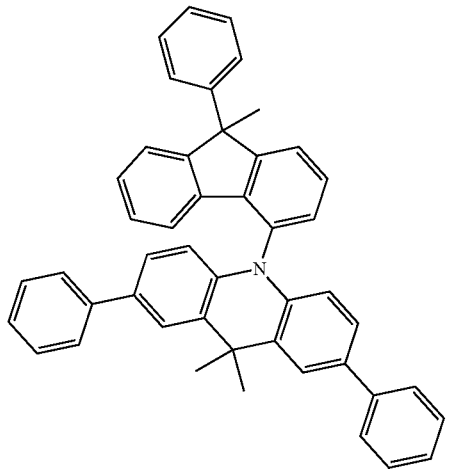
formula (162)
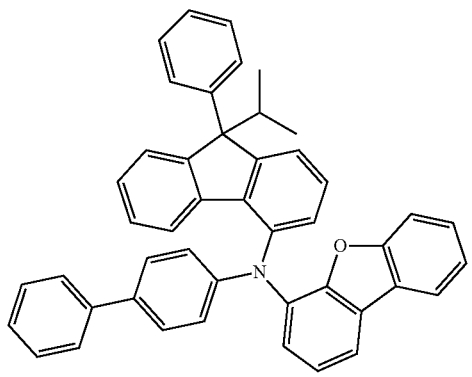
formula (163)
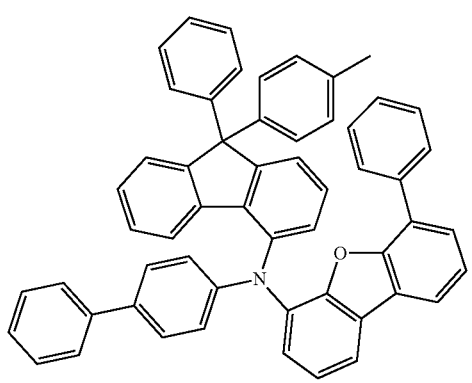
formula (164)
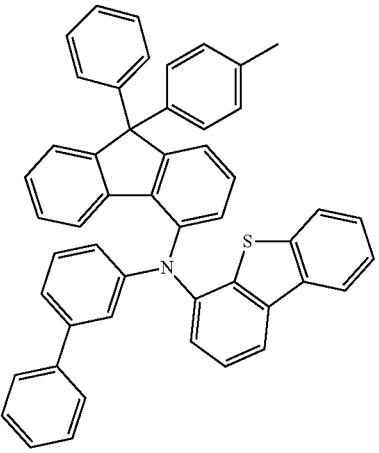
formula (165)
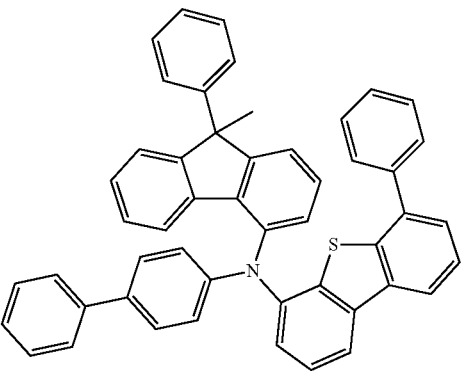
formula (166)
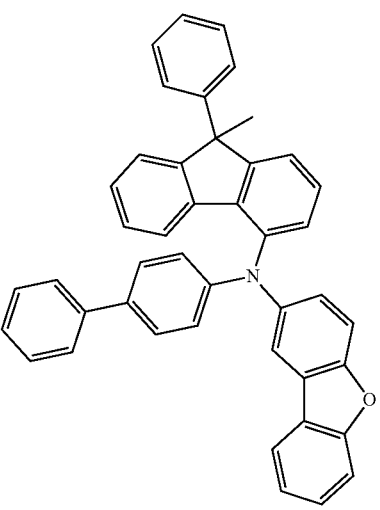

formula (167)
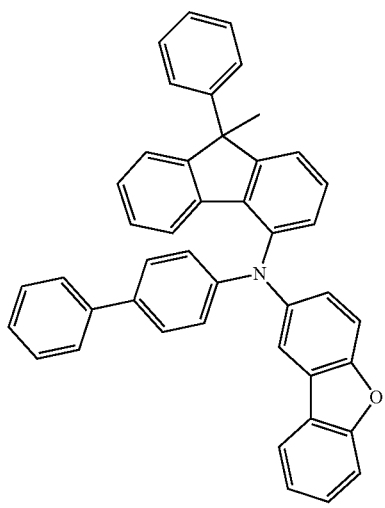
formula (168)
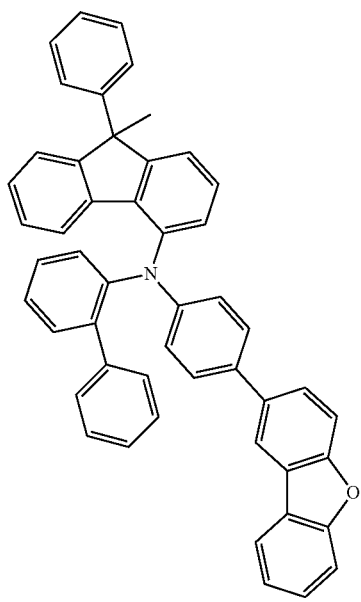
formula (169)
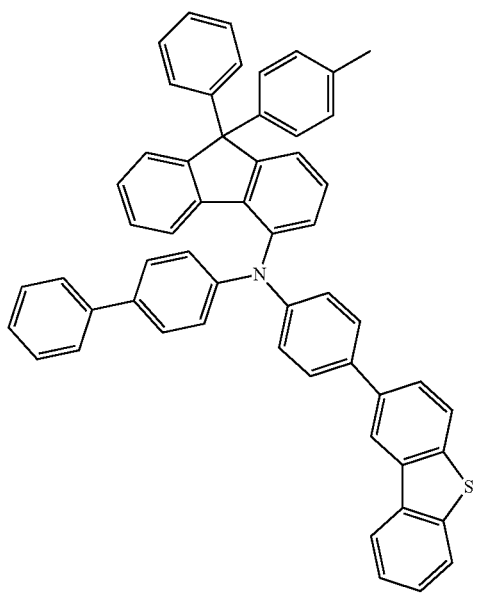
formula (170)
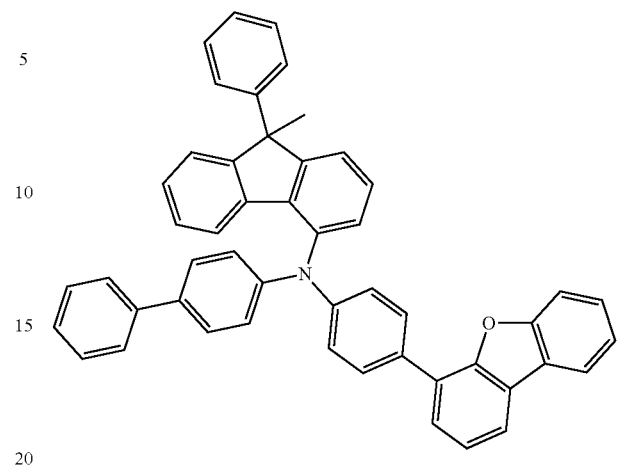
formula (171)
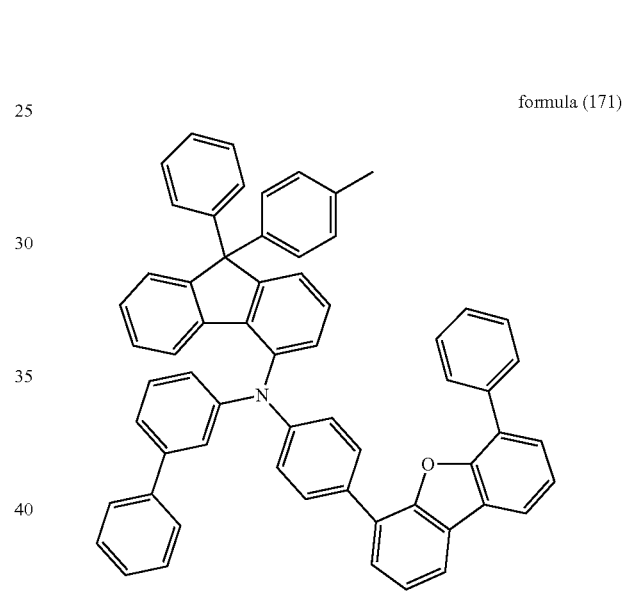
formula (172)
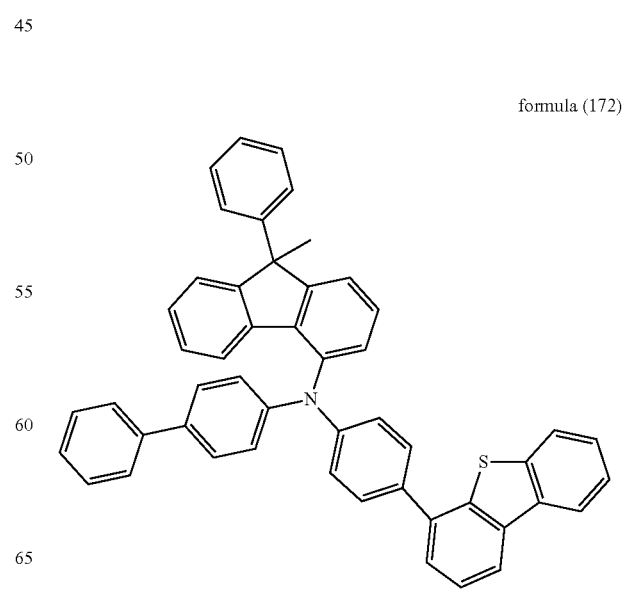

formula (173)
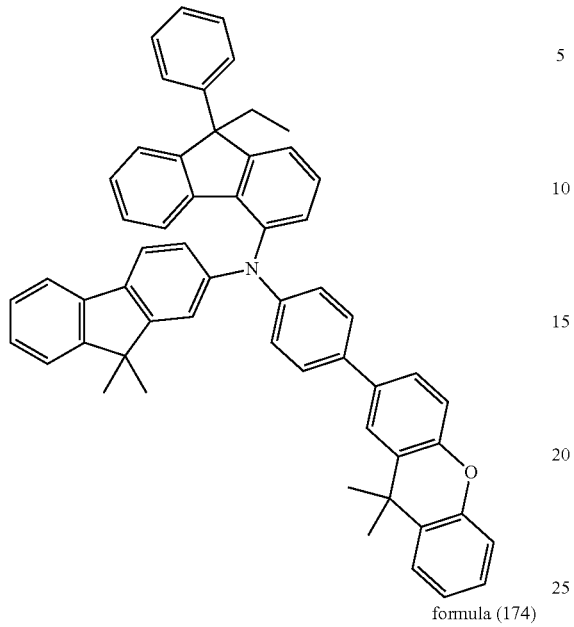
formula (174)
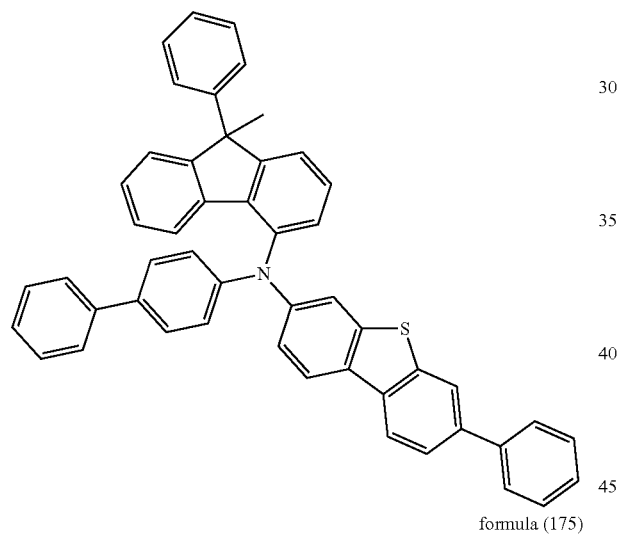
formula (175)
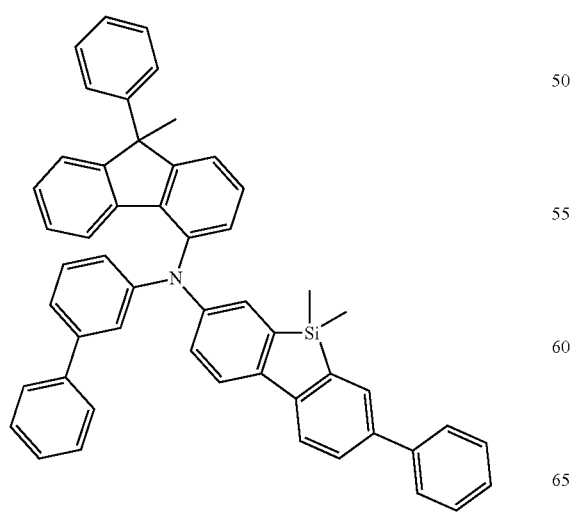
formula (176)
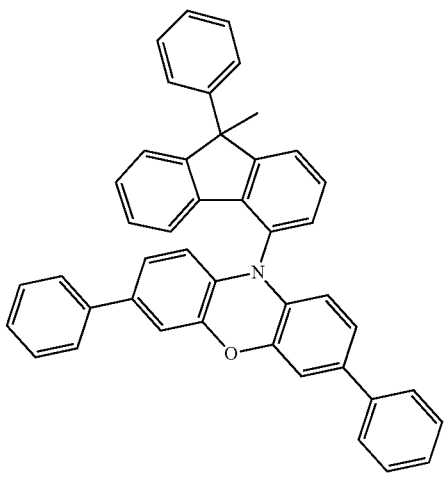
formula (177)
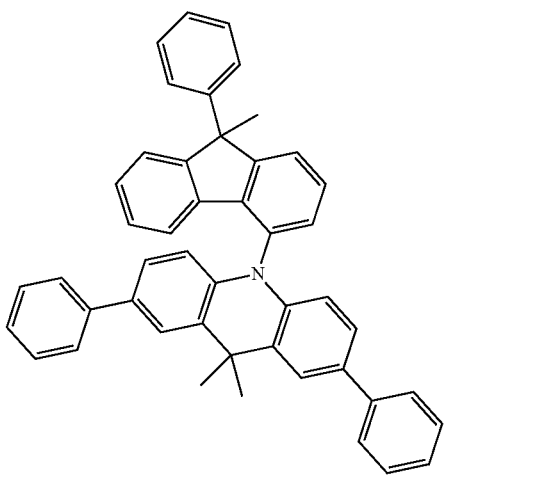
formula (178)
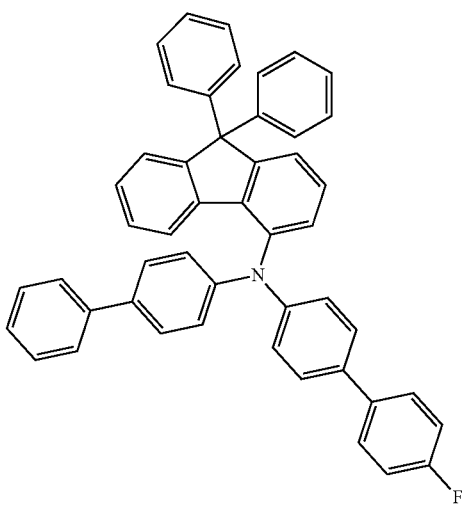

formula (179)
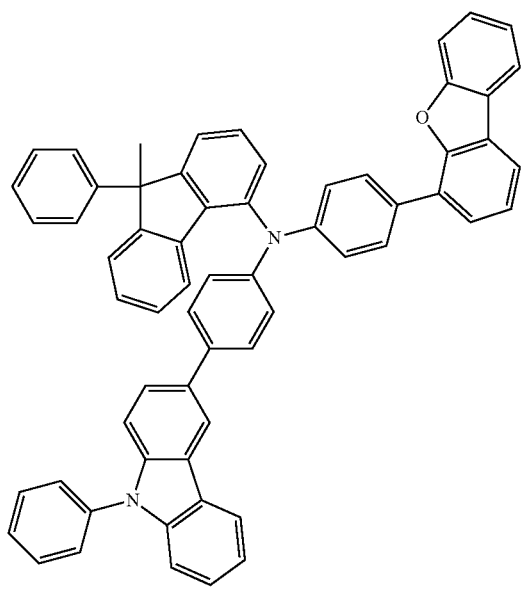
formula (180)
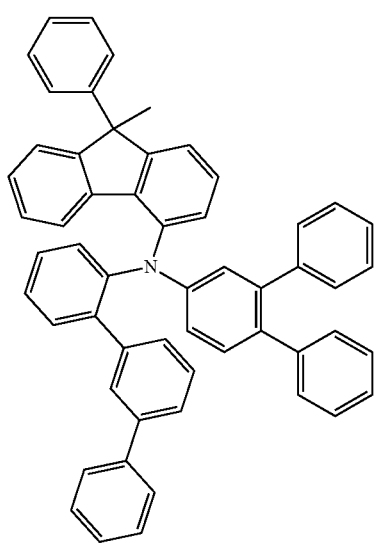
formula (181)
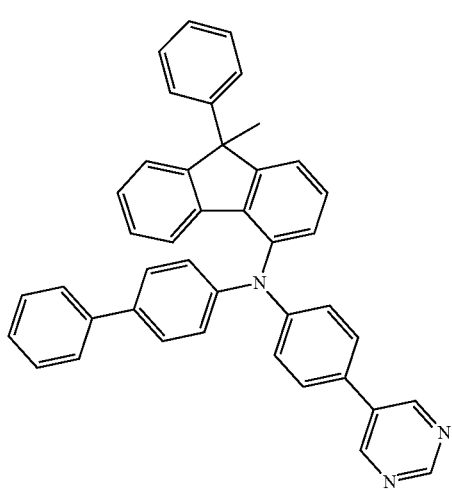
formula (182)
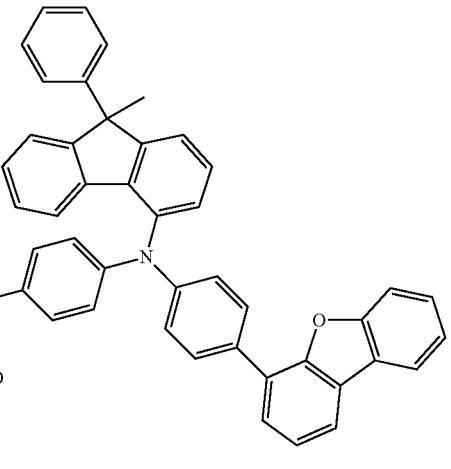
formula (183)
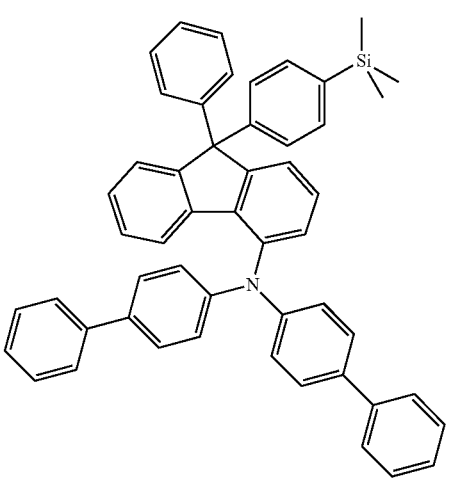
formula (184)
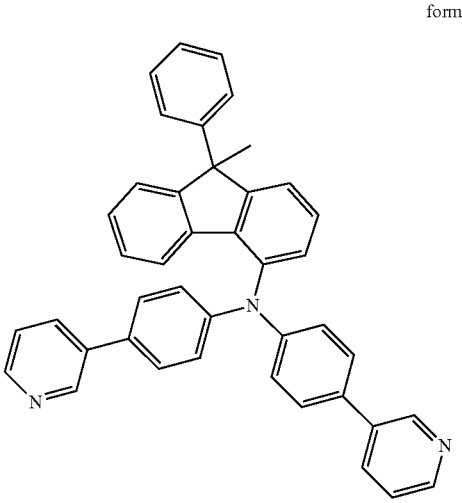

formula (185)
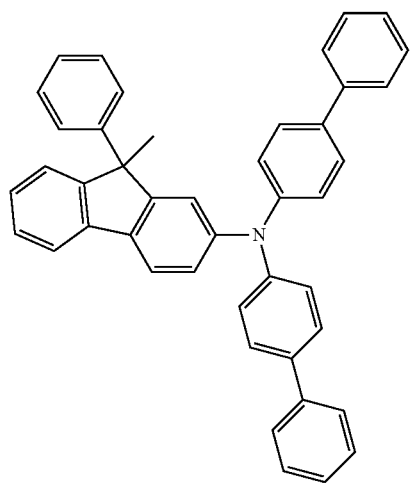
formula (186)
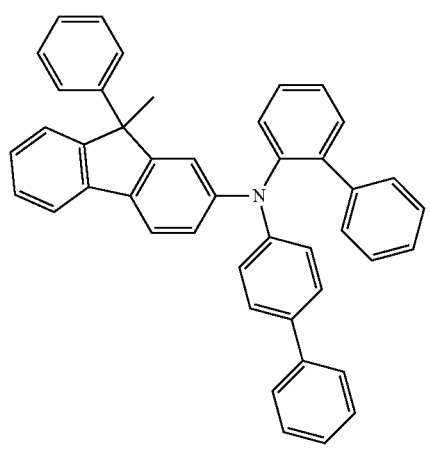
formula (187)
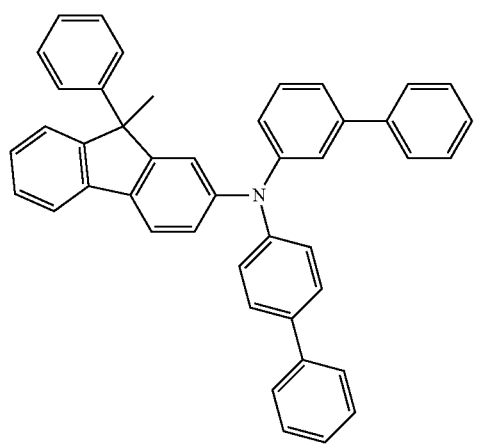
formula (188)
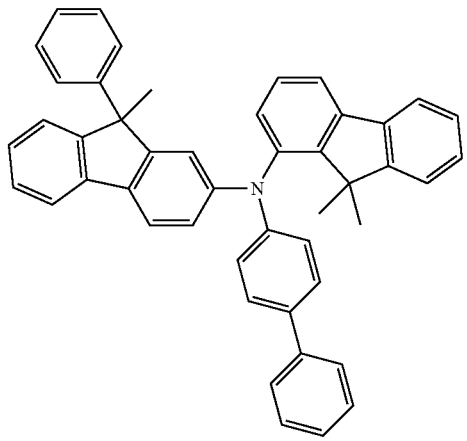
formula (189)
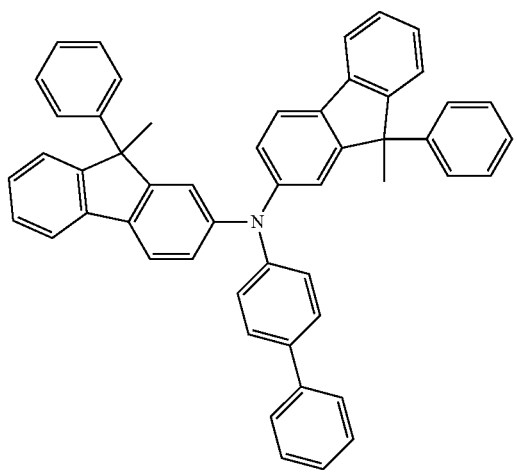
formula (190)
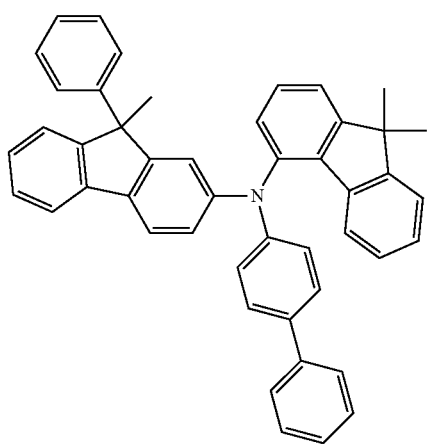

formula (191)
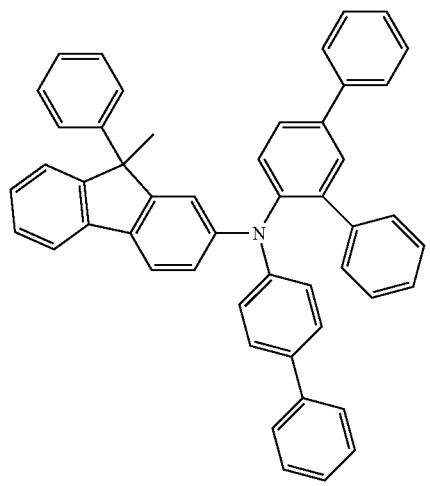
formula (192)
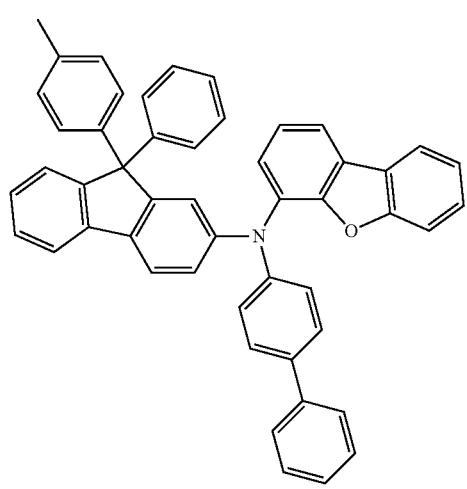
formula (193)
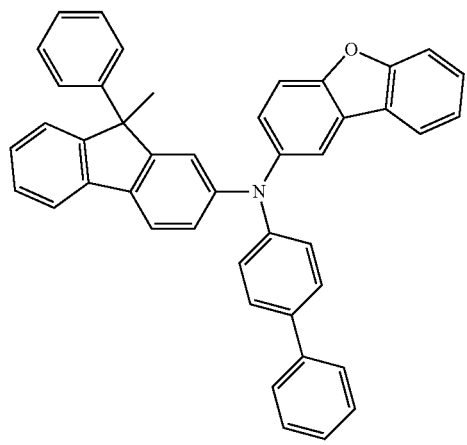
formula (194)
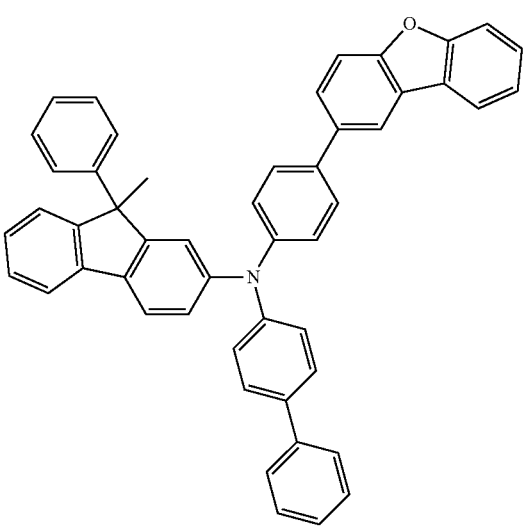
formula (195)
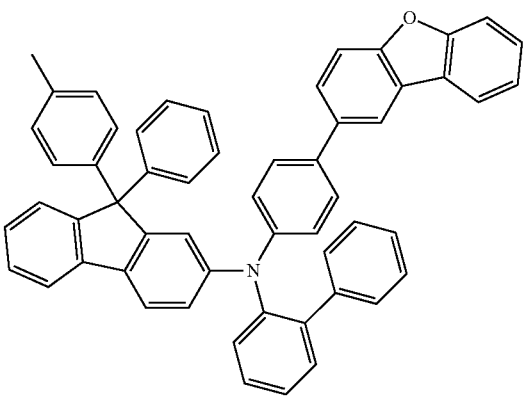
formula (196)
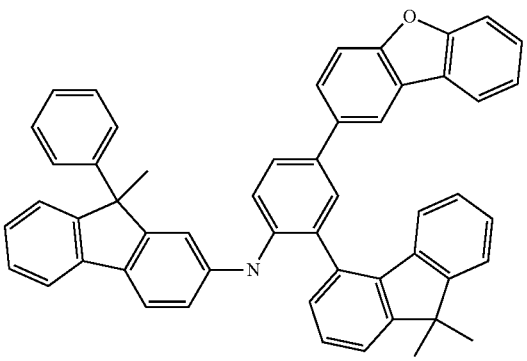

formula (197)
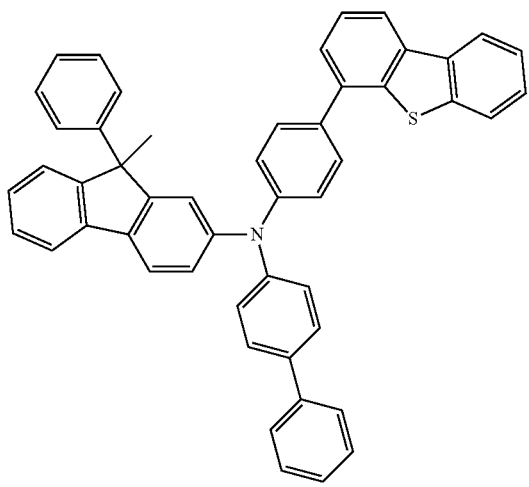
formula (200)
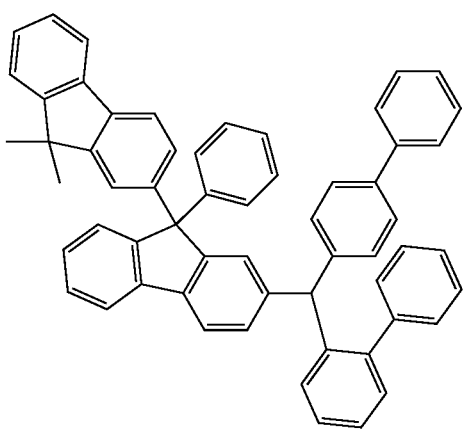
formual (198)
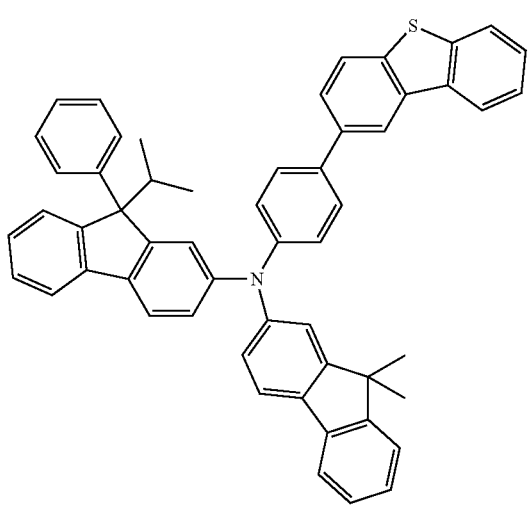
formula (201)
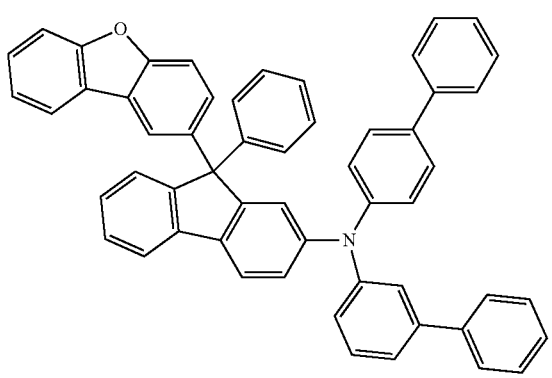
formula (199)
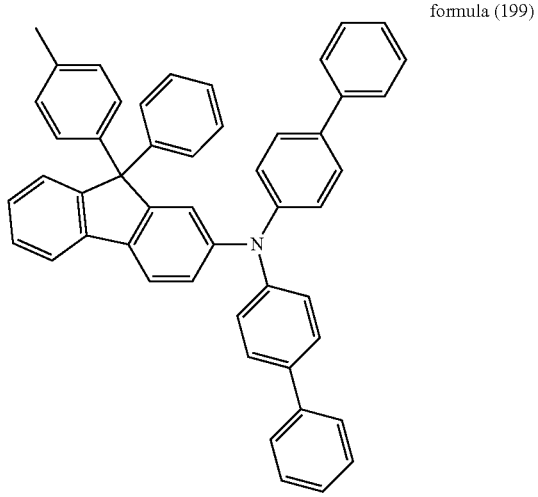
formual (202)
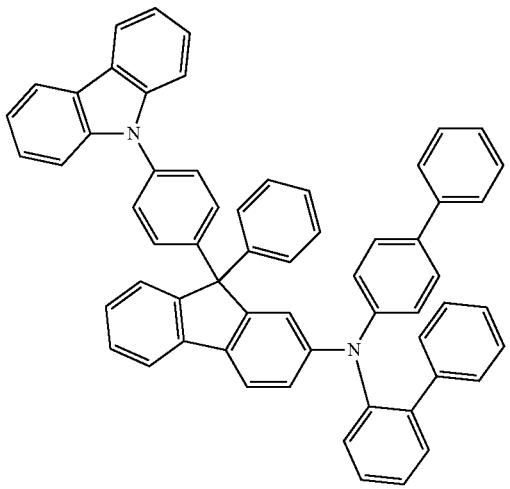

formula (203)
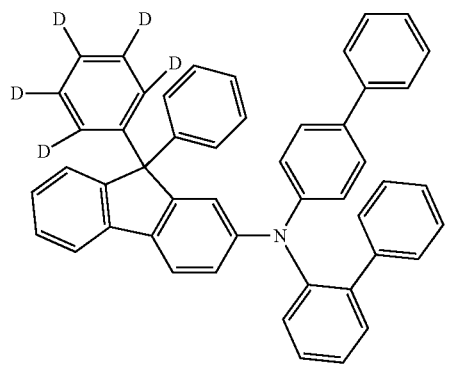
formula (204)
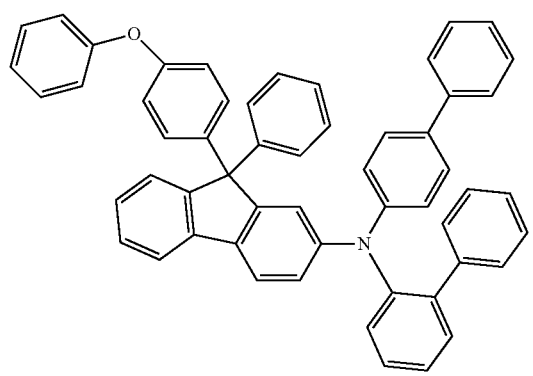
formula (205)
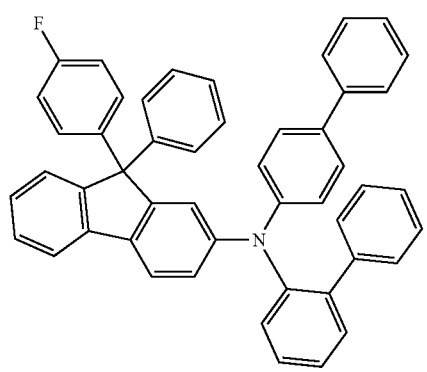
formula (206)
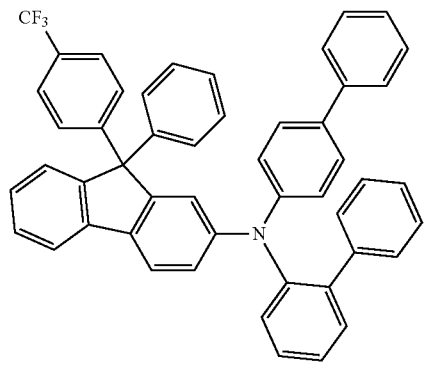
formula (207)
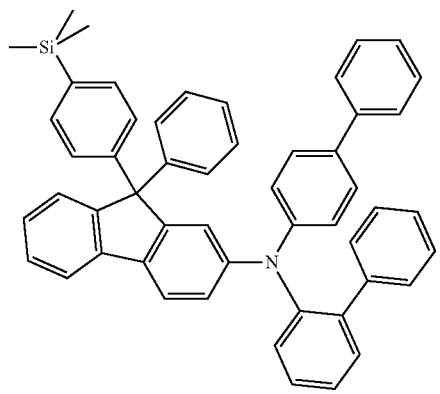
formula (208)
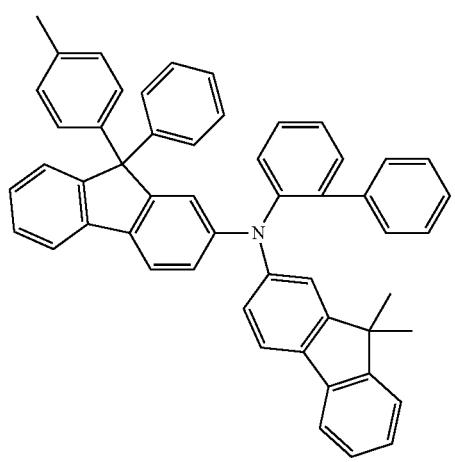
formula (209)
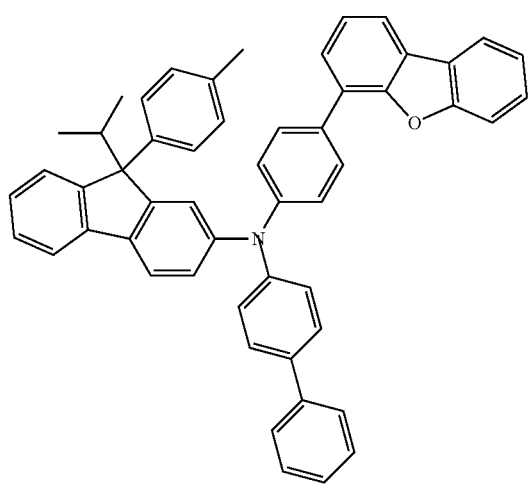

formula (210)
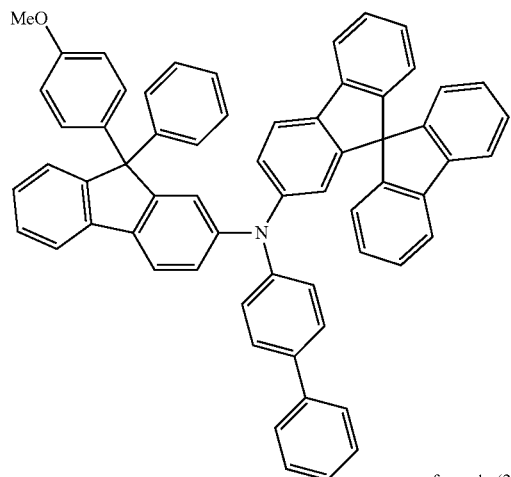
formula (211)
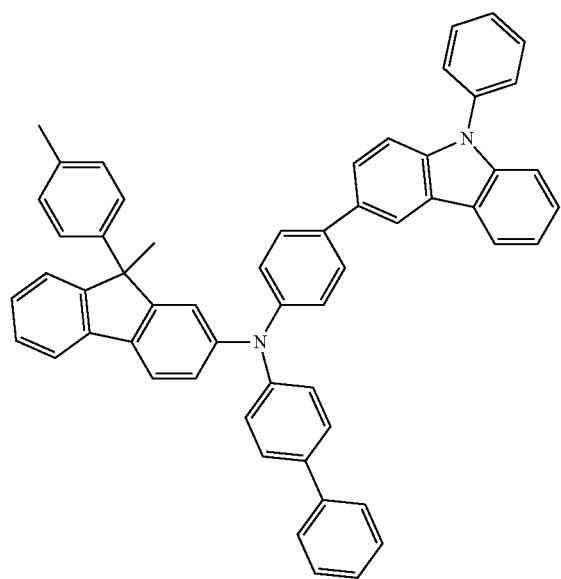
formula (212)
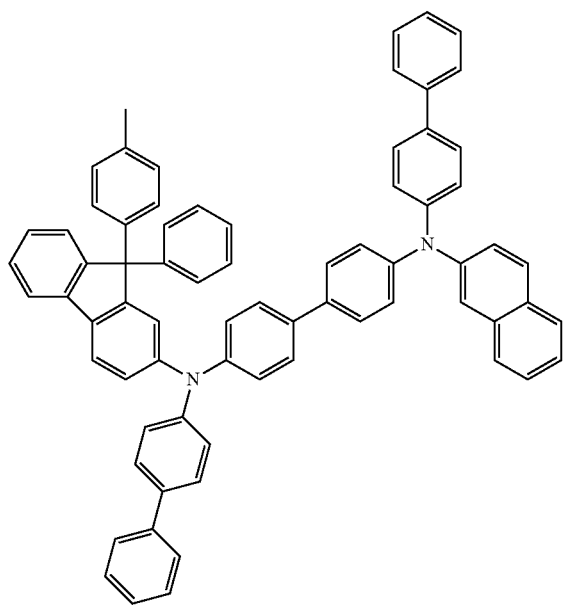
formula (213)
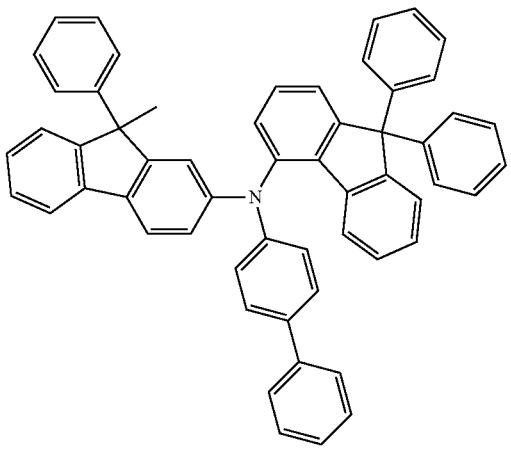
formula (214)
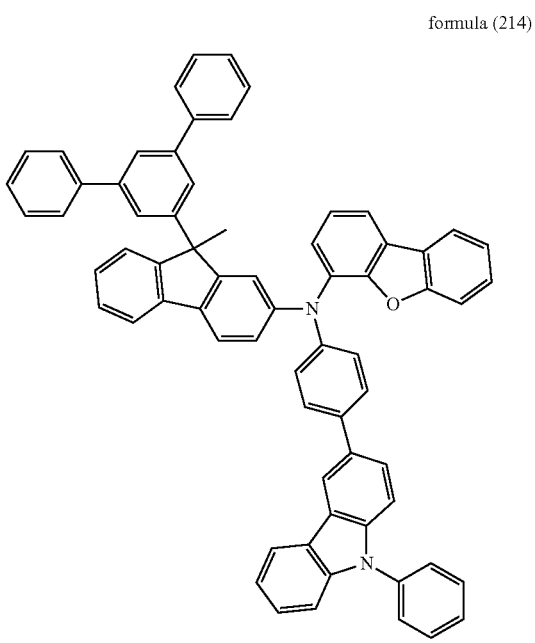
formula (215)
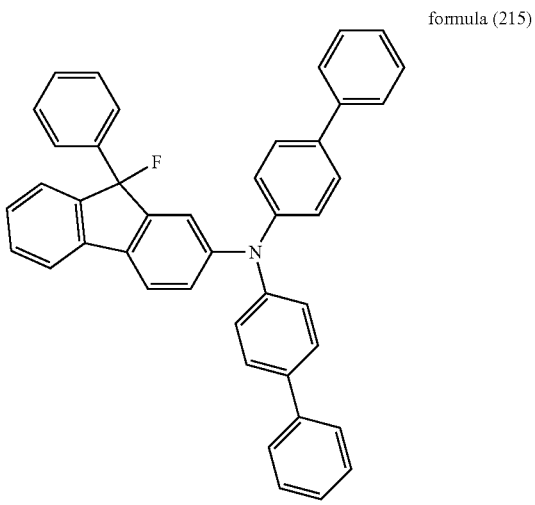

formula (216)
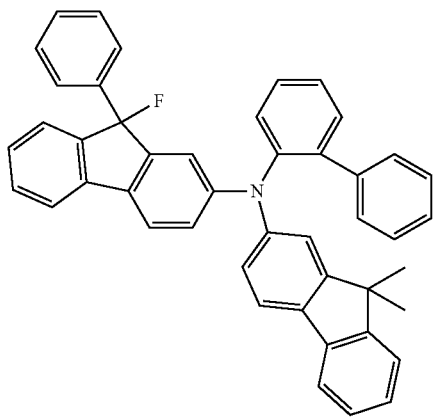
formula (217)
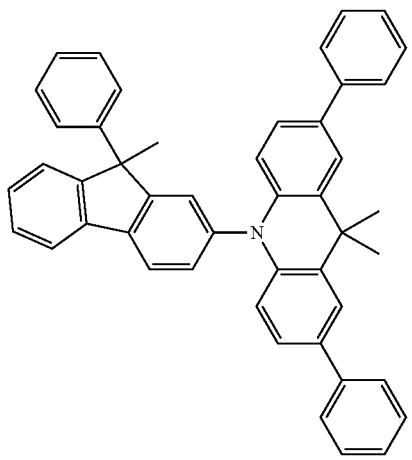
formula (218)
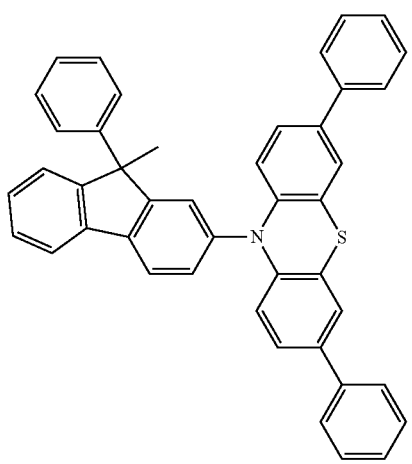
formula (219)
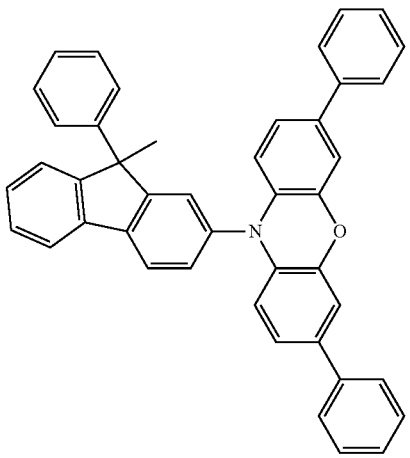
formula (220)
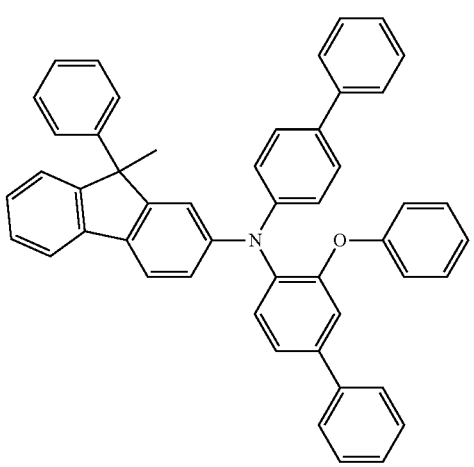
formula (221)
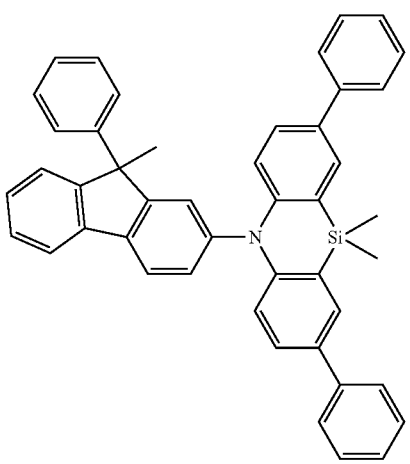

formula (222)
formula (223)
formula (224)
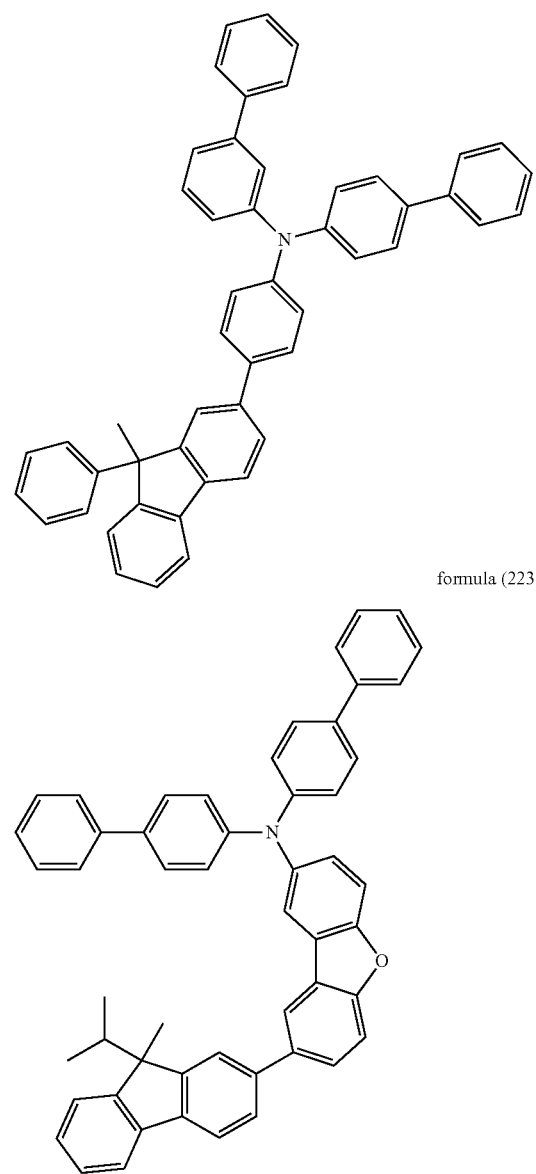
formula (225)
formula (226)
formula (227)
formula (228)
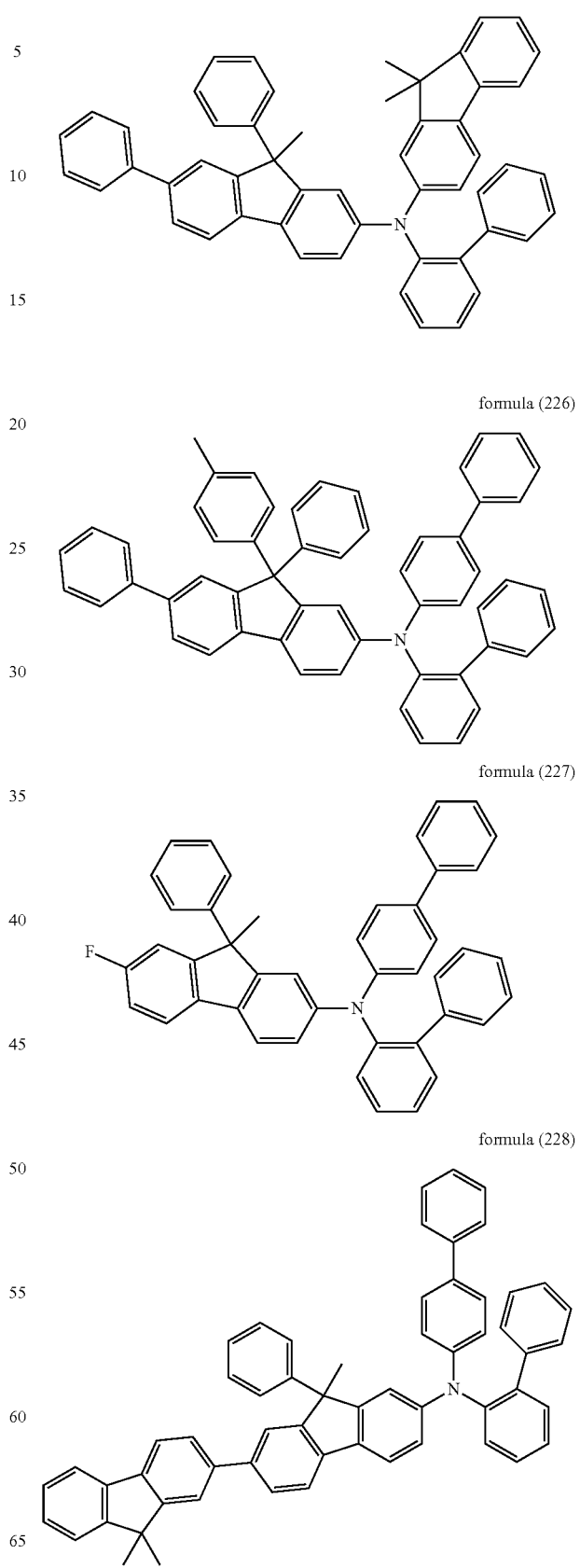

formula (229)
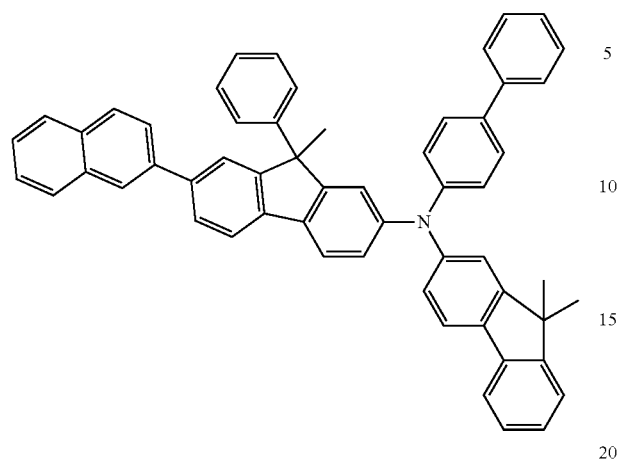
formula (230)
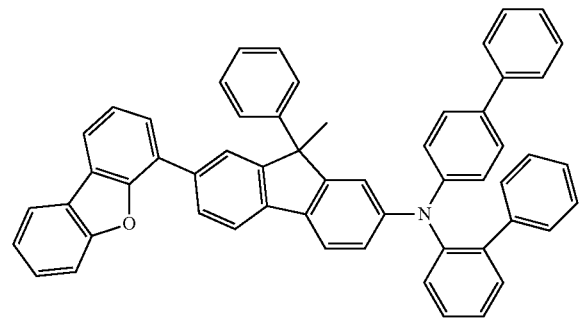
formula (231)
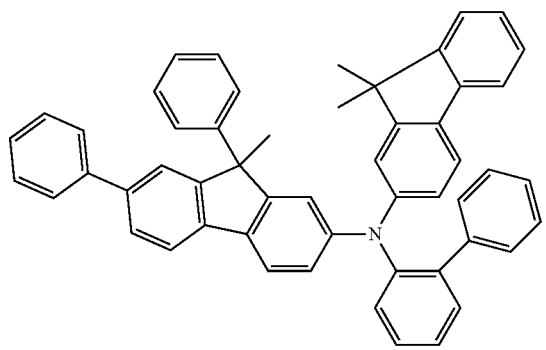
formula (232)
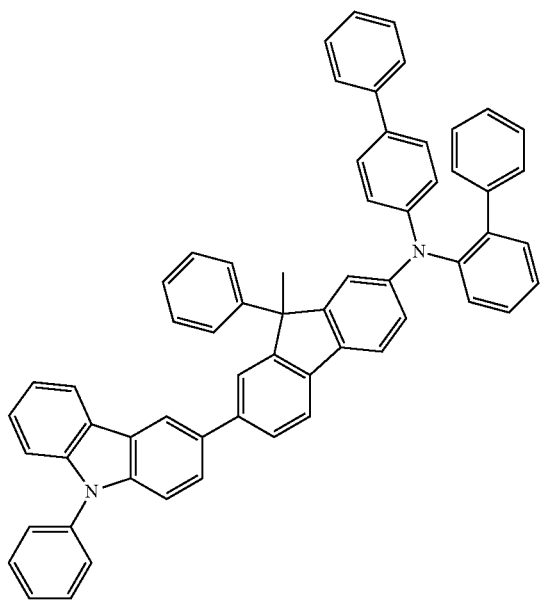
formula (233)
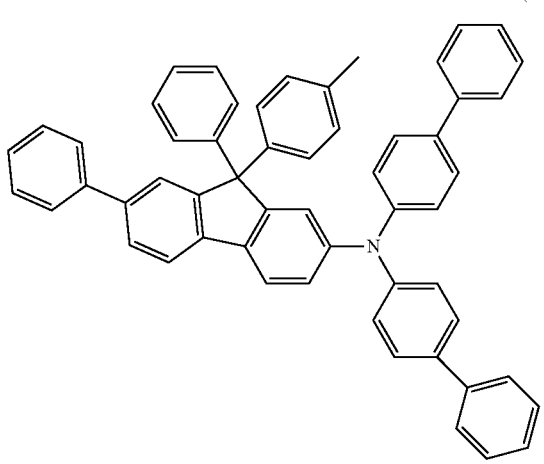
formula (234)
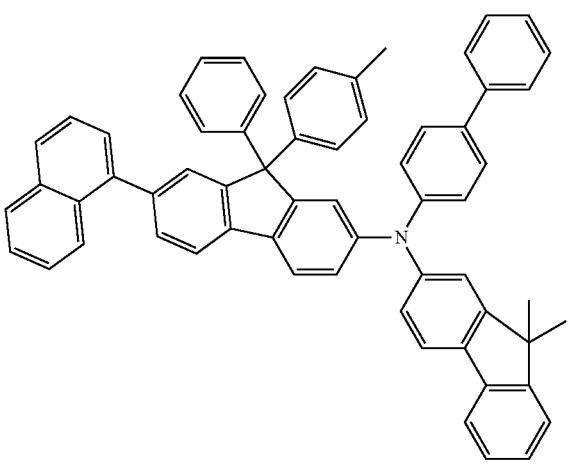

formula (235)
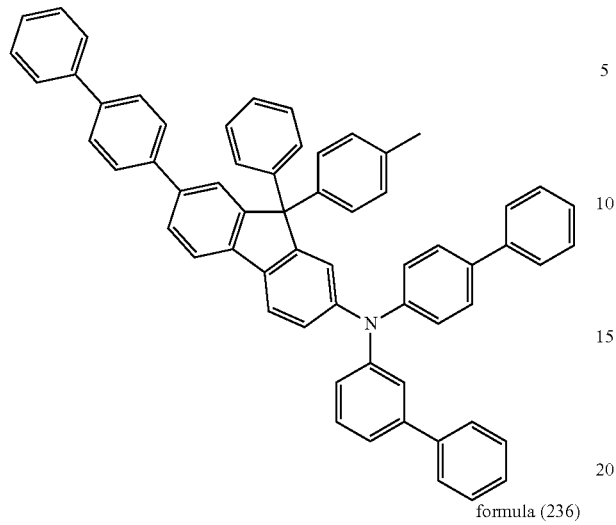
formula (236)
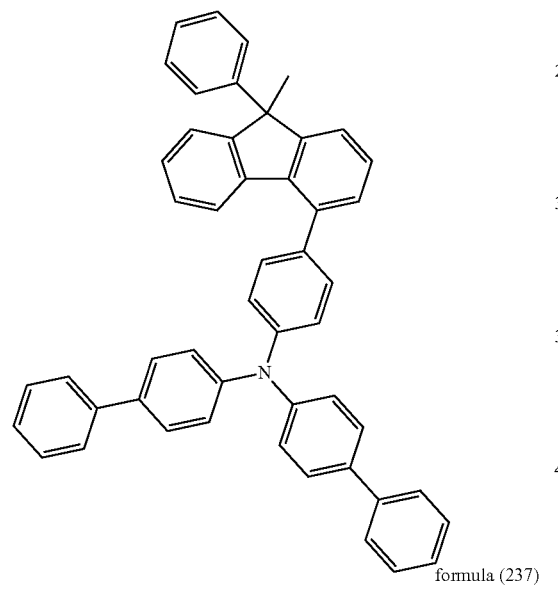
formula (237)
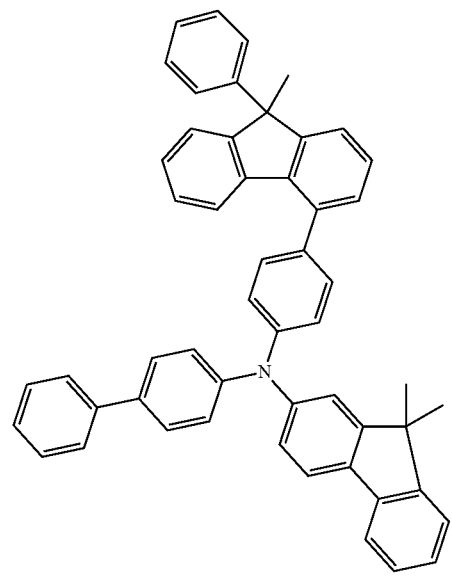
formula (238)
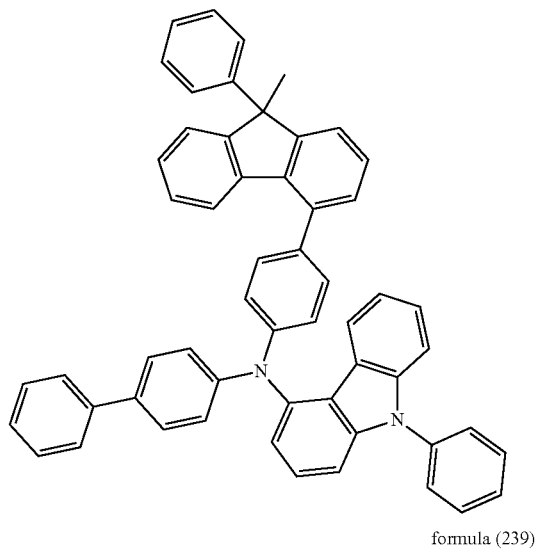
formula (239)
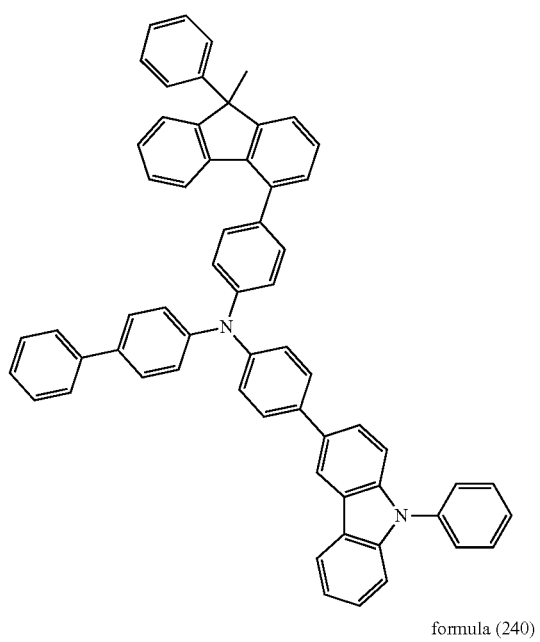
formula (240)
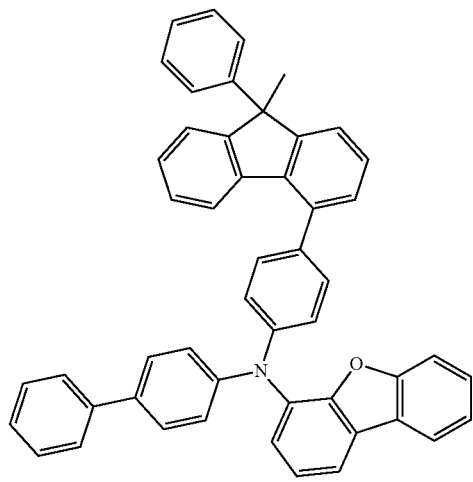

formula (241)
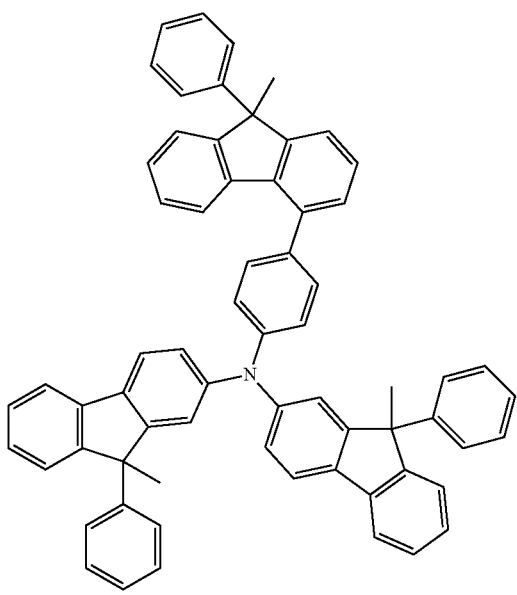
formula (242)
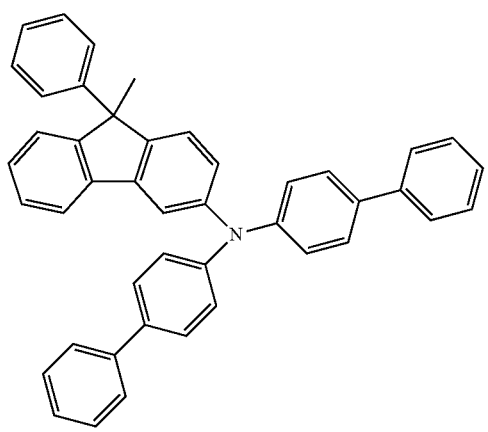
formula (243)
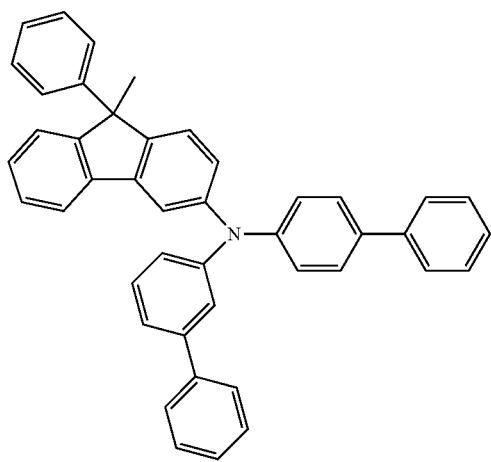
formula (244)
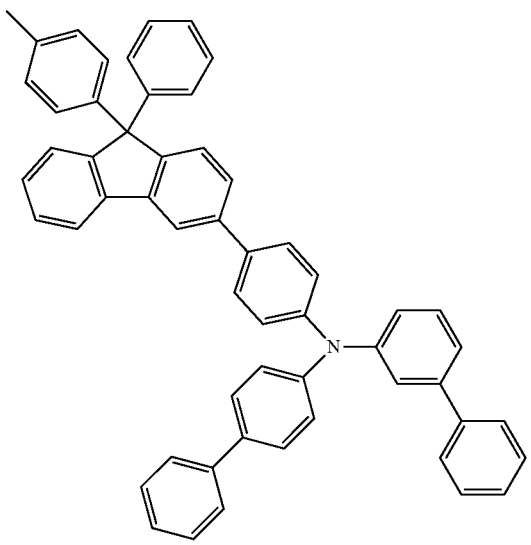
formula (245)
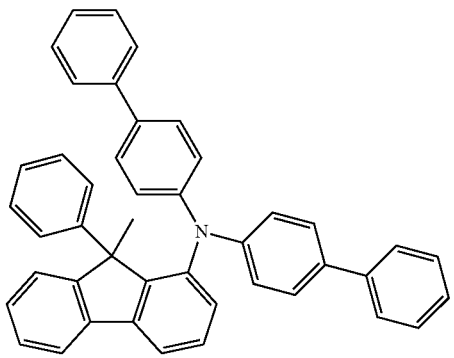
formula (246)
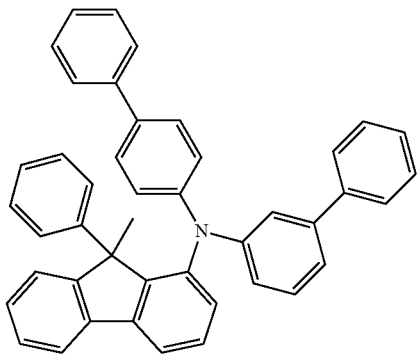

formula (247)
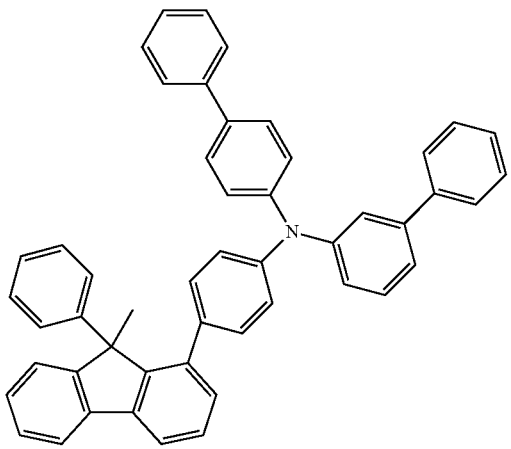
formula (248)
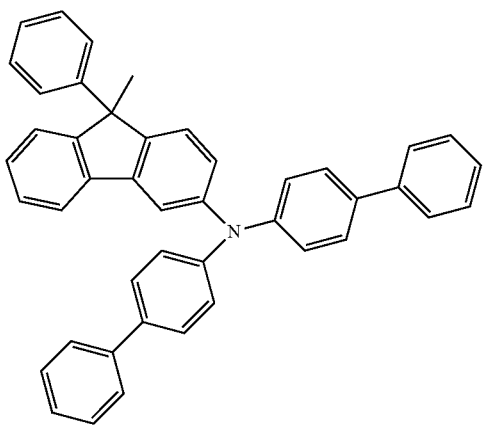
formula (249)
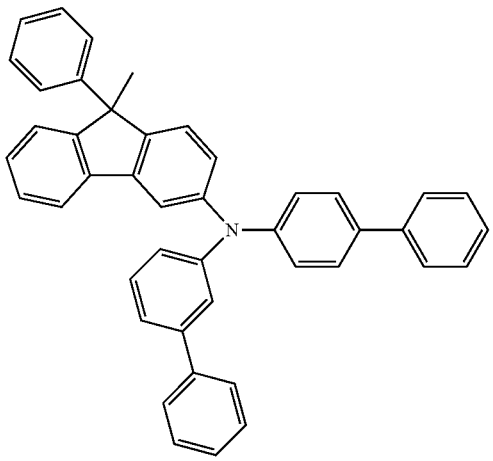
formula (250)
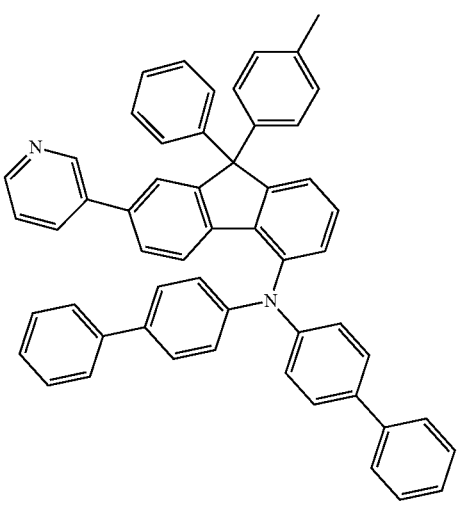
formula (251)
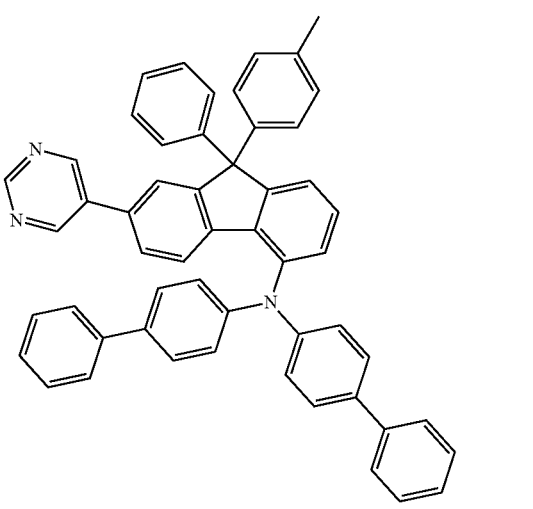
formula (252)
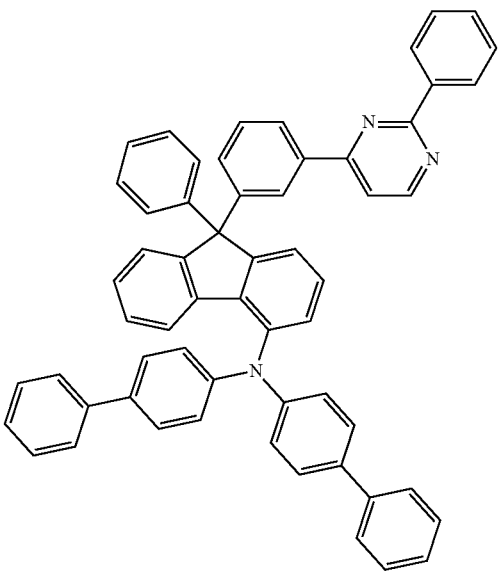

-continued formula (253)

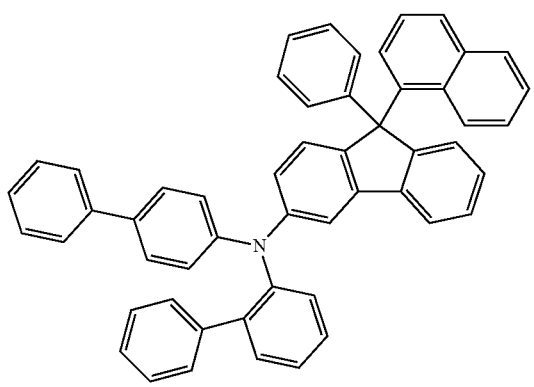

formula (254)

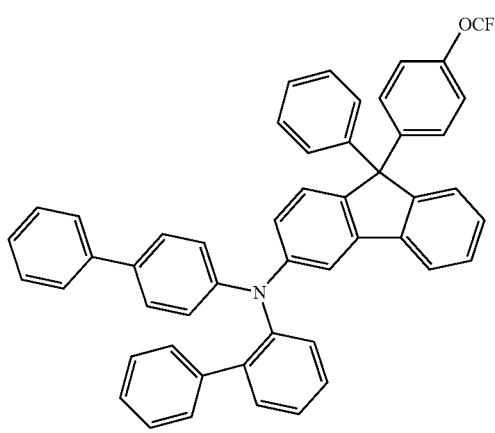

The present invention also relates to a compound of the general formula (255)

formula (255)

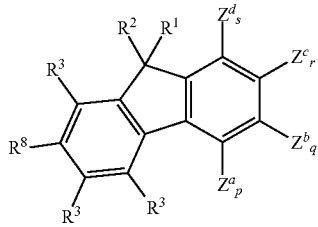

where the following applies to the symbols and indices used:

p, q, r, s
are 0 or 1, where p+q+r+s=1, preferably p=1 or r=1 or s=1 very preferably p=1 or r=1;

$Z^a_0$, $Z^b_0$, $Z^c_0$, $Z^d_0$
are, identically or differently on each occurrence, equal to $R^4$ $Z^a_1$, $Z^b_1$, $Z^c_1$, $Z^d_1$ are equal to

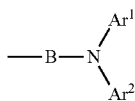

B is a single bond, a divalent aryl group having 6 to 30 ring atoms or a divalent heteroaryl group having 5 to 30 ring atoms, each of which may be substituted by one or more radicals $R^6$,
preferably a single bond or a phenylene, biphenylene, terphenylene, naphthylene, pyridinylene, pyrimidinylene, pyrazinylene, pyridazinylene, triazinylene, dibenzofuranylene, dibenzothiophenylene fluorenylene, or carbazoylene group, which may be substituted by one or more radicals $R^6$,
very preferably a single bond or a phenylene, biphenylene, terphenylene, naphthylene, dibenzofuranylene or dibenzothiophenylene fluorenylene, or carbazoylene group, which may be substituted by one or more radicals $R^6$,
B is very particularly preferably a single bond or a phenylene group, which may be substituted by one or more radicals $R^6$,
B is especially preferably a single bond,
where, if B is a single bond, the nitrogen atom is bonded directly to the fluorene;
$Ar^1$, $Ar^2$
are on each occurrence, identically or differently, an uncondensed aryl group having 10 to 60 ring atoms or a heteroaryl group 10 to 60 ring atoms, which may be substituted by one or more radicals $R^5$, which are identical to or different from one another, where both groups $Ar^1$ or $Ar^2$ each contain at least two or more aromatic or heteroaromatic rings,
where two of the aromatic or heteroaromatic rings in $Ar^1$ may be bridged by a divalent group —O—, —S—, —Si($R^5$)$_2$—, —C($R^5$)$_2$— or —$NR^5$— or two of the aromatic or heteroaromatic rings in $Ar^2$ may be bridged by a divalent group —O—, —S—, —Si($R^5$)$_2$—, —C($R^5$)$_2$— or —$NR^5$—, where unbridged rings are preferred
and where an aromatic or heteroaromatic ring from $Ar^1$ may be bridged to an aromatic or heteroaromatic ring from $Ar^2$ by a divalent group —O—, —S—, —Si($R^5$)$_2$—, —$NR^5$— or —C($R^5$)$_2$—, where unbridged groups $Ar^1$ and $Ar^2$ are preferred;
$R^1$, $R^2$, $R^3$ and $R^4$
are H, D, F, Cl, Br, I, C(=O)$R^6$, CN, Si($R^6$)$_3$, NO$_2$, N($R^6$)$_2$, P(=O)($R^6$)$_2$, S(=O)$R^6$, S(=O)$_2R^6$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals $R^6$ and where one or more CH$_2$ groups in the above-mentioned groups may be replaced by —$R^6$C=CR$^6$—, —C≡C—, Si($R^6$)$_2$, C=O, C=S, C=NR$^6$, —C(=O)O—, —C(=O)NR$^6$—, P(=O)($R^6$), —O—, —S—, SO or SO$_2$ and where one or more H atoms in the above-mentioned groups may be replaced by D, F, Cl, Br, I, CN or NO$_2$, or an aromatic or heteroaromatic ring system having 6 to 30 aromatic ring atoms, which may in each case be substituted by one or more radicals $R^6$, or an aryloxy group having 5 to 60 aromatic ring atoms, which may be substituted by one or more radicals $R^6$, or an aralkyl group having 5 to 60 aromatic ring atoms, which may in each case be substituted by one or more radicals $R^6$,
where the radicals $R^1$ and $R^2$ cannot be identical and the radicals $R^3$ to $R^5$ may on each occurrence be identical or different, but may be identical to either $R^1$ or to $R^2$ and where at least one of the radicals from $R^1$ and $R^2$ represents an aromatic or heteroaromatic ring system having 6 to 30 aromatic ring atoms, which may in each case be substituted by one or more radicals $R^6$;

$R^5$
is H, D, C(=O)$R^6$, CN, Si($R^6$)$_3$, NO$_2$, N($R^6$)$_2$, P(=O)($R^6$)$_2$, S(=O)$R^6$, S(=O)$_2R^6$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals $R^6$ and where one or more CH$_2$ groups in the above-mentioned groups may be replaced by —$R^6$C=C$R^6$—, —C≡C—, Si($R^6$)$_2$, C=O, C=S, C=N$R^6$, —C(=O)O—, —C(=O)N$R^6$—, P(=O)($R^6$), —O—, —S—, SO or SO$_2$ and where one or more H atoms in the above-mentioned groups may be replaced by D, F, Cl, Br, I, CN or NO$_2$, or an aromatic or heteroaromatic ring system having 6 to 30 aromatic ring atoms, which may in each case be substituted by one or more radicals $R^6$, or an aryloxy group having 5 to 60 aromatic ring atoms, which may be substituted by one or more radicals $R^6$, or an aralkyl group having 5 to 60 aromatic ring atoms, which may in each case be substituted by one or more radicals $R^6$, $R^6$ is on each occurrence, identically or differently, H, D, F, Cl, Br, I, C(=O)$R^7$, CN, Si($R^7$)$_3$, NO$_2$, P(=O)($R^7$)$_2$, S(=O)$R^7$, S(=O)$_2R^7$, N($R^7$)$_2$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals $R^7$ and where one or more CH$_2$ groups in the above-mentioned groups may be replaced by —$R^7$C=C$R^7$—, —C≡C—, Si($R^7$)$_2$, C=O, C=S, C=N$R^7$, —C(=O)O—, —C(=O)N$R^7$—, P(=O)($R^7$), —O—, —S—, SO or SO$_2$ and where one or more H atoms in the above-mentioned groups may be replaced by D, F, Cl, Br, I, CN or NO$_2$, or an aromatic or heteroaromatic ring system having 5 to 30 aromatic ring atoms, which may in each case be substituted by one or more radicals $R^7$, or an aryloxy or heteroaryloxy group having 5 to 30 aromatic ring atoms, which may be substituted by one or more radicals $R^7$, where two or more adjacent substituents $R^6$ may form a mono- or polycyclic ring system with one another;

$R^7$ is selected from the group consisting of H, D, F, an aliphatic hydrocarbon radical having 1 to 20 C atoms or an aromatic or heteroaromatic ring system having 5 to 30 C atoms, in which one or more H atoms may be replaced by D or F, where two or more adjacent substituents $R^7$ may form a mono- or polycyclic ring system with one another;

$R^8$
is H, D, C(=O)$R^9$, CN, Si($R^9$)$_3$, NO$_2$, N($R^9$)$_2$, P(=O)($R^9$)$_2$, S(=O)$R^9$, S(=O)$_2R^9$, a straight-chain alkyl or thioalkyl group having 1 to 20 C atoms or a branched or cyclic alkyl, alkoxy or thioalkyl group having 3 to 20 C atoms or an alkenyl or alkynyl group having 2 to 20 C atoms where the above-mentioned groups may each be substituted by one or more radicals $R^9$ and where one or more CH$_2$ groups in the above-mentioned groups may be replaced by —$R^9$C=C$R^9$—, —C≡C—, Si($R^9$)$_2$, C=O, C=S, C=N$R^9$, —C(=O)O—, —C(=O)N$R^9$—, P(=O)($R^9$), —S—, SO or SO$_2$ and where one or more H atoms in the above-mentioned groups may be replaced by D, F, Cl, Br, I, CN or NO$_2$, or an aromatic or heteroaromatic ring system having 6 to 30 aromatic ring atoms, which may in each case be substituted by one or more radicals $R^9$, or an aryloxy group having 5 to 60 aromatic ring atoms, which may be substituted by one or more radicals $R^9$, or an aralkyl group having 5 to 60 aromatic ring atoms, which may in each case be substituted by one or more radicals $R^9$;

$R^9$ is on each occurrence, identically or differently, H, D, F, Cl, Br, I, C(=O)$R^{10}$, CN, Si($R^{10}$)$_3$, NO$_2$, P(=O)($R^{10}$)$_2$, S(=O)$R^{10}$, S(=O)$_2R^{10}$, N($R^{10}$)$_2$, a straight-chain alkyl or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals $R^{10}$ and where one or more CH$_2$ groups in the above-mentioned groups may be replaced by —$R^{10}$C=C$R^{10}$—, —C≡C—, Si($R^{10}$)$_2$, C=O, C=S, C=N$R^{10}$, —C(=O)O—, —C(=O)N$R^{10}$—, P(=O)($R^{10}$, —S—, SO or SO$_2$ and where one or more H atoms in the above-mentioned groups may be replaced by D, F, Cl, Br, I, CN or NO$_2$, or an aromatic or heteroaromatic ring system having 5 to 30 aromatic ring atoms, which may in each case be substituted by one or more radicals $R^{10}$, or an aryloxy or heteroaryloxy group having 5 to 30 aromatic ring atoms, which may be substituted by one or more radicals $R^{10}$, where two or more adjacent substituents $R^{10}$ may form a mono- or polycyclic ring system with one another;

$R^{10}$ is selected from the group consisting of H, D, F, an aliphatic hydrocarbon radical having 1 to 20 C atoms or an aromatic or heteroaromatic ring system having 5 to 30 C atoms, in which one or more H atoms may be replaced by D or F, where two or more adjacent substituents $R^{10}$ may form a mono- or polycyclic ring system with one another.

In a preferred embodiment, the present invention relates to a compound of the general formula (255), characterised in that the compound contains no condensed aromatic or heteroaromatic ring systems having more than 10 ring atoms.

Preference is given to a compound of the general formula (256)

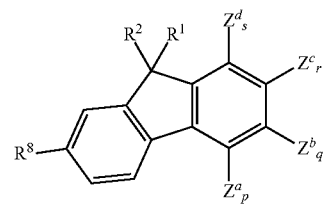

formula (256)

where the above definitions apply to the symbols used,

More preference is given to a compound of the general formulae (257) to (260)

formula (257)

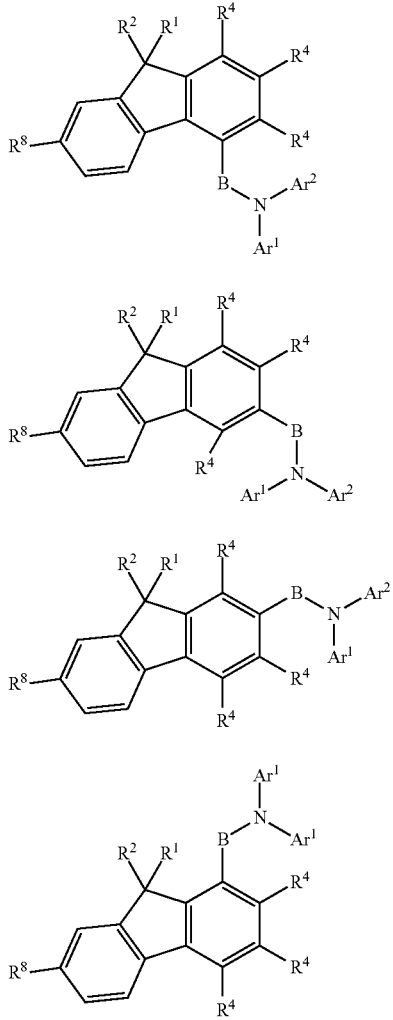

formula (258)

formula (259)

formula (260)

Very particular preference is given to a compound of the general formulae (261) to (264), where that of the formulae (261) and (263) is especially preferred.

formula (261)

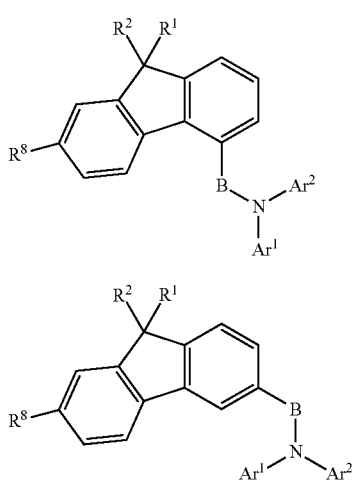

formula (262)

formula (263)

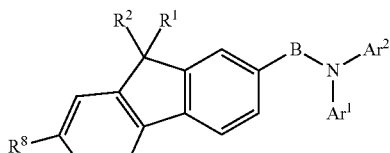

formula (264)

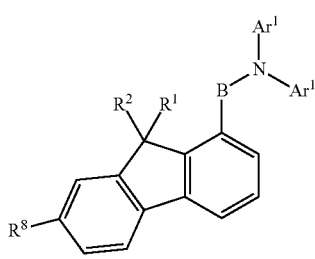

The above definitions apply to B and preferred embodiments of B.

Very particular preference is furthermore given to a compound of the general formulae (265) to (268), where that of the formulae (265) and (267) is especially preferred.

formula (265)

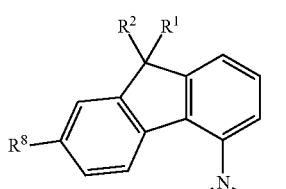

formula (266)

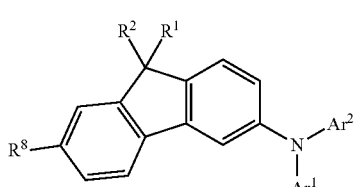

formula (267)

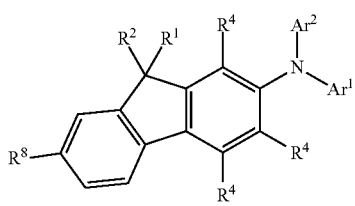

formula (268)

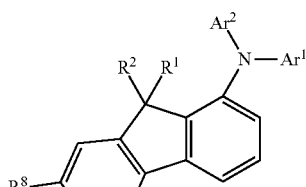

Ar¹ and Ar² are preferably selected, identically or differently on each occurrence, from a phenylpyridyl, biphenyl, terphenyl or quaterphenyl group, which may be substituted by one or more radicals R⁶, which may be identical to or different from one another, where two of the aromatic or heteroaromatic rings in Ar¹ may be bridged by a divalent group —O—, —S—, —Si($R^5$)$_2$—, —C($R^5$)$_2$— or $NR^5$ or two of the aromatic or heteroaromatic rings in $Ar^2$ may be bridged by a divalent group —O—, —S—, Si($R^5$)$_2$—, —C($R^5$)$_2$— or $NR^5$, where unbridged rings are preferred, and where an aromatic or heteroaromatic ring from $Ar^1$ may be bridged to an aromatic or heteroaromatic ring from $Ar^2$ by a divalent group —O—, —S—, —Si($R^5$)$_2$—, —$NR^5$— or —C($R^5$)$_2$—, where unbridged groups $Ar^1$ and $Ar^2$ are preferred.

The present invention furthermore relates to a process for the preparation of the compound of the formula (255), where, as described above, one-step or two-step Buchwald coupling is used.

Preferred examples of compounds according to the invention are those having the formulae (149) to (153), (155) to (177), (179) to (254).

The compounds of the formula (1) described above and the compounds of the formula (255) according to the invention may be substituted by reactive leaving groups, such as bromine, iodine, chlorine, boronic acid or boronic acid ester. These can be used as monomers for the production of corresponding oligomers, dendrimers or polymers. Suitable reactive leaving groups are, for example, bromine, iodine, chlorine, boronic acids, boronic acid esters, amines, alkenyl or alkynyl groups having a terminal C—C double bond or C—C triple bond, oxiranes, oxetanes, groups which undergo a cycloaddition, for example a 1,3-dipolar cycloaddition, such as, for example, dienes or azides, carboxylic acid derivatives, alcohols and silanes.

The invention therefore furthermore relates to oligomers, polymers or dendrimers containing one or more compounds of the formulae (1) or (255), where the bond(s) to the polymer, oligomer or dendrimer may be localised at any desired possible positions in the formulae (1) or (255). Depending on the linking of the compound of the formula (1) or (255), the compound is a constituent of a side chain of the oligomer or polymer or a constituent of the main chain. An oligomer in the sense of this invention is taken to mean a compound which is built up from at least three monomer units. A polymer in the sense of the invention is taken to mean a compound which is built up from at least ten monomer units. The polymers, oligomers or dendrimers according to the invention may be conjugated, partially conjugated or non-conjugated. The oligomers or polymers according to the invention may be linear, branched or dendritic. In the structures linked in a linear manner, the units of the formulae (1) or (255) may be linked directly to one another or they may be linked to one another via a divalent group, for example via a substituted or unsubstituted alkylene group, via a heteroatom or via a divalent aromatic or heteroaromatic group. In branched and dendritic structures, for example, three or more units of the formulae (1) or (255) may be linked via a trivalent or polyvalent group, for example via a trivalent or polyvalent aromatic or heteroaromatic group, to form a branched or dendritic oligomer or polymer.

The same preferences as described above for compounds of the formulae (1) or (255) apply to the recurring units of the formula (1) or (255) in oligomers, dendrimers and polymers.

For the preparation of the oligomers or polymers, the corresponding monomers are homopolymerised or copolymerised with further monomers. Suitable and preferred comonomers are selected from fluorenes (for example in accordance with EP 842208 or WO 2000/22026), spirobifluorenes (for example in accordance with EP 707020, EP 894107 or WO 2006/061181), paraphenylenes (for example in accordance with WO 1992/18552), carbazoles (for example in accordance with WO 2004/070772 or WO 2004/113468), thiophenes (for example in accordance with EP 1028136), dihydrophenanthrenes (for example in accordance with WO 2005/014689 or WO 2007/006383), cis- and trans-indenofluorenes (for example in accordance with WO 2004/041901 or WO 2004/113412), ketones (for example in accordance with WO 2005/040302), phenanthrenes (for example in accordance with WO 2005/104264 or WO 2007/017066) or also a plurality of these units. The polymers, oligomers and dendrimers usually also contain further units, for example emitting (fluorescent or phosphorescent) units, such as, for example, vinyltriarylamines (for example in accordance with WO 2007/068325) or phosphorescent metal complexes (for example in accordance with WO 2006/003000), and/or charge-transport units, in particular those based on triarylamines.

The polymers, oligomers and dendrimers according to the invention have advantageous properties, in particular long lifetimes, high efficiencies and good colour coordinates.

The polymers and oligomers according to the invention are generally prepared by polymerisation of one or more types of monomer, at least one monomer of which results in recurring units of the formula (1) or (255) in the polymer.

Suitable polymerisation reactions are known to the person skilled in the art and are described in the literature. Particularly suitable and preferred polymerisation reactions which result in C—C or C—N links are the following:

(A) SUZUKI polymerisation;
(B) YAMAMOTO polymerisation;
(C) STILLE polymerisation; and
(D) HARTWIG-BUCHWALD polymerisation.

The way in which the polymerisation can be carried out by these methods and the way in which the polymers can then be separated off from the reaction medium and purified is known to the person skilled in the art and is described in detail in the literature, for example in WO 2003/048225, WO 2004/037887 and WO 2004/037887.

The present invention thus also relates to a process for the preparation of the polymers, oligomers and dendrimers according to the invention, which is characterised in that they are prepared by SUZUKI polymerisation, YAMAMOTO polymerisation, STILLE polymerisation or HARTWIG-BUCHWALD polymerisation. The dendrimers according to the invention can be prepared by processes known to the person skilled in the art or analogously thereto. Suitable processes are described in the literature, such as, for example, in Frechet, Jean M. J.; Hawker, Craig J., "Hyperbranched polyphenylene and hyperbranched polyesters: new soluble, three-dimensional, reactive polymers", Reactive & Functional Polymers (1995), 26(1-3), 127-36; Janssen, H. M.; Meijer, E. W., "The synthesis and characterization of dendritic molecules", Materials Science and Technology (1999), 20 (Synthesis of Polymers), 403-458; Tomalia, Donald A., "Dendrimer molecules", Scientific American (1995), 272(5), 62-6; WO 2002/067343 A1 and WO 2005/026144 A1.

The compounds, polymers, oligomers and dendrimers according to the invention can be employed as compositions with other organically functional materials which are used in electronic devices. A large number of possible organically functional materials is known to the person skilled in the art from the prior art. The present invention therefore also relates to a composition comprising one or more compounds of the formula (255) according to the invention or at least one polymer, oligomer or dendrimer according to the invention and at least one further organically functional material selected from the group consisting of fluorescent emitters, phosphorescent emitters, host materials, matrix materials, electron-transport materials, electron-injection materials, hole-conductor materials, hole-injection materials, electron-blocking materials and hole-blocking materials.

For the processing of the compounds from the liquid phase, for example by spin coating or by printing processes, formulations of the compounds according to the invention are necessary. These formulations can be, for example, solutions, dispersions or mini-emulsions. It may be preferred to use mixtures of two or more solvents for this purpose. Suitable and preferred solvents are, for example, toluene, anisole, o-, m-oder p-xylene, methyl benzoate, dimethylanisole, mesitylene, tetralin, veratrol, THE, methyl-THF, THP, chlorobenzene, dioxane or mixtures of these solvents.

The invention therefore furthermore relates to a formulation, in particular a solution, dispersion or mini-emulsion, comprising at least one compound, polymer, oligomer or dendrimer according to the invention containing at least one unit of the formula (1) or (255), and at least one solvent, preferably an organic solvent. The way in which solutions of this type can be prepared is known to the person skilled in the art and is described, for example, in WO 2002/072714, WO 2003/019694 and the literature cited therein.

The compounds according to the invention are suitable for use in electronic devices, in particular in organic electroluminescent devices (for example OLEDs or OLECs). Depending on the substitution, the compounds are employed in different functions and layers.

The present invention therefore furthermore relates to the use of a compound of the formula (255) in electronic devices and to electronic devices themselves which comprise one or more compounds of the formula (255). The electronic devices here are preferably selected from the group consisting of organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and particularly preferably organic electroluminescent devices (OLEDs and OLECs).

The invention relates, as already stated above, to electronic devices comprising at least one compound of the formula (255). The electronic devices here are preferably selected from the devices mentioned above. Particular preference is given to organic electroluminescent devices (OLEDs) comprising an anode, a cathode and at least one emitting layer, characterised in that at least one organic layer, which may be an emitting layer, a hole-transport layer or another layer, comprises at least one compound of the formula (255).

Apart from the cathode, anode and emitting layer, the organic electroluminescent device may also comprise further layers. These are selected, for example, from in each case one or more hole-injection layers, hole-transport layers, hole-blocking layers, electron-transport layers, electron-injection layers, electron-blocking layers, exciton-blocking layers, interlayers, charge-generation layers (IDMC 2003, Taiwan; Session 21 OLED (5), T. Matsumoto, T. Nakada, J. Endo, K. Mori, N. Kawamura, A. Yokoi, J. Kido, Multiphoton Organic EL Device Having Charge Generation Layer) and/or organic or inorganic p/n junctions. However, it should be pointed out that each of these layers does not necessarily have to be present and the choice of layers is always dependent on the compounds used and in particular also on whether the electroluminescent device is fluorescent or phosphorescent.

The organic electroluminescent device according to the invention may comprise a plurality of emitting layers. These emission layers in this case particularly preferably have in total a plurality of emission maxima between 380 nm and 750 nm, resulting overall in white emission, i.e. various emitting compounds which are able to fluoresce or phosphoresce and which emit blue or yellow or orange or red light are used in the emitting layers. Particular preference is given to three-layer systems, i.e. systems having three emitting layers, where the three layers exhibit blue, green and orange or red emission (for the basic structure see, for example, WO 2005/011013). The compounds according to the invention may be present in such devices in a hole-transport layer, an emitting layer and/or in another layer. It should be noted that, for the generation of white light, an emitter compound used individually which emits in a broad wavelength range may also be suitable instead of a plurality of emitter compounds emitting in a colour.

It is preferred in accordance with the invention if the compound of the formula (1) or (255) is employed in an organic electroluminescent device comprising one or more phosphorescent dopants. The compound can be used in various layers here, preferably in an hole-transport layer, a hole-injection layer or in an emitting layer. However, the compound of the formula (255) can also be employed in accordance with the invention in an electronic device comprising one or more fluorescent dopants.

The term phosphorescent dopants typically encompasses compounds in which the light emission takes place by a spin-forbidden transition, for example a transition from an excited triplet state or a state having a relatively high spin quantum number, for example a quintet state.

Suitable phosphorescent dopants (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent emitters used are preferably compounds which contain copper, molybdenum, tungsten, rhenium, ruthenium, osmium, rhodium, iridium, palladium, platinum, silver, gold or europium, in particular compounds which contain iridium, platinum or copper.

For the purposes of the present invention, all luminescent iridium, platinum or copper complexes are regarded as phosphorescent compounds.

Examples of the emitters described above are revealed by the applications WO 00/70655, WO 01/41512, WO 02/02714, WO 02/15645, EP 1191613, EP 1191612, EP 1191614, WO 05/033244, WO 2005/019373 and US 2005/0258742. In general, all phosphorescent complexes as used in accordance with the prior art for phosphorescent OLEDs and as are known to the person skilled in the art in the area of organic electroluminescent devices are suitable. The person skilled in the art will also be able to employ further phosphorescent complexes without inventive step in combination with the compounds of the formula (1) or (255) in organic electroluminescent devices.

Explicit examples of suitable phosphorescent emitter compounds are furthermore revealed by the following table.

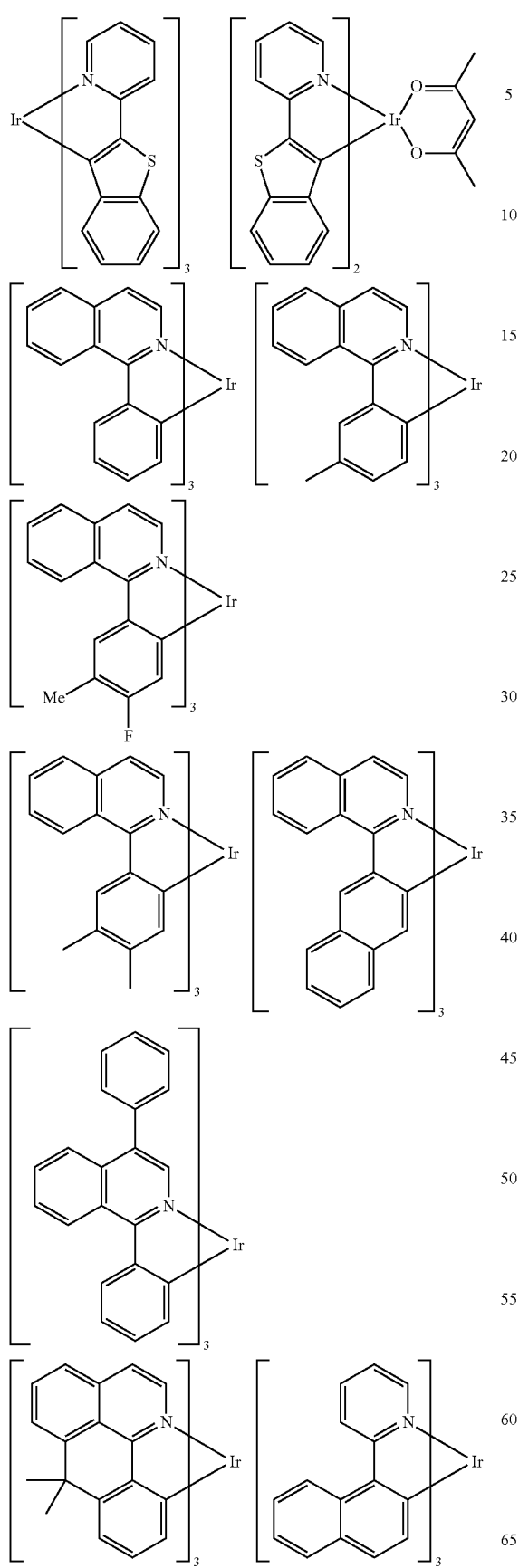
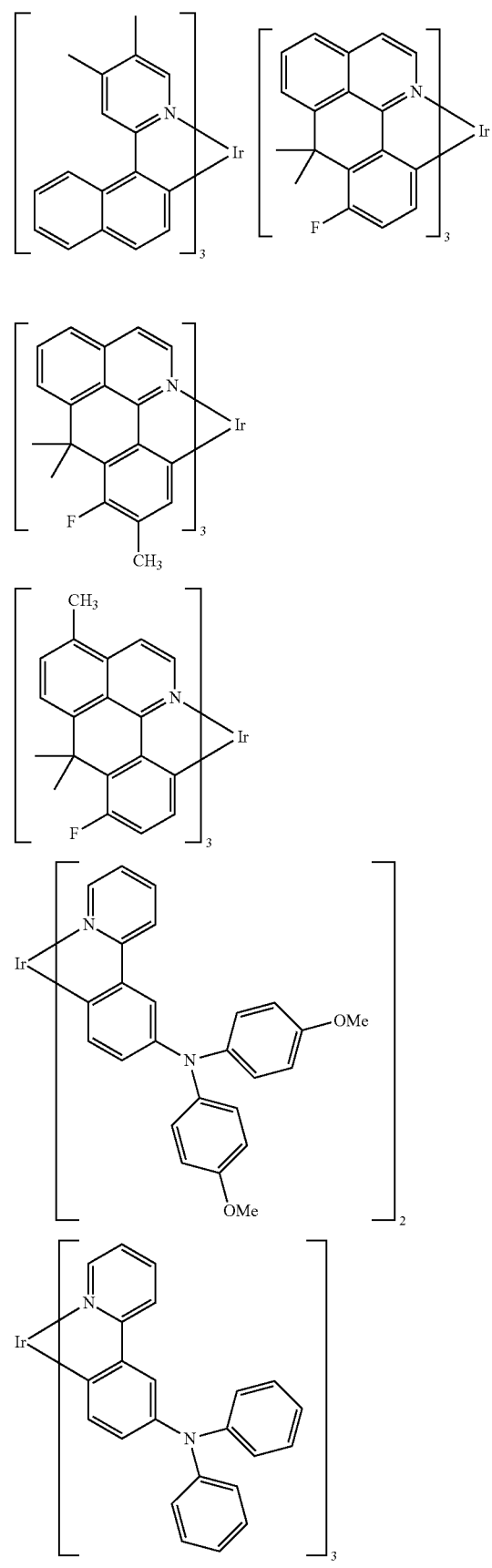

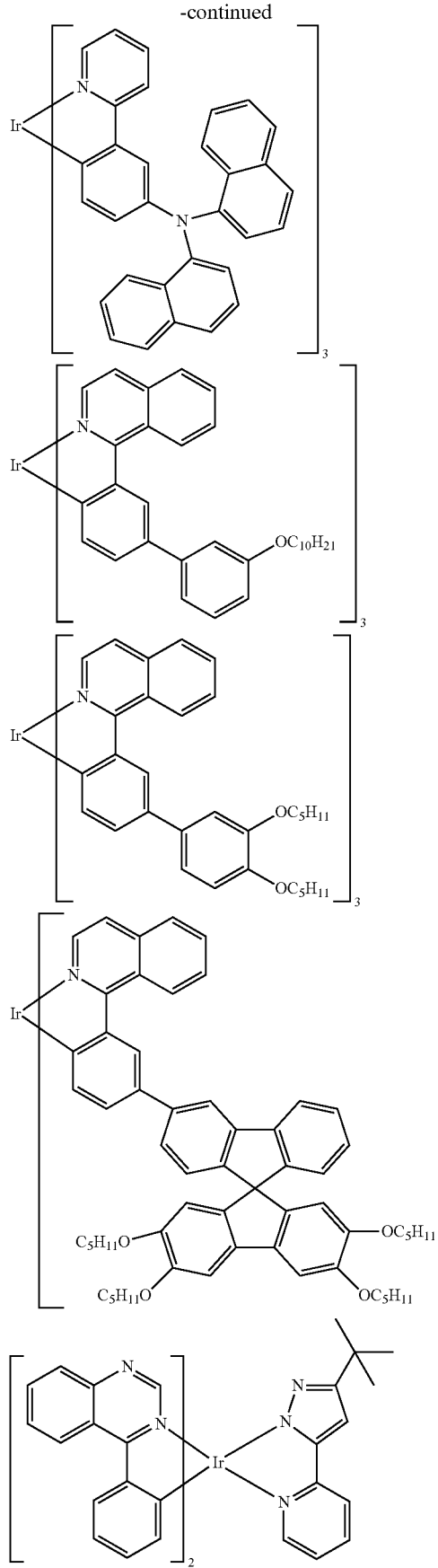
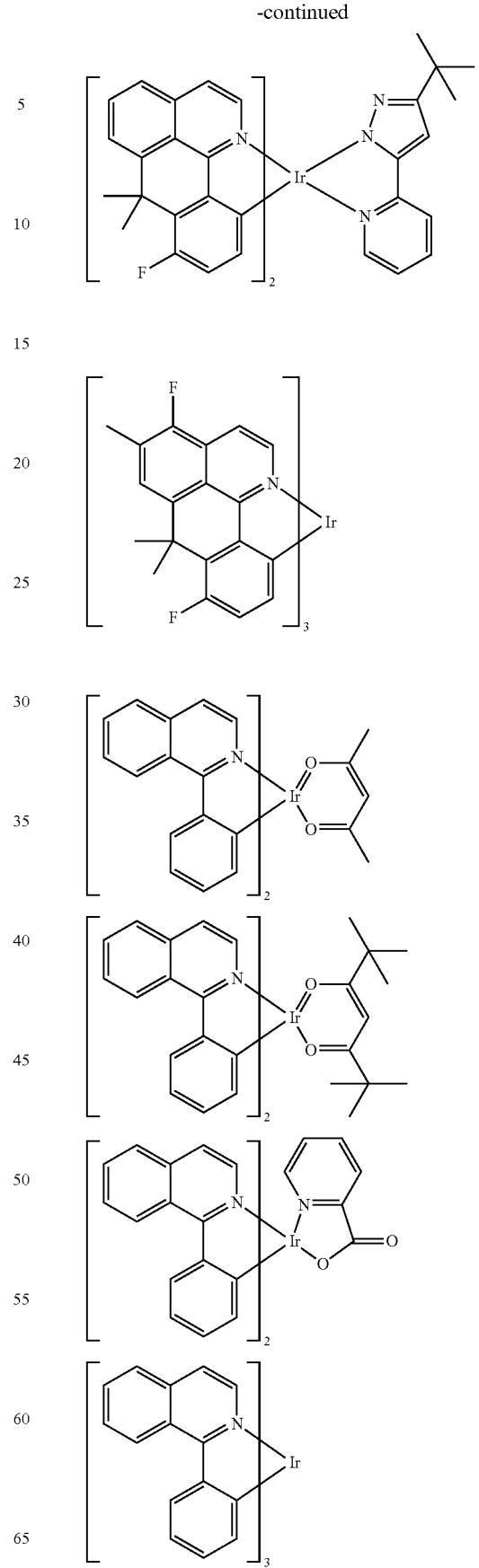

85
-continued
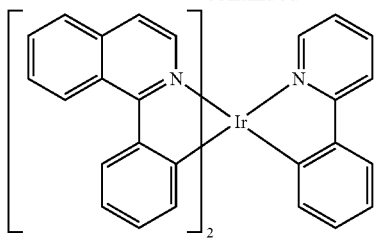
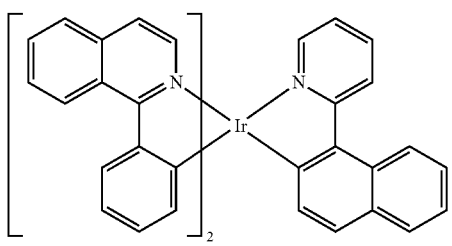
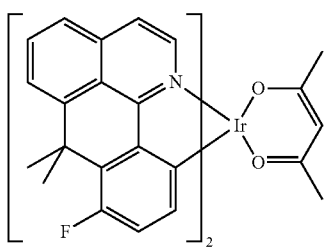
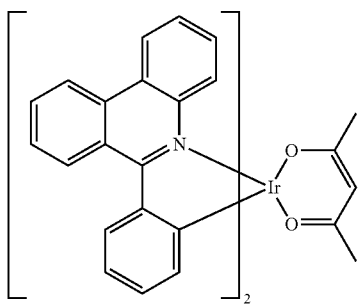
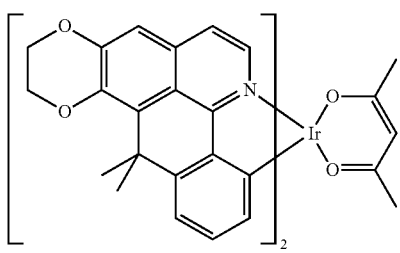
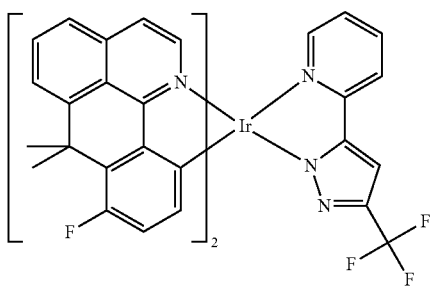
86
-continued
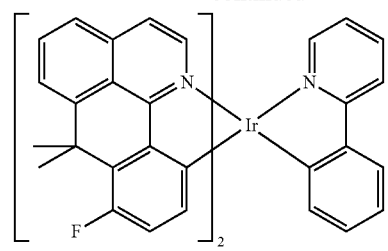
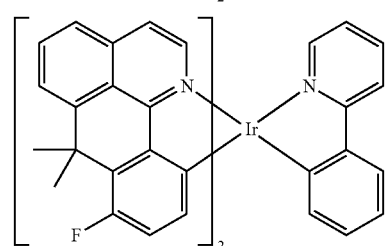
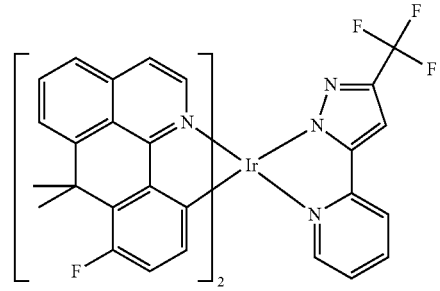
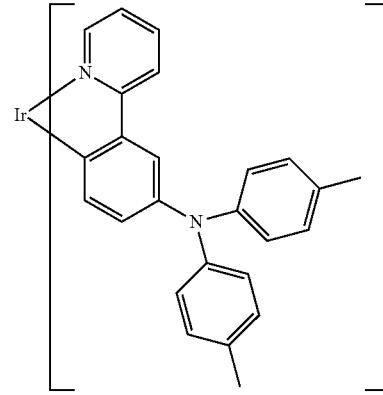
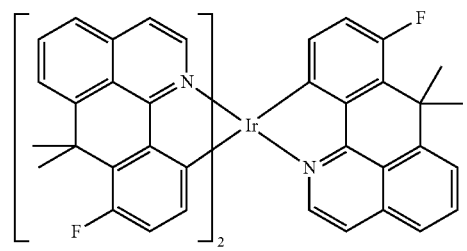
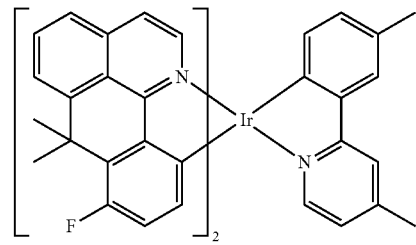

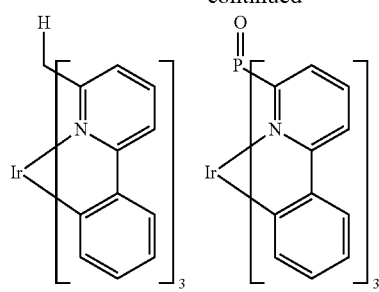
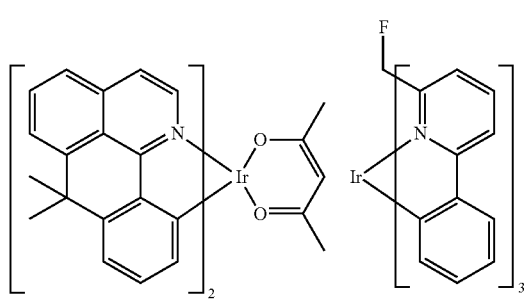
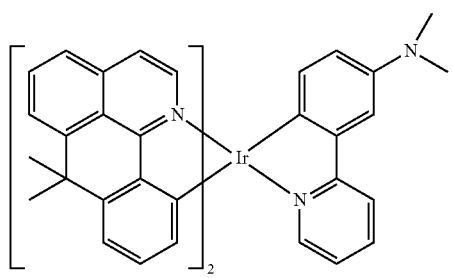
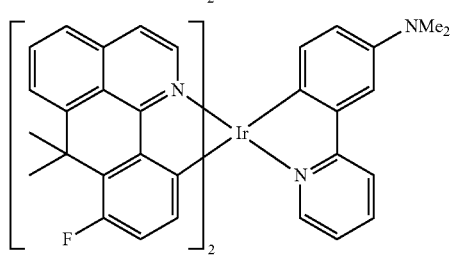
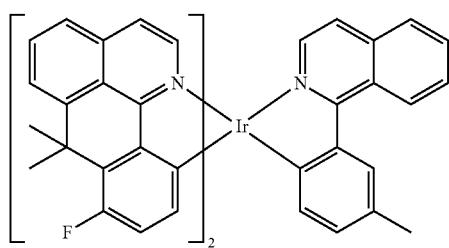
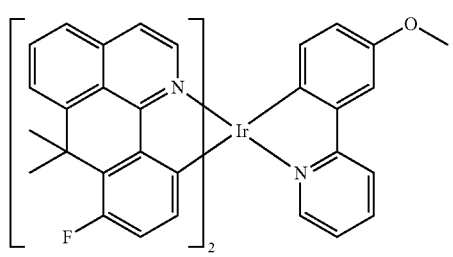
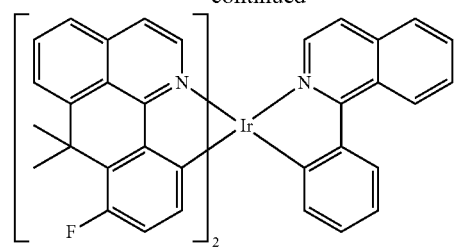
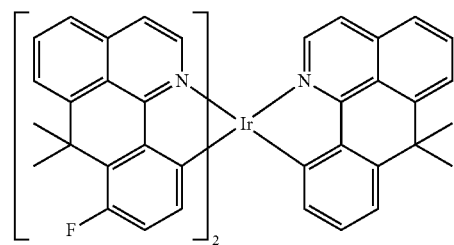
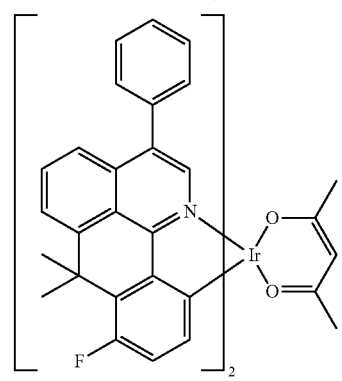
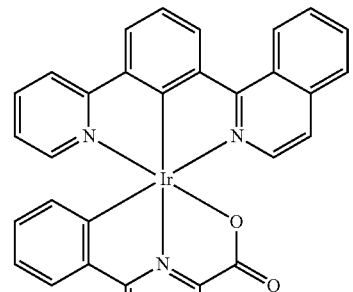
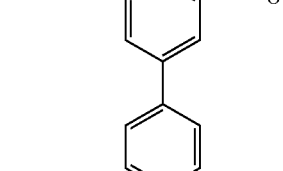
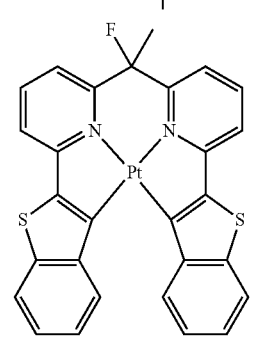

89
-continued
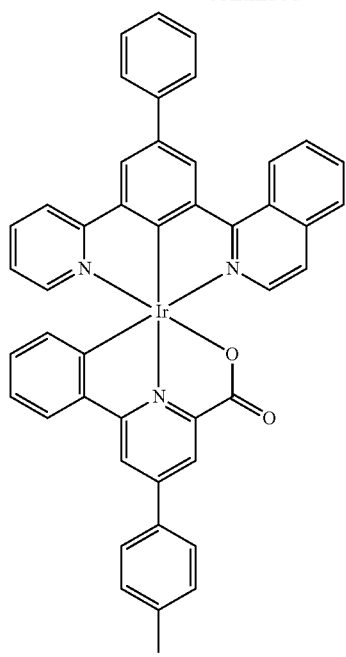
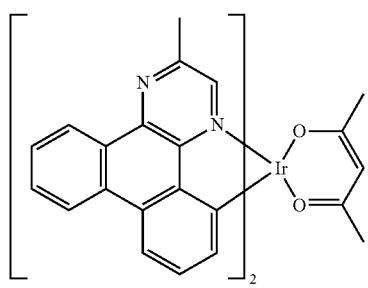
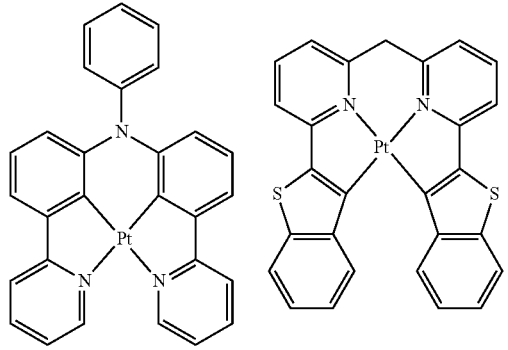
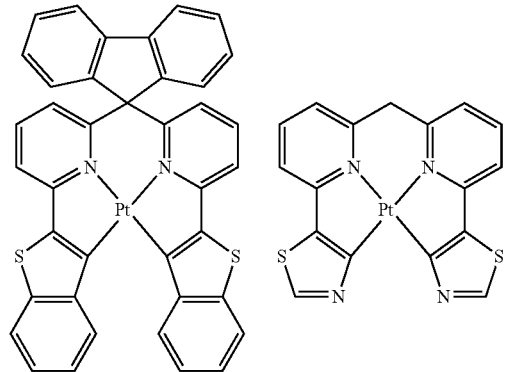
90
-continued
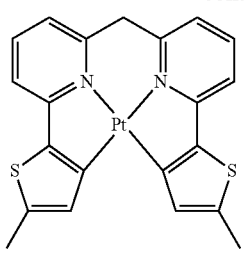
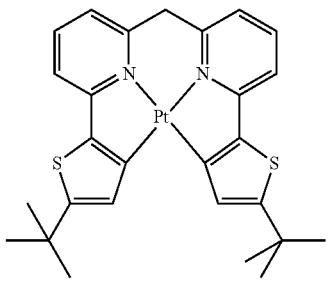
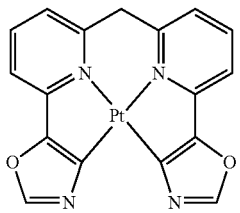
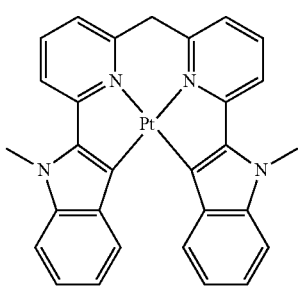
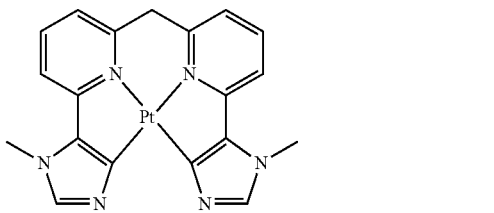
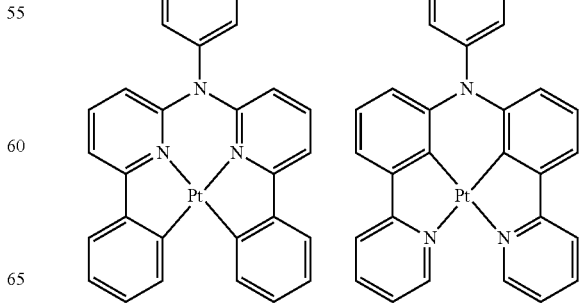

91
-continued
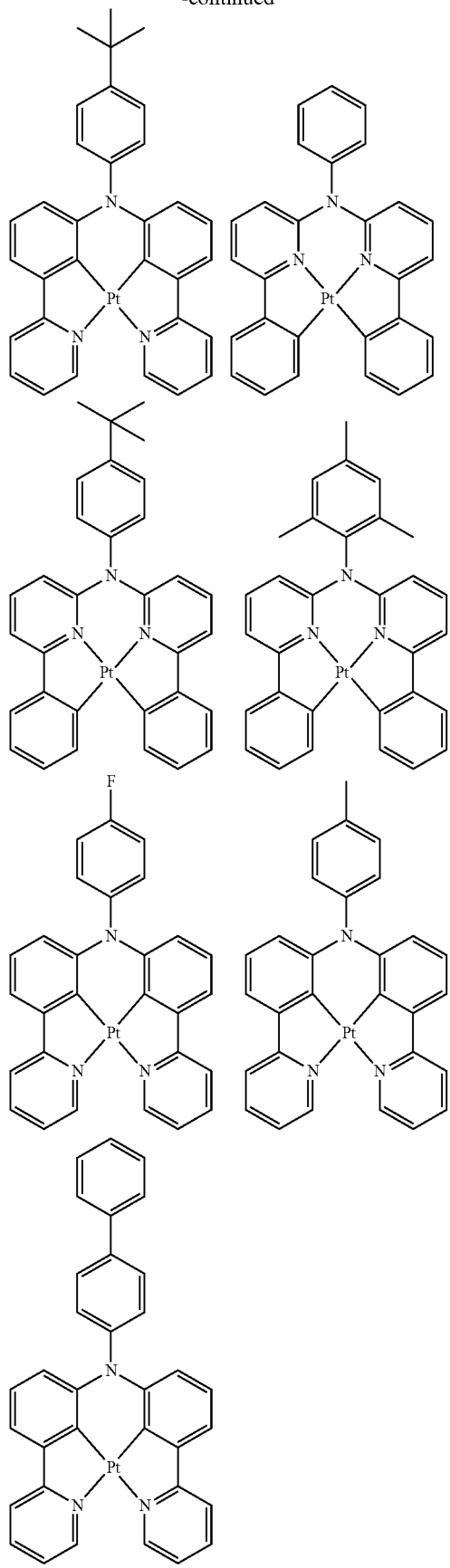
92
-continued
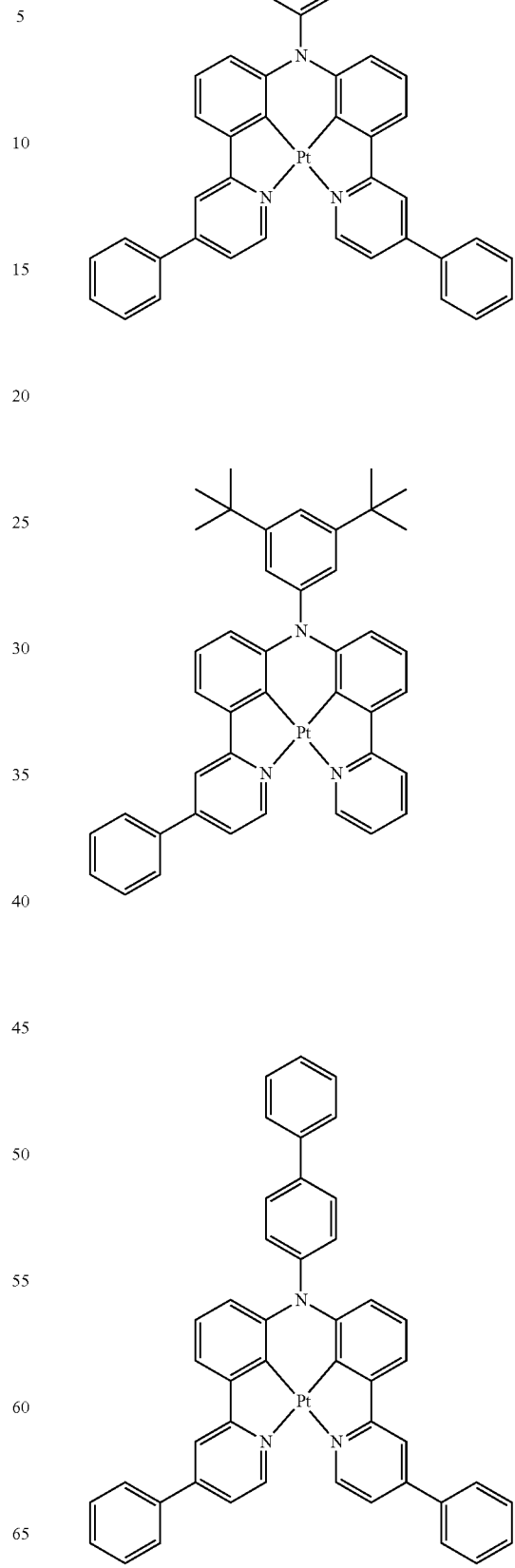

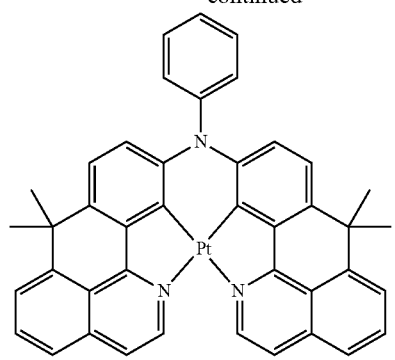
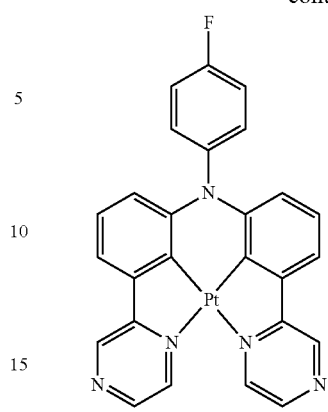
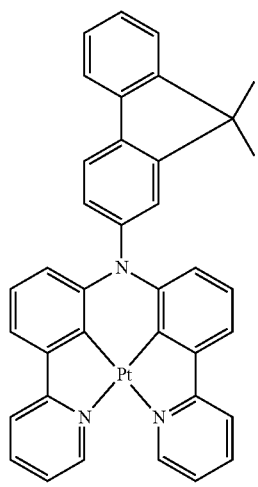
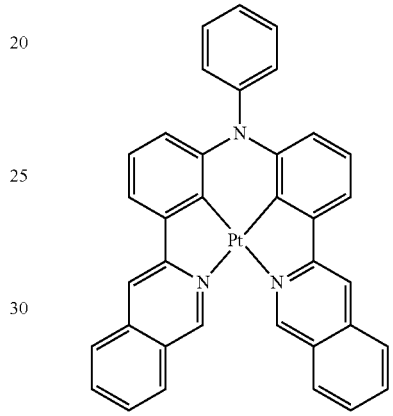
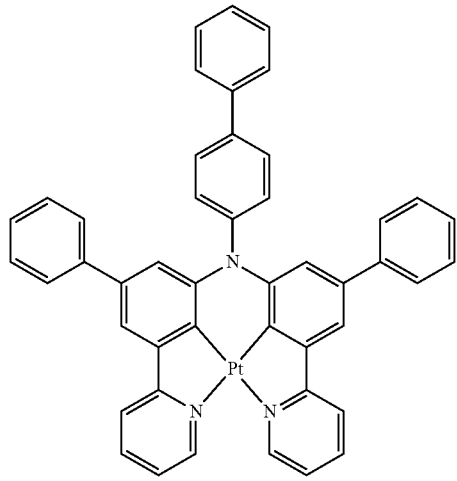
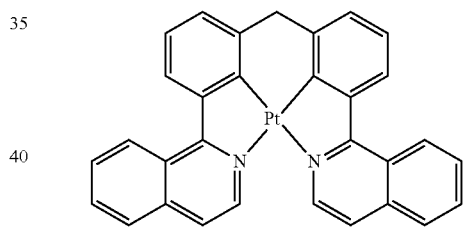
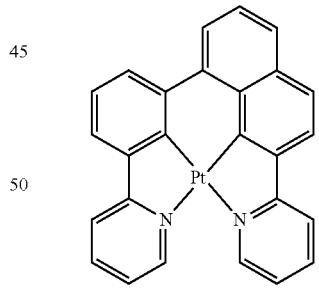
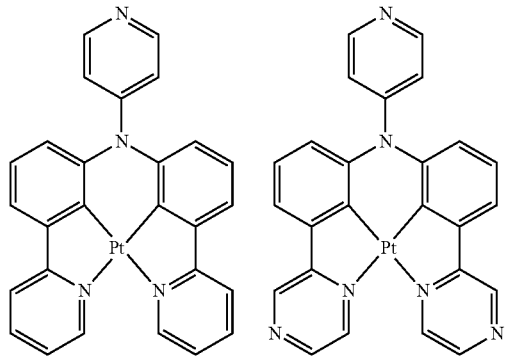
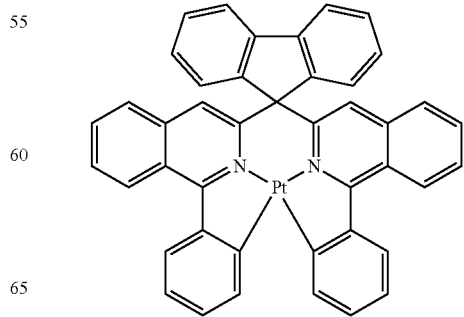

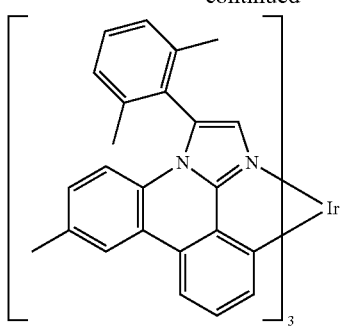
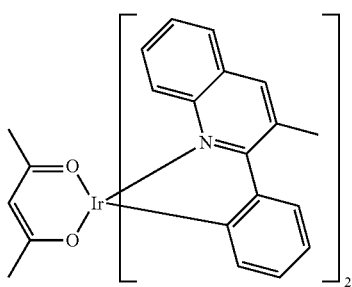
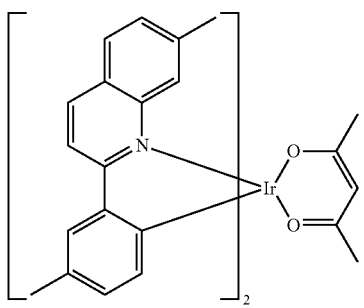
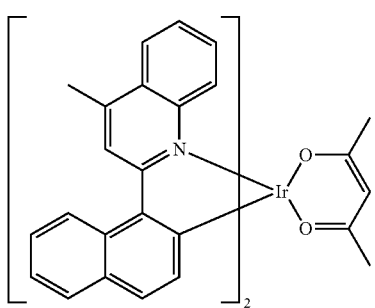
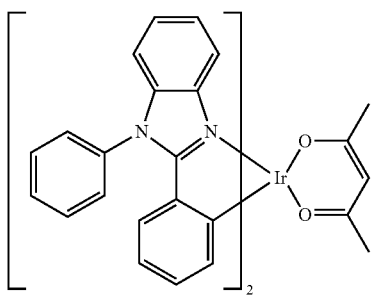
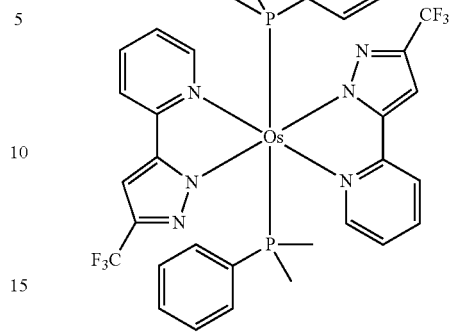
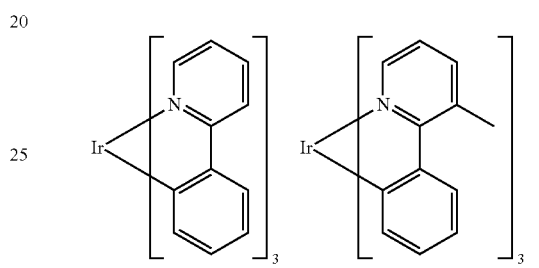
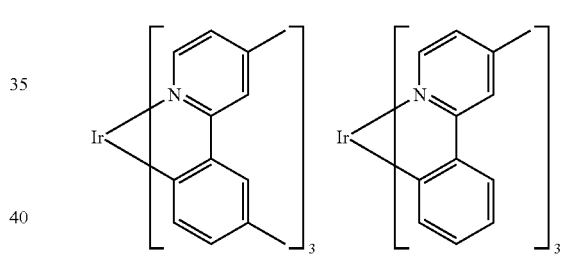
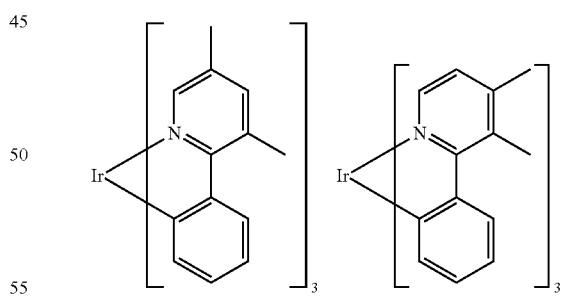
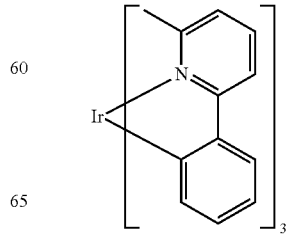

97
-continued
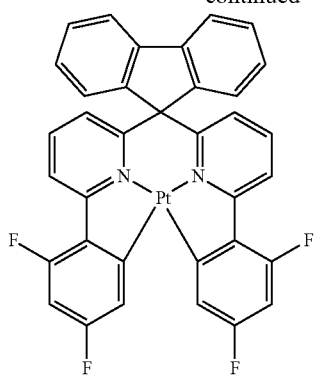
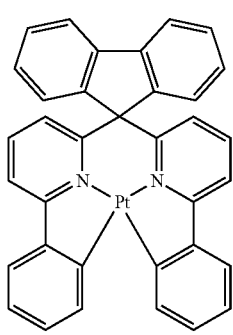
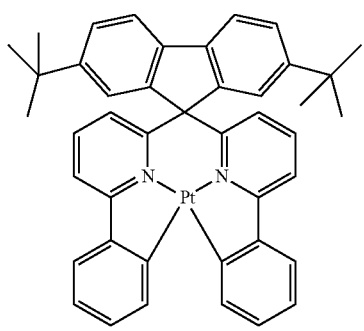
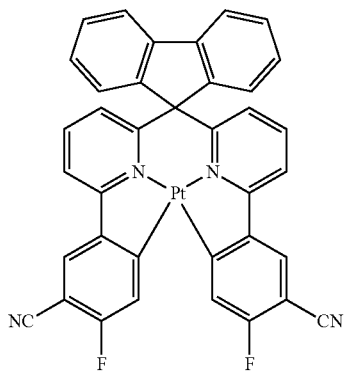
98
-continued
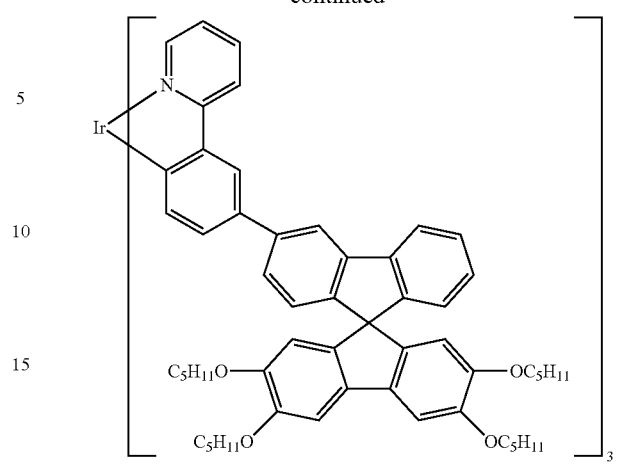
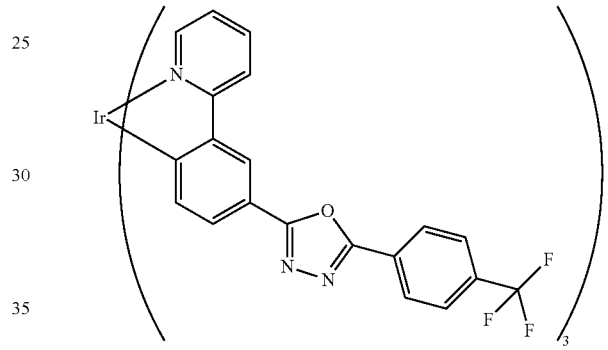
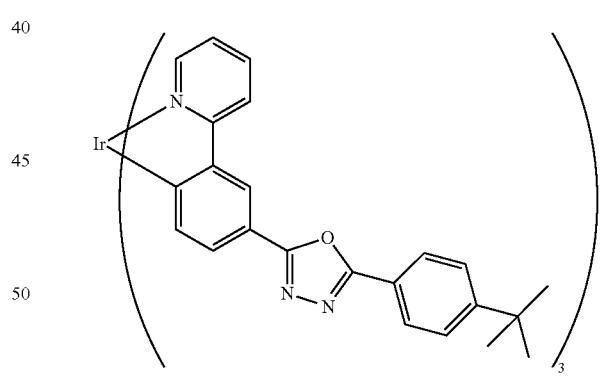
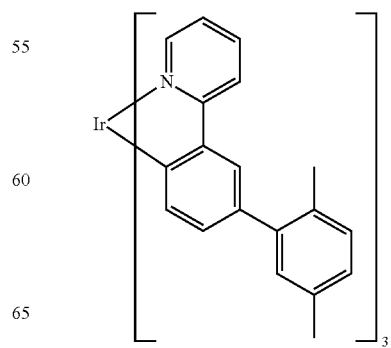

99
-continued
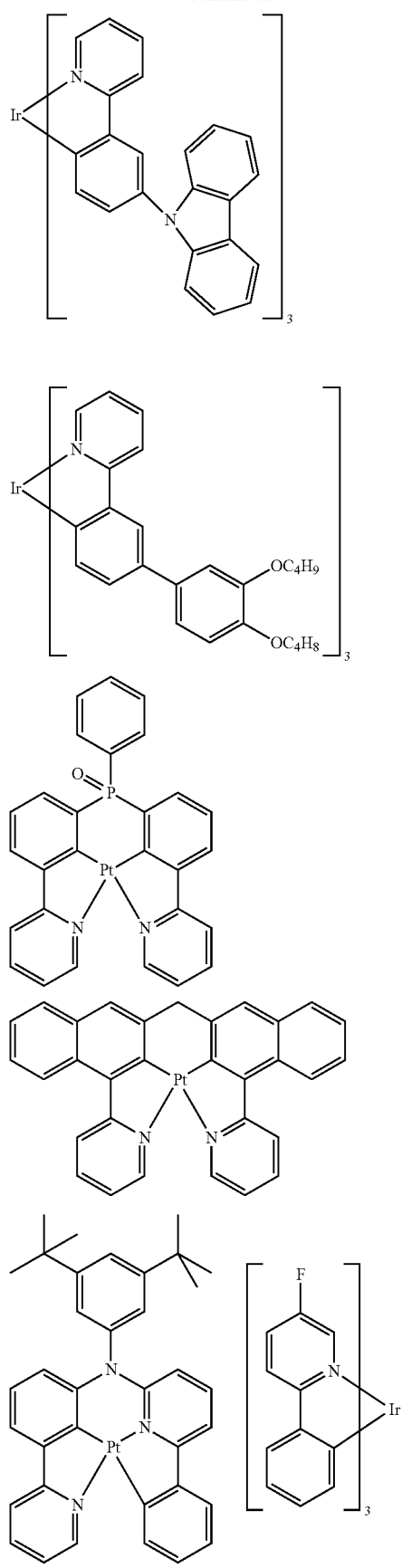
100
-continued
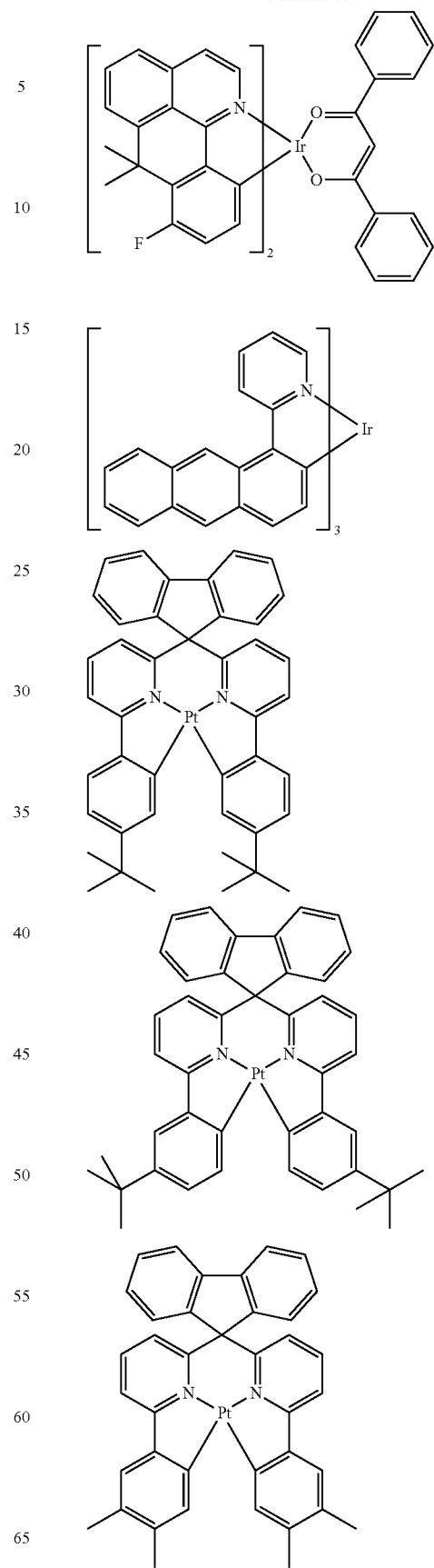

101
-continued
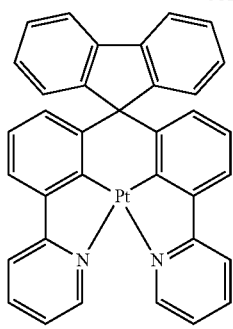
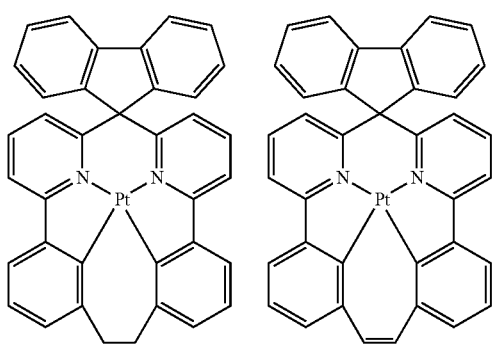
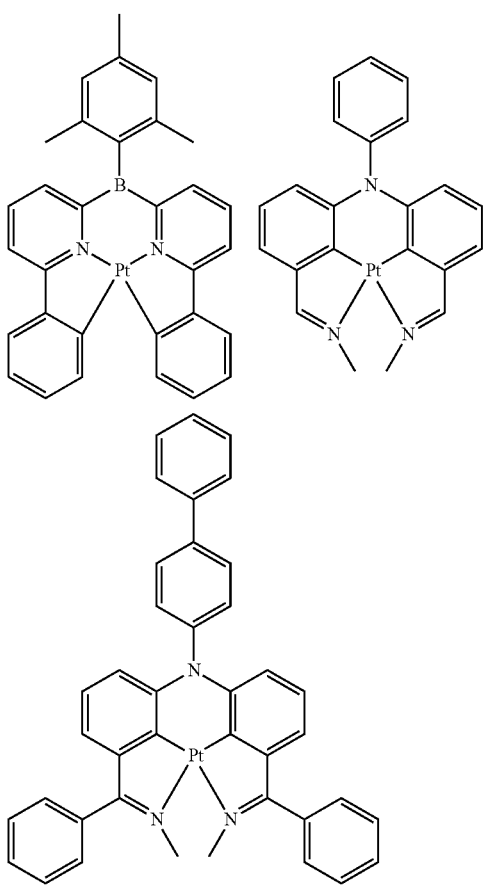
102
-continued
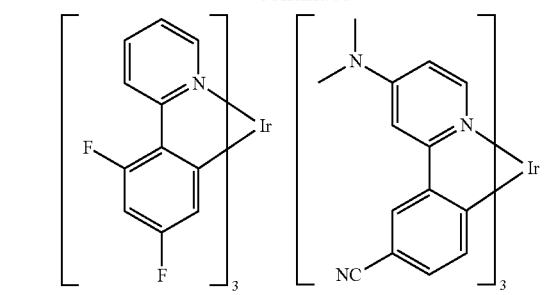
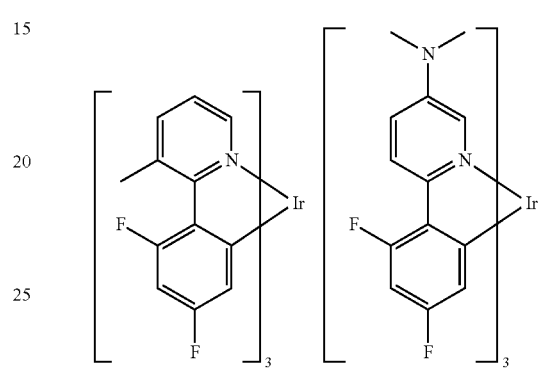
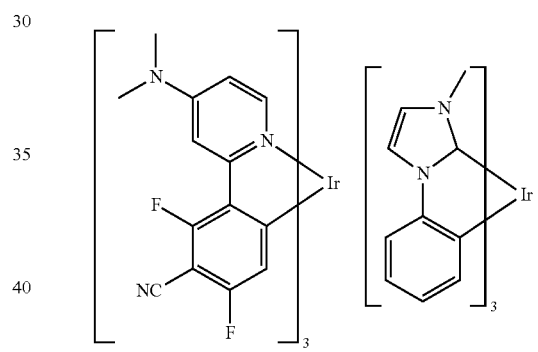
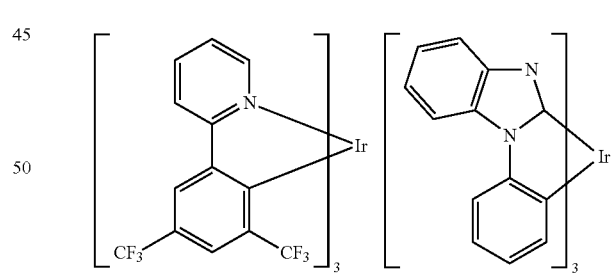
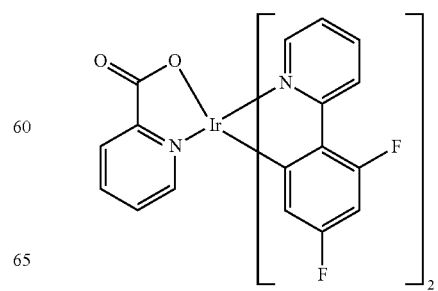

103
-continued
104
-continued
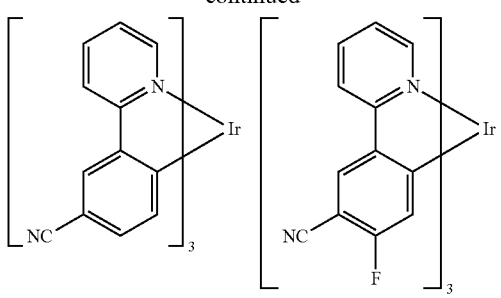
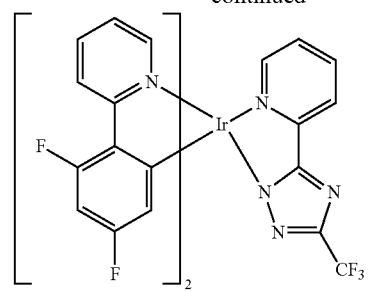
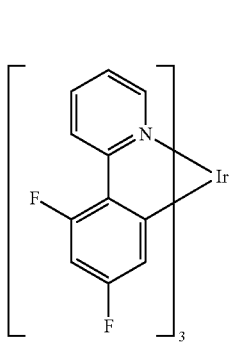
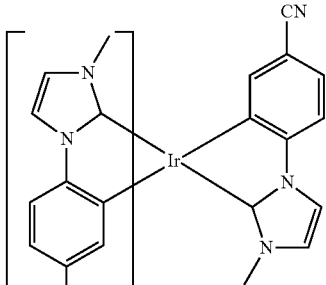
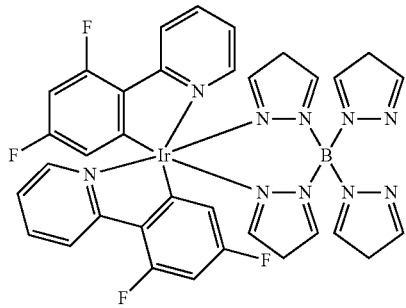
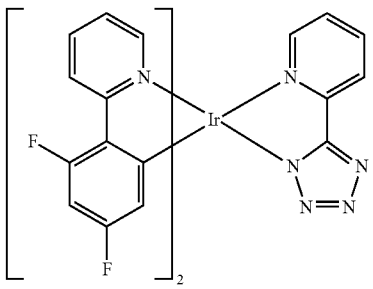
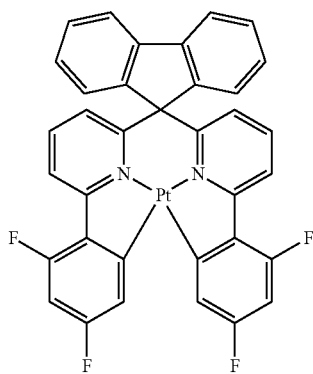
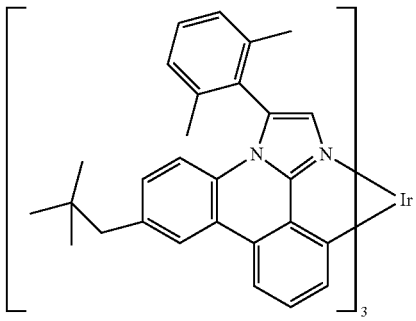
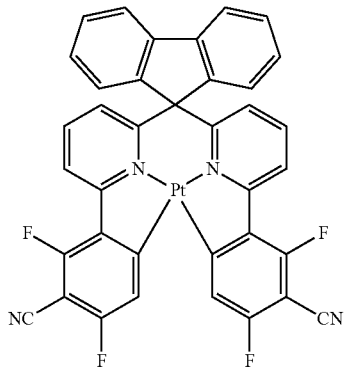
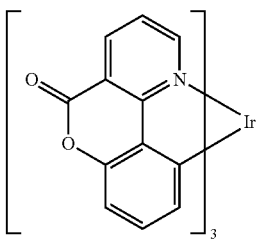
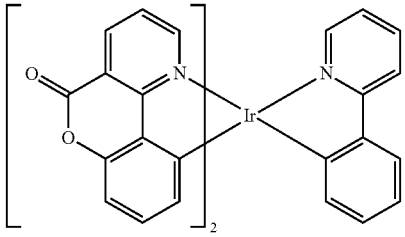

-continued

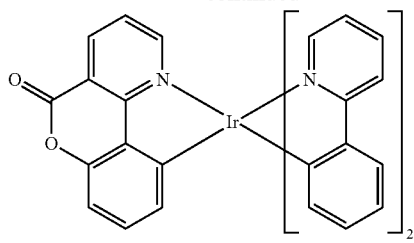

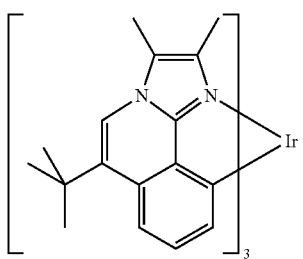

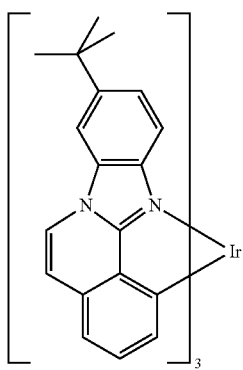

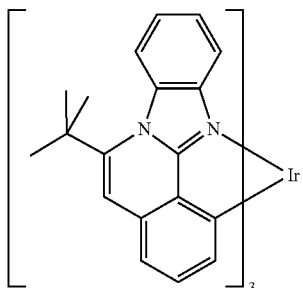

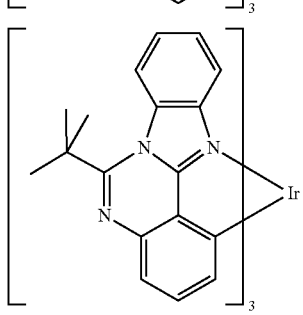

-continued

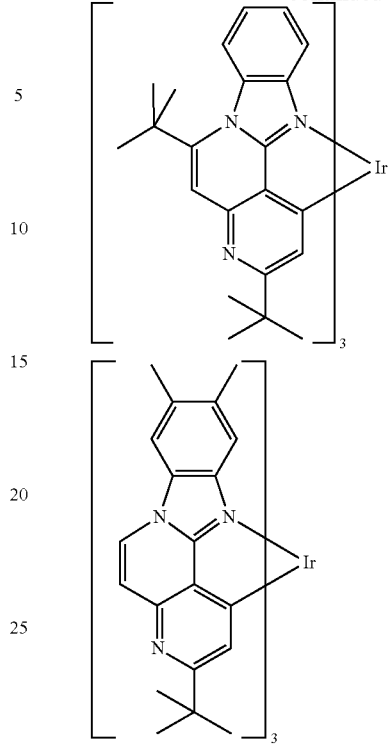

In a preferred embodiment of the invention, the compounds of the general formula (1) or (255) are employed as hole-transport material. The compounds are then preferably employed in a hole-transport layer and/or in a hole-injection layer. A hole-injection layer in the sense of this invention is a layer which is directly adjacent to the anode. A hole-transport layer in the sense of this invention is a layer which is located between the hole-injection layer and the emission layer. The hole-transport layer may be directly adjacent to the emission layer. If the compounds of the formula (1) or (255) are used as hole-transport material or as hole-injection material, it may be preferred for them to be doped with electron-acceptor compounds (p-doping), for example with $F_4$-TCNQ, $F_6$-TNAP or compounds as described in EP 1476881 or EP 1596445. In a further preferred embodiment of the invention, a compound of the formula (1) or (255) is used as hole-transport material in combination with a hexaazatriphenylene derivative, as described in US 2007/0092755. The hexaazatriphenylene derivative here is particularly preferably employed in a separate layer.

If the compounds of the general formula (1) or (255) are employed as hole-transport material in a hole-transport layer, the compound may be employed as pure material, i.e. in a proportion of 100%, in the hole-transport layer, or it may be employed in combination with one or more further compounds in the hole-transport layer.

In a further embodiment of the present invention, the compounds of the general formulae (1) or (255) are employed as emitting materials. For this purpose, the compounds are preferably employed in an emission layer. Besides at least one of the compounds of the general formula (1) or (255), the emission layer furthermore comprises at least one host material. The person skilled in the art will be able to make a selection here from the known host materials without difficulties and without being inventive.

In a further embodiment of the present invention, the compounds of the general formula (1) or (255) are employed as matrix material in combination with one or more dopants, preferably phosphorescent dopants.

A dopant in a system comprising a matrix material and a dopant is taken to mean the component whose proportion in the mixture is the smaller. Correspondingly, a matrix material is taken to mean the component whose proportion in the mixture is the greater in a system comprising a matrix material and a dopant.

The proportion of the matrix material in the emitting layer is in this case between 50.0 and 99.9% by vol., preferably between 80.0 and 99.5% by vol. and particularly preferably between 92.0 and 99.5% by vol. for fluorescent emitting layers and between 85.0 and 97.0% by vol. for phosphorescent emitting layers.

Correspondingly, the proportion of the dopant is between 0.1 and 50.0% by vol., preferably between 0.5 and 20.0% by vol. and particularly preferably between 0.5 and 8.0% by vol. for fluorescent emitting layers and between 3.0 and 15.0% by vol. for phosphorescent emitting layers.

An emitting layer of an organic electroluminescent device may also comprise systems comprising a plurality of matrix materials (mixed-matrix systems) and/or a plurality of dopants. In this case too, the dopants are generally the materials whose proportion in the system is the smaller and the matrix materials are the materials whose proportion in the system is the greater. In individual cases, however, the proportion of an individual matrix material in the system may be smaller than the proportion of an individual dopant.

In a further preferred embodiment of the invention, the compounds of the general formula (1) or (255) are used as a component of mixed-matrix systems. The mixed-matrix systems preferably comprise two or three different matrix materials, particularly preferably two different matrix materials. One of the two materials here is preferably a material having hole-transporting properties and the other material is a material having electron-transporting properties. However, the desired electron-transporting and hole-transporting properties of the mixed-matrix components may also be combined principally or completely in a single mixed-matrix components, where the further mixed-matrix component(s) fulfil other functions. The two different matrix materials here may be present in a ratio of 1:50 to 1:1, preferably 1:20 to 1:1, particularly preferably 1:10 to 1:1 and very particularly preferably 1:4 to 1:1. Mixed-matrix systems are preferably employed in phosphorescent organic electroluminescent devices. More precise information on mixed-matrix systems is given, inter alia, in the application WO 2010/108579.

The mixed-matrix systems may comprise one or more dopants, preferably one or more phosphorescent dopants. In general, mixed-matrix systems are preferably employed in phosphorescent organic electroluminescent devices.

Particularly suitable matrix materials which can be used as matrix components of a mixed-matrix system in combination with the compounds according to the invention are selected from the preferred matrix materials for phosphorescent dopants indicated below or the preferred matrix materials for fluorescent dopants, depending on what type of dopant is employed in the mixed-matrix system.

Preferred phosphorescent dopants for use in mixed-matrix systems are the phosphorescent dopants shown in the above table.

The materials preferably employed in the relevant functions in the devices according to the invention are indicated below.

Preferred fluorescent dopants are selected from the class of the arylamines. An arylamine or aromatic amine in the sense of this invention is taken to mean a compound which contains three substituted or unsubstituted aromatic or heteroaromatic ring systems bonded directly to the nitrogen. At least one of these aromatic or heteroaromatic ring systems is preferably a condensed ring system, particularly preferably having at least 14 aromatic ring atoms. Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups are preferably bonded to the pyrene in the 1-position or in the 1,6-position.

Suitable matrix materials, preferably for fluorescent dopants, besides the compounds according to the invention, are materials from various classes of substance. Preferred matrix materials are selected from the classes of the oligoarylenes (for example 2,2',7,7'-tetraphenylspirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 2004/081017), the hole-conducting compounds (for example in accordance with WO 2004/058911), the electron-conducting compounds, in particular ketones, phosphine oxides, sulfoxides, etc. (for example in accordance with WO 2005/084081 and WO 2005/084082), the atropisomers (for example in accordance with WO 2006/048268), the boronic acid derivatives (for example in accordance with WO 2006/117052) or the benzanthracenes (for example in accordance with WO 2008/145239). Particularly preferred matrix materials are selected from the classes of the oligoarylenes, comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes, comprising anthracene, benzanthracene, benzophenanthrene and/or pyrene or atropisomers of these compounds. An oligoarylene in the sense of this invention is intended to be taken to mean a compound in which at least three aryl or arylene groups are bonded to one another.

Preferred matrix materials for phosphorescent dopants, besides the compounds according to the invention, are aromatic amines, in particular triarylamines, for example in accordance with US 2005/0069729, carbazole derivatives (for example CBP, N,N-biscarbazolylbiphenyl) or compounds in accordance with WO 2005/039246, US 2005/0069729, JP 2004/288381, EP 1205527 or WO 2008/086851, bridged carbazole derivatives, for example in accordance with WO 2011/088877 and WO 2011/128017, indenocarbazole derivatives, for example in accordance with WO 2010/136109 and WO 2011/000455, azacarbazole derivatives, for example in accordance with EP 1617710, EP 1617711, EP 1731584, JP 2005/347160, indolocarbazole derivatives, for example in accordance with WO 2007/063754 or WO 2008/056746, ketones, for example in accordance with WO 2004/093207 or WO 2010/006680, phosphine oxides, sulfoxides and sulfones, for example in accordance with WO 2005/003253, oligophenylenes, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2010/015306, WO 2007/063754 or WO 2008/056746, zinc complexes, for example in accordance with EP 652273 or WO 2009/062578, aluminium complexes, for example BAlq, diazasilole and tetraazasilole derivatives, for example in accordance with WO 2010/054729, diazaphosphole derivatives, for example in accordance with WO 2010/054730, and aluminium complexes, for example BAlq.

Suitable charge-transport materials, as can be used in the hole-injection or hole-transport layer or in the electron-transport layer of the organic electroluminescent device according to the invention, are, for example, the compounds disclosed in Y. Shirota et al., *Chem. Rev.* 2007, 107(4), 953-1010, or other materials as are employed in these layers in accordance with the prior art.

The cathode of the organic electroluminescent device preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag or Al, can also be used in addition to the said metals, in which case combinations of the metals, such as, for example, Ca/Ag, Mg/Ag or Ag/Ag, are generally used. It may also be preferred to introduce a thin interlayer of a material having a high dielectric constant between a metallic cathode and the organic semiconductor. Suitable for this purpose are, for example, alkali metal fluorides or alkaline-earth metal fluorides, but also the corresponding oxides or carbonates (for example LiF, $Li_2O$, $BaF_2$, MgO, NaF, CsF, $Cs_2CO_3$, etc.). Furthermore, lithium quinolinate (LiQ) can be used for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example $Al/Ni/NiO_x$, $Al/PtO_x$) may also be preferred. For some applications, at least one of the electrodes must be transparent or partially transparent in order to facilitate either irradiation of the organic material (organic solar cells) or the coupling-out of light (OLEDs, O-lasers). Preferred anode materials here are conductive mixed metal oxides. Particular preference is given to indium tin oxide (ITO) or indium zinc oxide (IZO).

Preference is furthermore given to conductive, doped organic materials, in particular conductive, doped polymers.

The device is appropriately (depending on the application) structured, provided with contacts and finally sealed, since the lifetime of the devices according to the invention is shortened in the presence of water and/or air.

In a preferred embodiment, the organic electroluminescent device according to the invention is characterised in that one or more layers are coated by means of a sublimation process, in which the materials are applied by vapour deposition in vacuum sublimation units at an initial pressure of less than $10^{-5}$ mbar, preferably less than $10^{-6}$ mbar. However, it is also possible here for the initial pressure to be even lower, for example less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure of between $10^{-5}$ mbar and 1 bar, A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, nozzle printing or offset printing, but particularly preferably LITI (light induced thermal imaging, thermal transfer printing) or ink-jet printing. Soluble compounds of the formula (1) or (255) are necessary for this purpose. High solubility can be achieved through suitable substitution of the compounds.

For the production of an organic electroluminescent device according to the invention, it is furthermore preferred to apply one or more layers from solution and one or more layers by a sublimation process.

In accordance with the invention, the electronic devices comprising one or more compounds of the general formula (1) or (255) can be employed in displays, as light sources in lighting applications and as light sources in medical and/or cosmetic applications (for example light therapy).

Devices comprising the compounds of the general formula (1) or (255) can be employed in a very versatile manner. Thus, for example, electroluminescent devices comprising one or more compounds of the general formula (1) or (255) can be employed in displays for televisions, mobile telephones, computers and cameras. However, the devices can also be used in lighting applications. Furthermore, electroluminescent devices, for example in OLEDs or OLECs, comprising at least one of the compounds of the general formula (1) or (255) can be used for phototherapy in medicine or the cosmetics field. Thus, a large number of diseases (psoriasis, atopic dermatitis, inflammation, acne, skin cancer, etc.) can be treated or skin wrinkling, skin reddening and skin ageing can be prevented or reduced. Furthermore, the light-emitting devices can be utilised in order to keep drinks, meals or foods fresh or in order to sterilise equipment (for example medical equipment).

The compounds according to the invention and the organic electroluminescent devices according to the invention are distinguished by the following surprising advantages over the prior art:

1. The compounds according to the invention are very suitable for use in a hole-transport layer or a hole-injection layer in electronic devices, such as, for example, in organic electroluminescent devices, in particular owing to their high hole mobility.
2. The compounds according to the invention have a relatively low sublimation temperature, high temperature stability and high oxidation stability, a high glass-transition temperature and low crystallinity, which is advantageous both for the processability, for example from solution or from the gas phase, and also for use in electronic devices.

3. The use of the compounds according to the invention in electronic devices, in particular employed as hole-transport or hole-injection material, results in high efficiencies, low operating voltages and in long lifetimes.

It should be pointed out that variations of the embodiments described in the present invention fall within the scope of this invention. Each feature disclosed in the present invention can, unless explicitly excluded, be replaced by alternative features which serve the same, an equivalent or a similar purpose. Thus, each feature disclosed in the present invention is, unless stated otherwise, to be regarded as an example of a generic series or as an equivalent or similar feature.

All features of the present invention can be combined with one another in any way, unless certain features and/or steps are mutually exclusive. This applies in particular to preferred features of the present invention. Equally, features of non-essential combinations can be used separately (and not in combination).

It should furthermore be pointed out that many of the features, and in particular those of the preferred embodiments of the present invention, are themselves inventive and should not merely be regarded as part of the embodiments of the present invention. For these features, independent protection may be sought in addition or as an alternative to each invention currently claimed.

The teaching on technical action disclosed with the present invention can be abstracted and combined with other examples.

The invention is explained in greater detail by the following examples, without wishing to restrict it thereby.

EXAMPLES

Materials

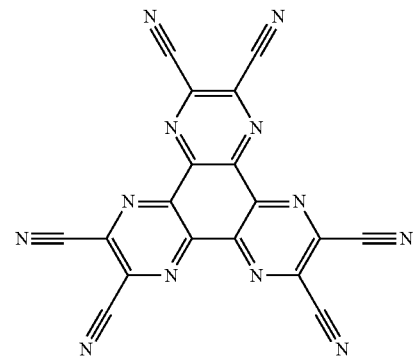

HIL1

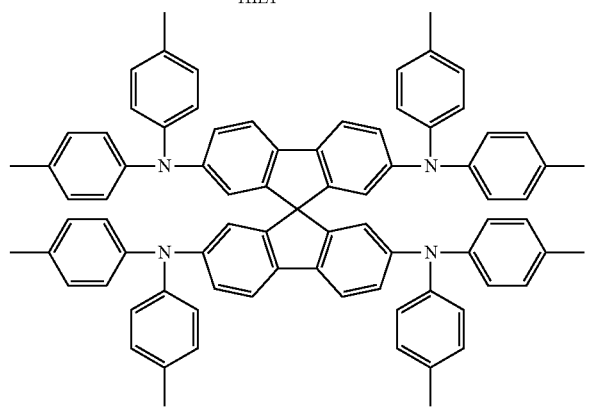

HIL2

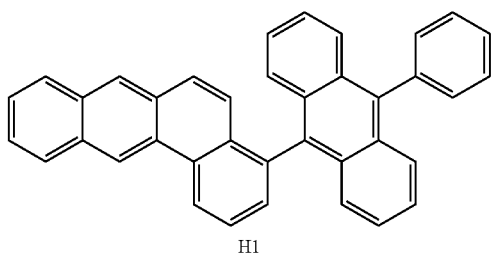

H1

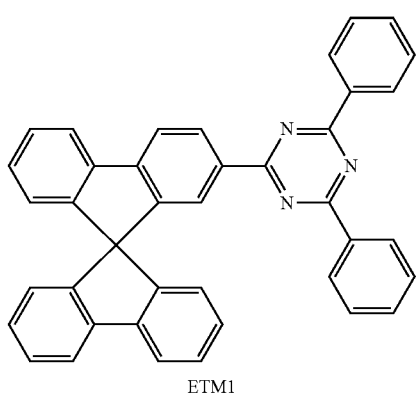

ETM1

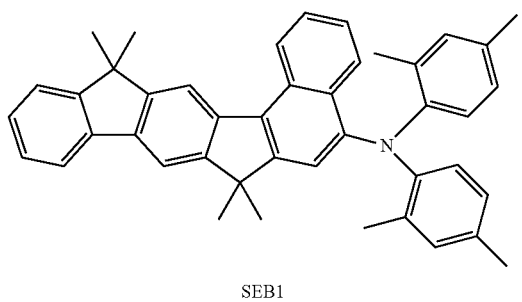

SEB1

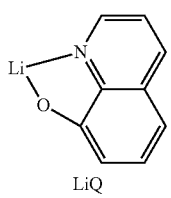

LiQ

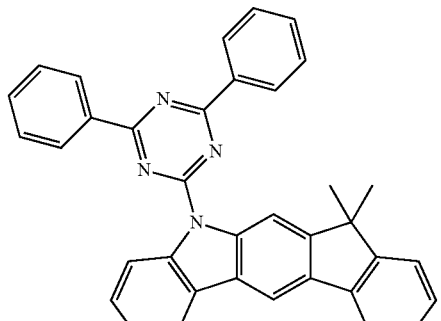

H2

-continued
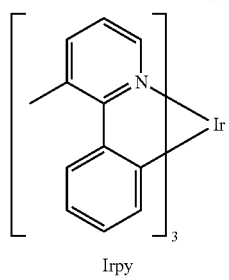
Irpy
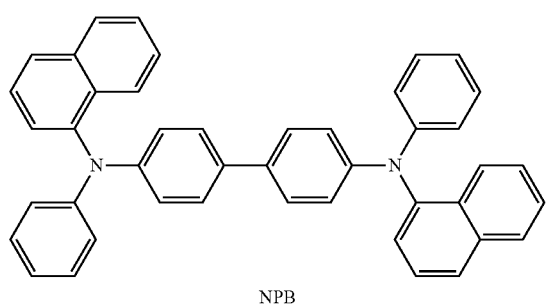
NPB
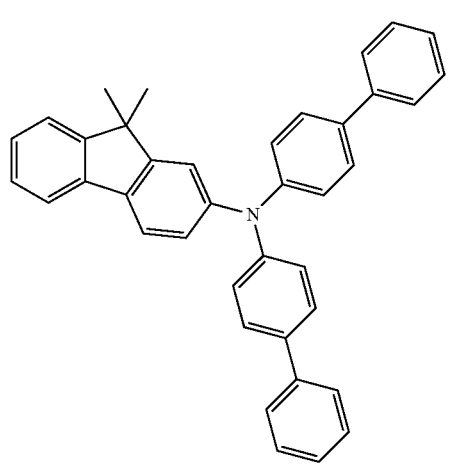
HTMV1
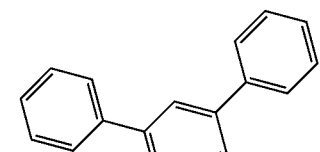
(2-7)
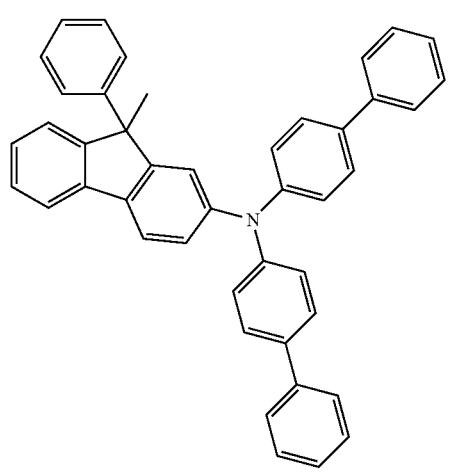
-continued
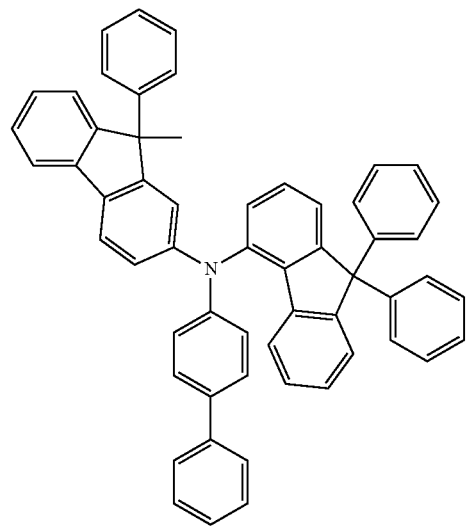
(2-4)
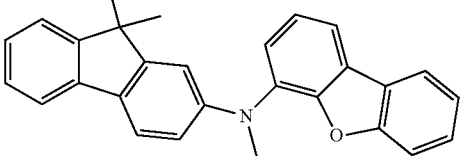
(2-5)

-continued (1-11)

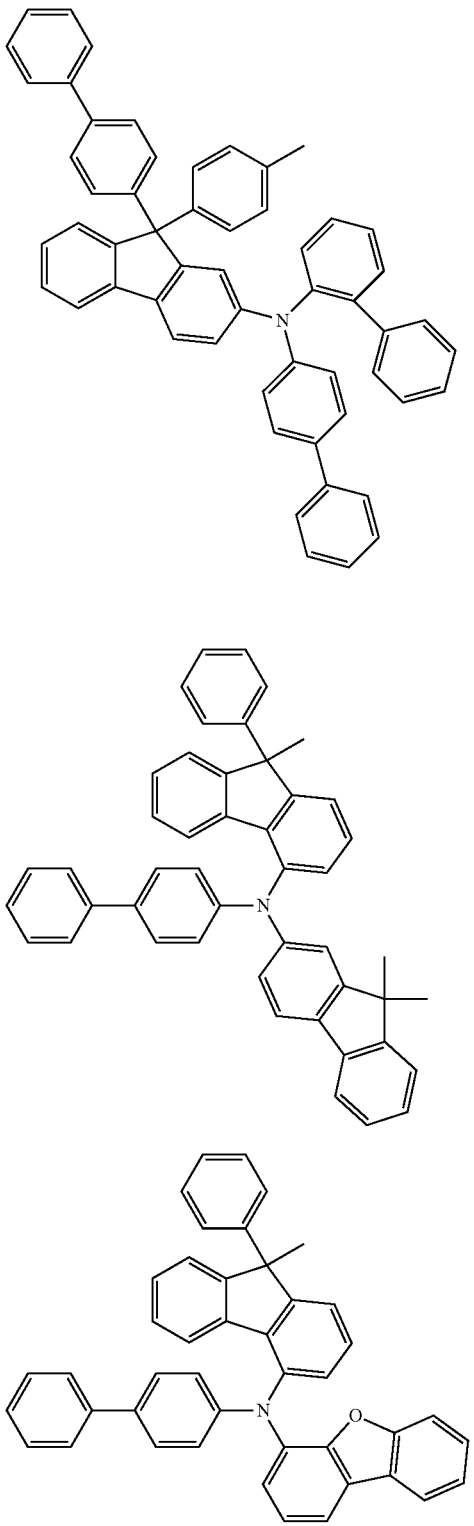

(2-1)

(2-8)

Materials HIL1, HIL2 (EP 0676461), H1 (WO 2008/145239), ETM1 (WO 2005/053055), SEB1 (WO 2008/006449), LiQ and NPB are well known to the person skilled in the art from the prior art. Compound HTMV1 can be prepared analogously to the synthesis shown in Example 1, where 2-bromo-9,9-dimethyl-9H-fluorene is converted in a Buchwald reaction with bisbiphenyl-4-ylamine. Compounds (2-7), (2-4), (2-5), (1-11), (2-1) and (2-8) are according to the invention.

Example 1

Synthesis of the compound biphenyl-2-ylbiphenyl-4-yl-(9-methyl-9-p-tolyl-9H-fluoren-2-yl)amine (1-1) and compounds (1-2) to (1-11)

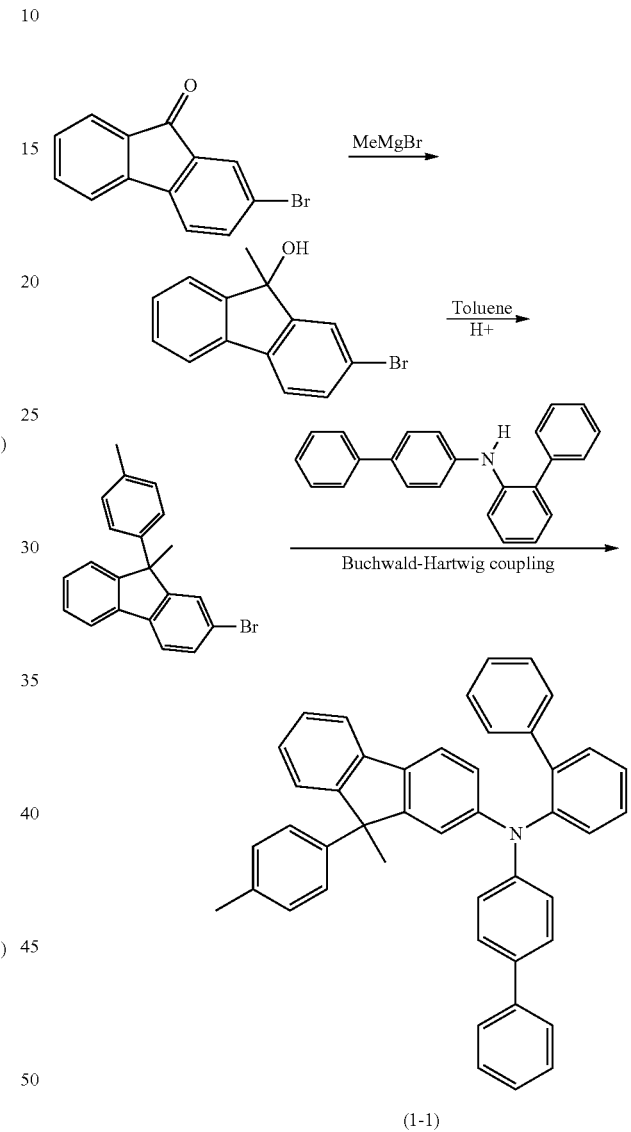

(1-1)

2-Bromo-9-methyl-9-p-tolyl-9H-fluorene 40 g (154 mmol) of 2-bromo-9H-fluorenone are dissolved in 500 ml of dried THF in a flask which has been dried by heating. The solution is saturated with $N_2$, and 15.0 g (170 mmol) of cerium(III) chloride are added. The clear solution is cooled to −10° C., and 121 ml (170 mmol) of a 1.4M methylmagnesium bromide solution are then added. The reaction mixture is slowly warmed to room temperature and then quenched using $NH_4Cl$ (500 ml). The mixture is subsequently partitioned between ethyl acetate and water, the organic phase is washed three times with water, dried over $Na_2SO_4$ and evaporated in a rotary evaporator. 60 ml of toluene are added to the evaporated solution. The batch is heated to 50° C., and 27.2 ml of trifluoromethanesulfonic acid (308 mmol) are subsequently added dropwise. After one hour, the reaction mixture is cooled to room temperature and poured into 1 l of water. The mixture is partitioned between toluene and water, the organic phase is washed three times with water and dried over Na$_2$SO$_4$ and evaporated in a rotary evaporator. Filtration of the crude product through silica gel with (heptane:ethyl acetate, 1:1) gave 32 g (60% of theory)

The following brominated compounds are prepared analogously:

| Starting material 1 | Starting material 2 | Starting material 3 | Product | Yield |
|---|---|---|---|---|
| 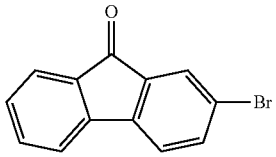 [SMILES: O=C1c2ccccc2-c2ccc(Br)cc21] | 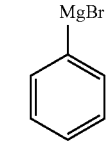 | 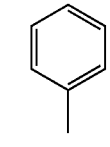 | 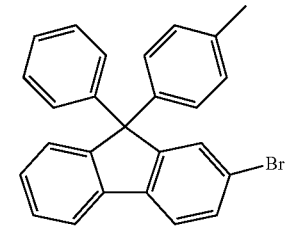 [SMILES: Cc1ccc(C2(c3ccccc3)c3ccccc3-c3ccc(Br)cc32)cc1] | 55% |
| 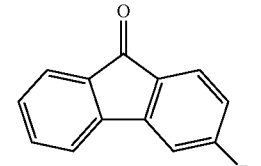 | 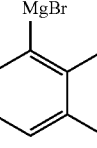 | 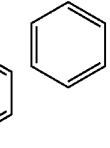 | 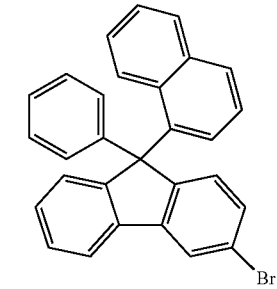 [SMILES: Brc1ccc2c(c1)-c1ccccc1C2(c1ccccc1)c1cccc2ccccc12] | 62% |
| 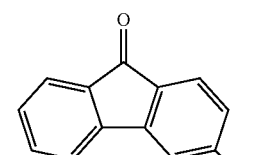 | 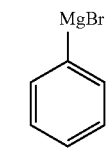 | 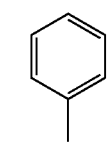 | 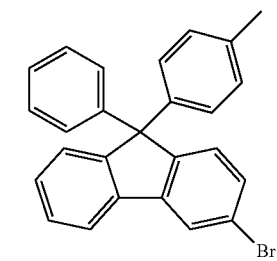 [SMILES: Cc1ccc(C2(c3ccccc3)c3ccccc3-c3cc(Br)ccc32)cc1] | 58% |
| 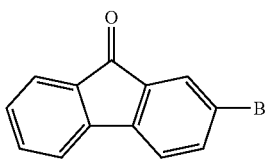 | 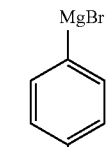 | 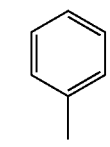 | 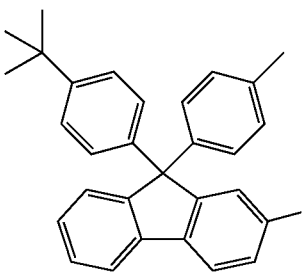 | 60% |
| 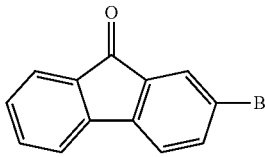 | 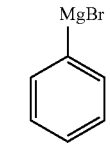 | 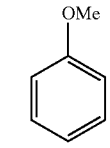 | 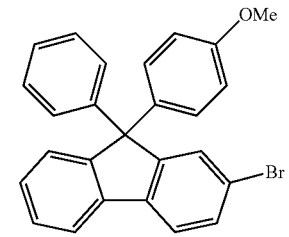 [SMILES: COc1ccc(C2(c3ccccc3)c3ccccc3-c3ccc(Br)cc32)cc1] | 52% |

-continued

| Starting material 1 | Starting material 2 | Starting material 3 | Product | Yield |
|---|---|---|---|---|
| 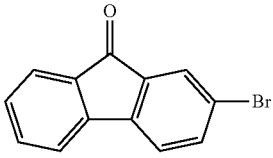 [SMILES: O=C1c2ccccc2-c2ccc(Br)cc21] |  |  | 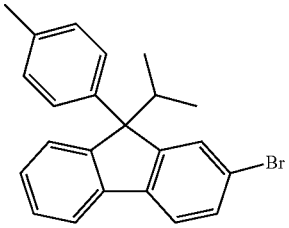 [SMILES: Cc1ccc(C2(C(C)C)c3ccccc3-c3ccc(Br)cc32)cc1] | 61% |
| 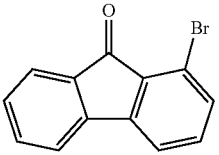 [SMILES: O=C1c2ccccc2-c2cccc(Br)c21] | MeMgBr |  | 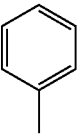 | 62% |
| 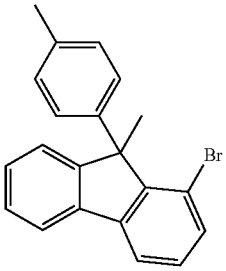 [SMILES: Cc1ccc(C2(C)c3ccccc3-c3cccc(Br)c32)cc1] | 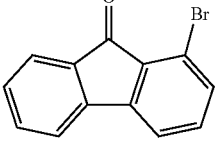 |  | 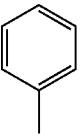 | 50% |
| 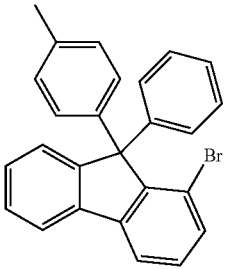 [SMILES: Cc1ccc(C2(c3ccccc3)c3ccccc3-c3cccc(Br)c32)cc1] | 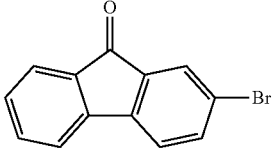 [SMILES: O=C1c2ccccc2-c2ccc(Br)cc21] | 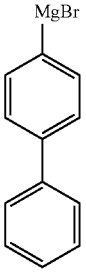 | 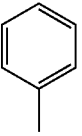 | 65% |

Biphenyl-2-ylbiphenyl-4-yl-(9-methyl-9-p-tolyl-9H-fluoren-2-yl)amine (1-1)

27.6 g of biphenyl-2-ylbiphenyl-4-ylamine (85.9 mmol), 30.0 g of 2-bromofluorene (85.9 mmol) are dissolved in 500 ml of toluene: the solution is degassed and saturated with $N_2$. 4.3 ml (4.3 mmol) of a 1 M tri-tert-butylphosphine solution and 0.48 g (2.15 mmol) of palladium(II) acetate are then added. 20.6 g of sodium tert-butoxide (214.7 mmol) are subsequently added. The reaction mixture is heated at the boil for 5 h under protective atmosphere. The mixture is subsequently partitioned between toluene and water, the organic phase is washed three times with water and dried over $Na_2SO_4$ and evaporated in a rotary evaporator. After filtration of the crude product through silica gel with toluene, the residue which remains is recrystallised from heptane/toluene and finally sublimed in a high vacuum, purity is 99.9%. The yield is 39.5 g (78% of theory).

121  122
Compounds (1.2) to (1-11) are prepared analogously:
| Starting material 1 | Starting material 2 | Product | Yield |
|---|---|---|---|
| 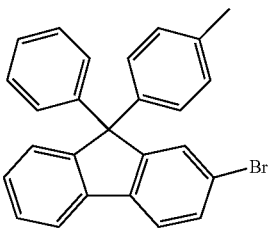 [SMILES: Cc1ccc(C2(c3ccccc3)c3ccccc3-c3ccc(Br)cc32)cc1] | 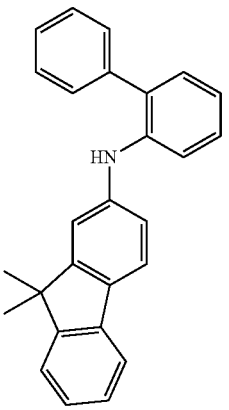 [SMILES: CC1(C)c2ccccc2-c2ccc(Nc3ccccc3-c3ccccc3)cc21] | 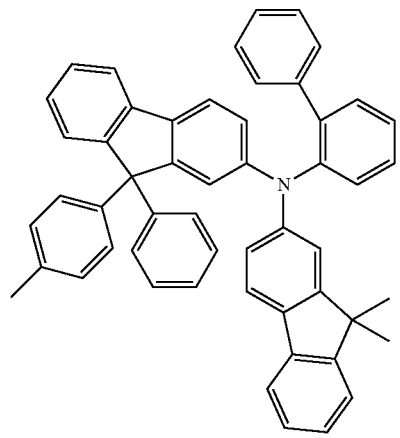 (1-2) | 78% |
| 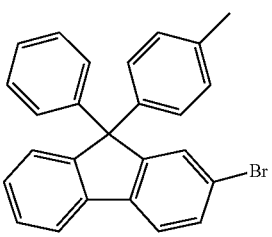 [SMILES: Cc1ccc(C2(c3ccccc3)c3ccccc3-c3ccc(Br)cc32)cc1] | 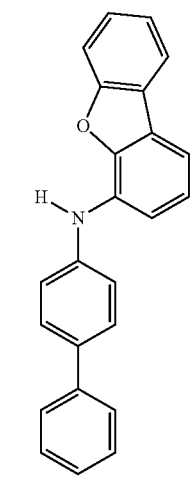 [SMILES: c1ccc(-c2ccc(Nc3cccc4c3oc3ccccc34)cc2)cc1] | 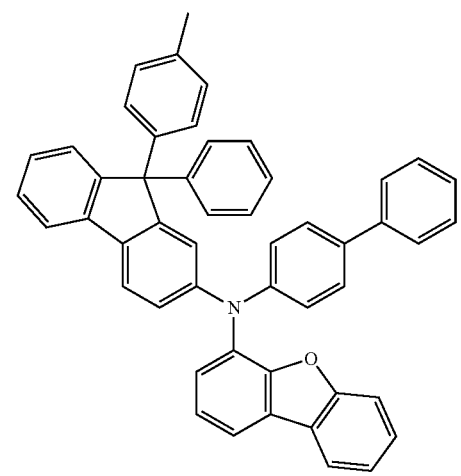 (1-3) | 92% |
| 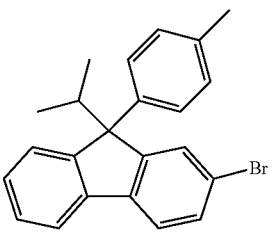 [SMILES: Cc1ccc(C2(C(C)C)c3ccccc3-c3ccc(Br)cc32)cc1] | 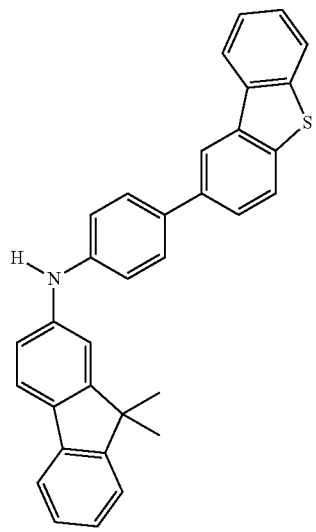 [SMILES: CC1(C)c2ccccc2-c2ccc(Nc3ccc(-c4ccc5sc6ccccc6c5c4)cc3)cc21] | 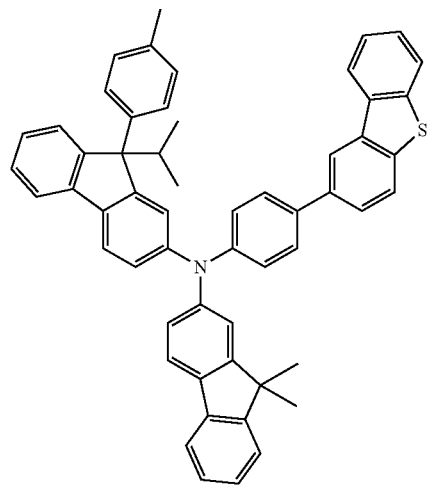 (1-4) | 88% |

-continued
| Starting material 1 | Starting material 2 | Product | Yield |
|---|---|---|---|
| 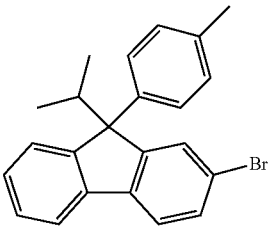 [SMILES: Cc1ccc(C2(C(C)C)c3ccccc3-c3ccc(Br)cc32)cc1] | 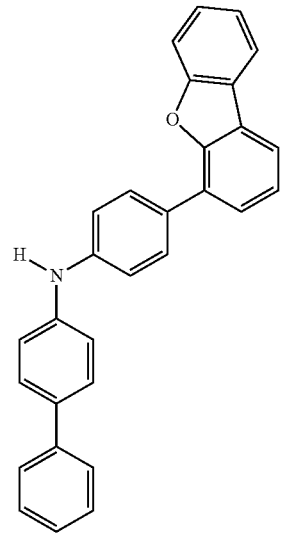 [SMILES: c1ccc(-c2ccc(Nc3ccc(-c4cccc5c4oc4ccccc45)cc3)cc2)cc1] | 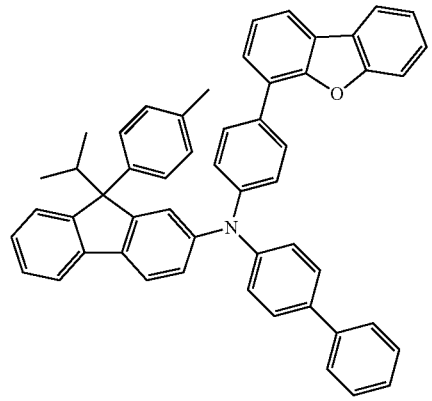<br>(1-5) | 85% |
| 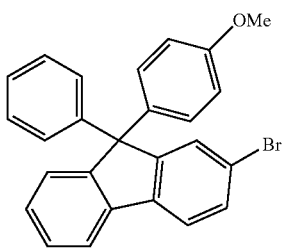 [SMILES: COc1ccc(C2(c3ccccc3)c3ccccc3-c3ccc(Br)cc32)cc1] | 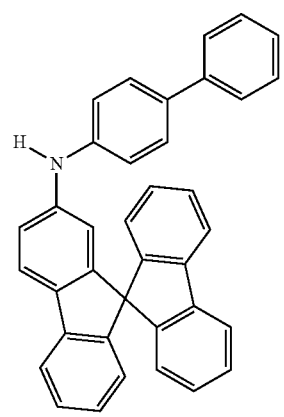 [SMILES: c1ccc(-c2ccc(Nc3ccc4c(c3)C3(c5ccccc5-c5ccccc53)c3ccccc3-4)cc2)cc1] | 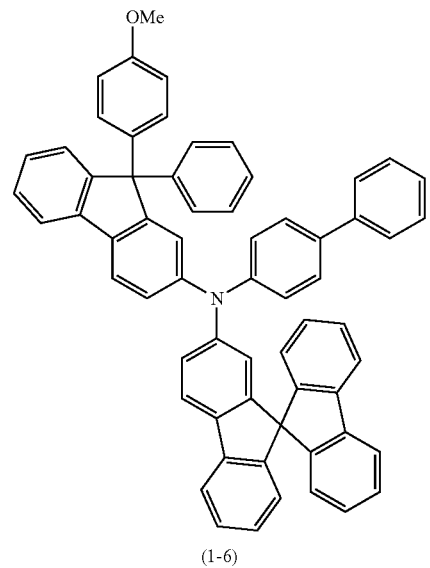 [SMILES: COc1ccc(C2(c3ccccc3)c3ccccc3-c3ccc(N(c4ccc(-c5ccccc5)cc4)c4ccc5c(c4)C4(c6ccccc6-c6ccccc64)c4ccccc4-5)cc32)cc1]<br>(1-6) | 80% |

-continued

| Starting material 1 | Starting material 2 | Product | Yield |
|---|---|---|---|
| | | (1-7) | 75% |
| | | (1-8) | 75% |
| | | (1-9) | 80% |

-continued
| Starting material 1 | Starting material 2 | Product | Yield |
|---|---|---|---|
| | | | 70% |
| | | (1-10) | |
| | | | 75% |
| | | (1-11) | |
Example 2
Synthesis of the compound biphenyl-4-yl-(9,9-dimethyl-9H-fluoren-2-yl)-(9-methyl-9-phenyl-9H-fluoren-4-yl)amine (2-1) and compounds (2-2) to (2-8)
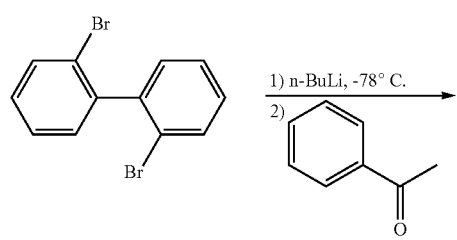

-continued

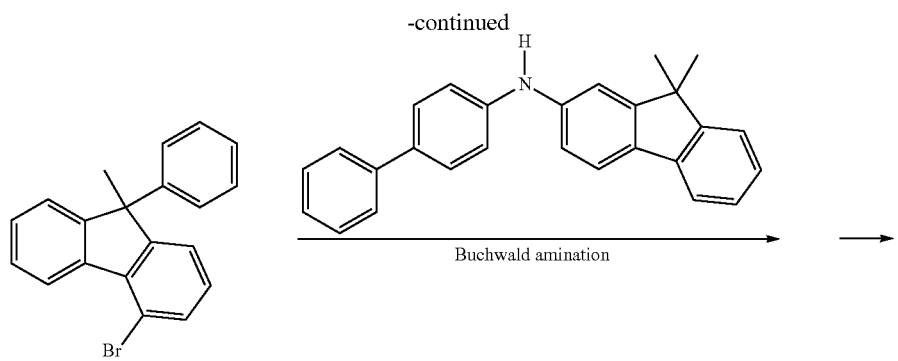

→ Buchwald amination →

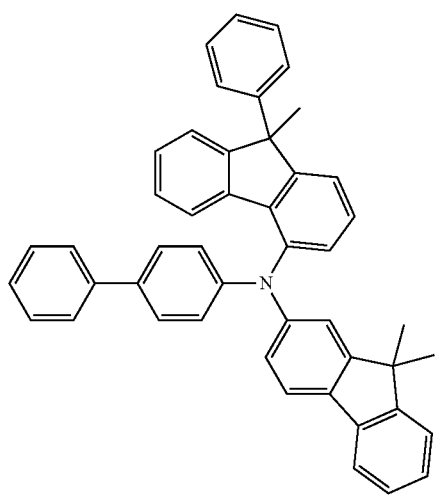

(2-1)

4-Bromo-9-methyl-9-phenyl-9H-fluorene 30 g (94 mmol) of 2,2'-dibromobiphenyl are dissolved in 200 ml of dried THF in a flask which has been dried by heating. The reaction mixture is cooled to −78° C. 37.7 ml of a 2.5 M solution of n-BuLi in hexane (94 mmol) are slowly added dropwise (duration: about 1 h) at this temperature. The batch is stirred at −70° C. for a further 1 h. 11.1 ml of acetophenone (94 mmol) are subsequently dissolved in 100 ml of THF and added dropwise at −70° C. When the addition is complete, the reaction mixture is slowly warmed to room temperature, quenched using $NH_4Cl$ and subsequently evaporated in a rotary evaporator. 300 ml of acetic acid are carefully added to the evaporated solution, and 50 ml of fuming HCl are subsequently added. The batch is heated to 75° C. and held there for 6 h. A white solid precipitates out during this time. The batch is then cooled to room temperature, the solid which has precipitated out is filtered off with suction and rinsed with methanol. The residue is dried at 40° C. in vacuo. Yield is 25.3 g (75 mmol) (80% of theory)

The following brominated compounds are prepared analogously.

| Starting material 1 | Starting material 2 | Product | Yield |
|---|---|---|---|
| Br-C6H5 | 4'-bromo-2-acetylbiphenyl | 2-bromo-9-methyl-9-phenyl-9H-fluorene | 78% |

| Starting material 1 | Starting material 2 | Product | Yield |
|---|---|---|---|
| 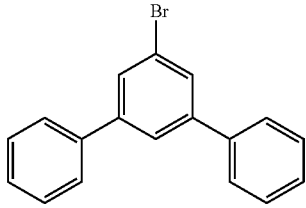 [SMILES: Brc1cc(-c2ccccc2)cc(-c2ccccc2)c1] | 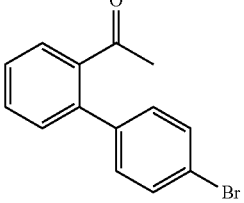 | 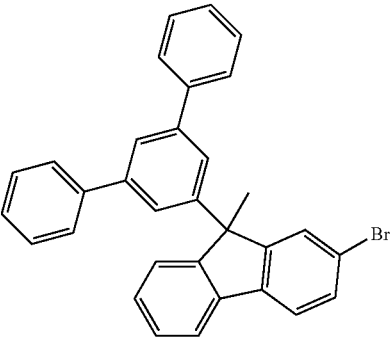 [SMILES: CC1(c2cc(-c3ccccc3)cc(-c3ccccc3)c2)c2ccccc2-c2ccc(Br)cc21] | 80% |
| 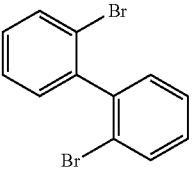 [SMILES: Brc1ccccc1-c1ccccc1Br] | 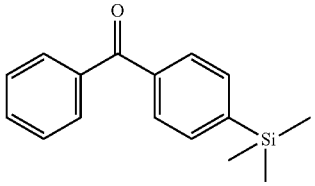 [SMILES: C[Si](C)(C)c1ccc(C(=O)c2ccccc2)cc1] | 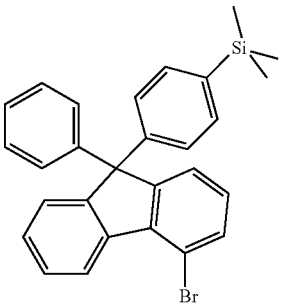 [SMILES: C[Si](C)(C)c1ccc(C2(c3ccccc3)c3ccccc3-c3c(Br)cccc32)cc1] | 87% |

Biphenyl-4-yl-(9,9-dimethyl-9H-fluoren-2-yl)-(9-methyl-9-phenyl-9H-fluoren-4-yl)amine (2-1)

17.8 g of biphenyl-2-ylbiphenyl-4-ylamine (49.4 mmol), 18.2 g of 2.bromo-(9-methyl-9-phenyl-9H-fluorene (54.3 mol) are dissolved in 400 ml of toluene: the solution is degassed and saturated with $N_2$. 2.96 ml (2.96 mmol) of tri-tert-butylphosphine and 0.33 g (1.48 mmol) of palladium (II) acetate are then added, and 9.8 g of sodium tert-butoxide (98.8 mmol) are subsequently added. The reaction mixture is heated at the boil for 3 h under protective atmosphere. The mixture is subsequently partitioned between toluene and water, the organic phase is washed three times with water, dried over $Na_2SO_4$ and evaporated in a rotary evaporator. After filtration of the crude product through silica gel with toluene, the residue which remains is recrystallised from heptane/toluene and finally sublimed in a high vacuum, purity is 99.9%. The yield is 24.3 g (80% of theory).

Compounds (2-2) to (2-8) are prepared analogously:

| Starting material 1 | Starting material 2 | Product | Yield |
|---|---|---|---|
| 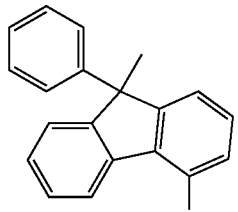 | 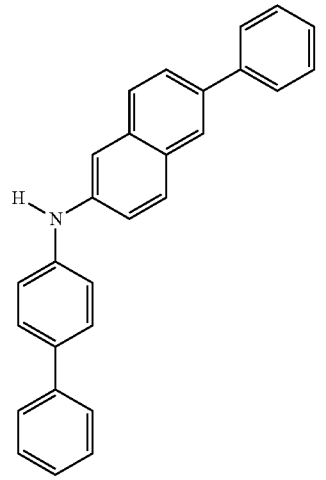 [SMILES: c1ccc(-c2ccc(Nc3ccc4cc(-c5ccccc5)ccc4c3)cc2)cc1] | 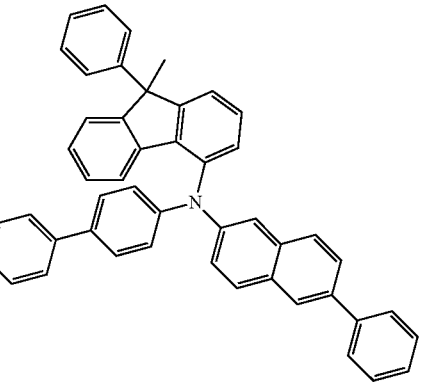 | 78% |

(2-2)

-continued
| Starting material 1 | Starting material 2 | Product | Yield |
|---|---|---|---|
| 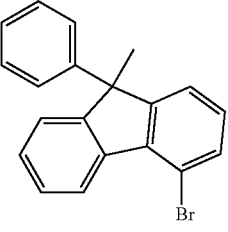 [SMILES: CC1(c2ccccc2)c2ccccc2-c2c(Br)cccc21] | 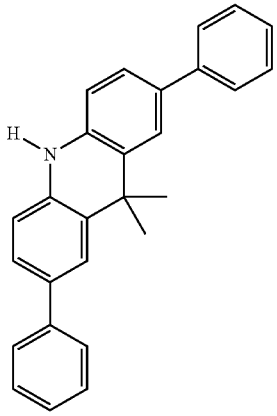 [SMILES: CC1(C)c2cc(-c3ccccc3)ccc2Nc2ccc(-c3ccccc3)cc21] | 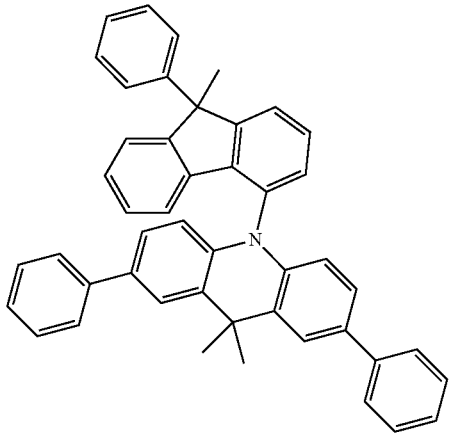<br>(2-3) | 75% |
| 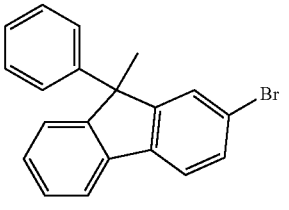 [SMILES: CC1(c2ccccc2)c2ccccc2-c2ccc(Br)cc21] | 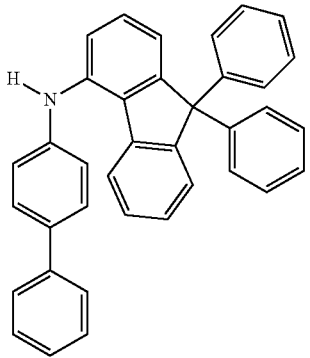 [SMILES: c1ccc(-c2ccc(Nc3cccc4c3-c3ccccc3C4(c3ccccc3)c3ccccc3)cc2)cc1] | 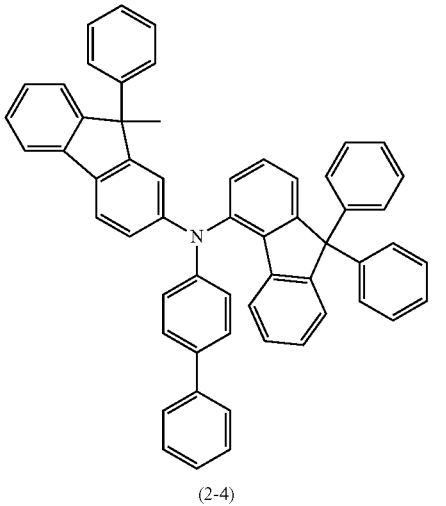 [SMILES: CC1(c2ccccc2)c2ccccc2-c2ccc(N(c3ccc(-c4ccccc4)cc3)c3cccc4c3-c3ccccc3C4(c3ccccc3)c3ccccc3)cc21]<br>(2-4) | 80% |
| 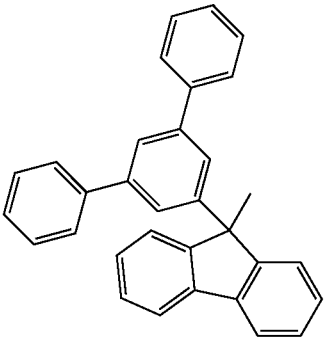 [SMILES: CC1(c2cc(-c3ccccc3)cc(-c3ccccc3)c2)c2ccccc2-c2ccccc21] | 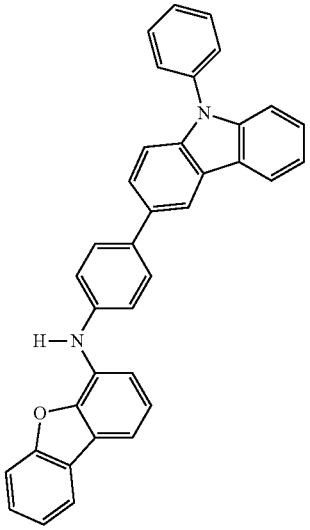 [SMILES: c1ccc(-n2c3ccccc3c3cc(-c4ccc(Nc5cccc6c5oc5ccccc56)cc4)ccc32)cc1] | 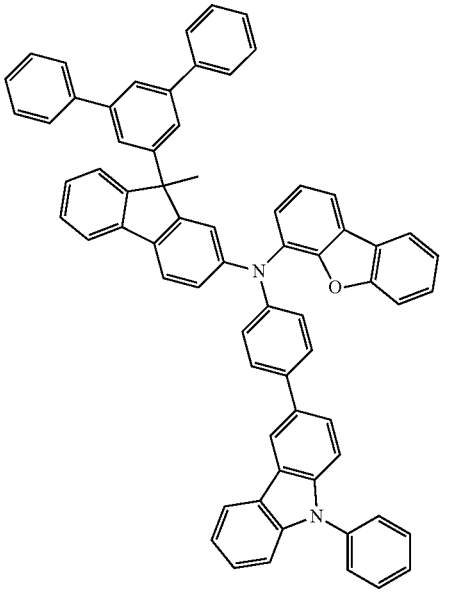<br>(2-5) | 80% |

-continued
| Starting material 1 | Starting material 2 | Product | Yield |
|---|---|---|---|
| 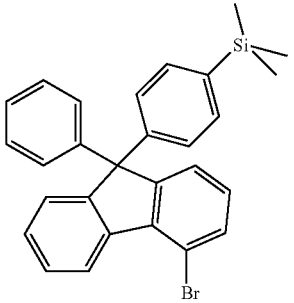 [SMILES: C[Si](C)(C)c1ccc(C2(c3ccccc3)c3ccccc3-c3c(Br)cccc32)cc1] | 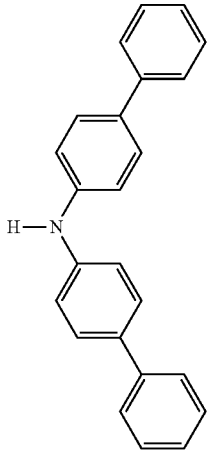 [SMILES: c1ccc(-c2ccc(Nc3ccc(-c4ccccc4)cc3)cc2)cc1] | 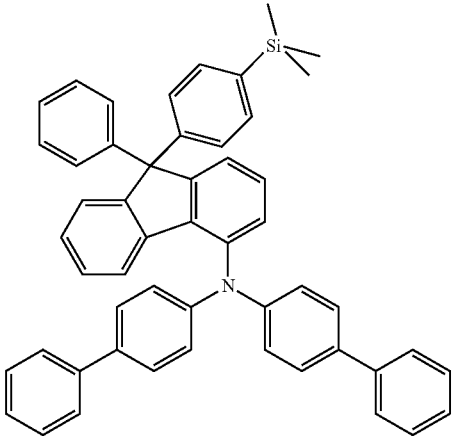
(2-6) | 88% |
| 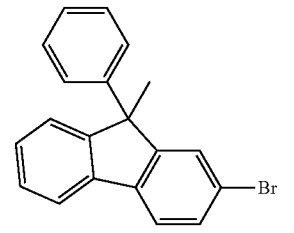 [SMILES: CC1(c2ccccc2)c2ccccc2-c2ccc(Br)cc21] | 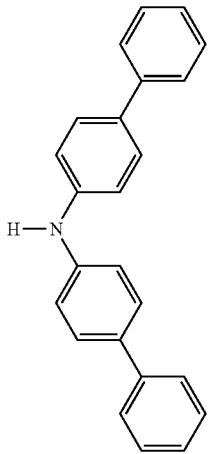 [SMILES: c1ccc(-c2ccc(Nc3ccc(-c4ccccc4)cc3)cc2)cc1] | 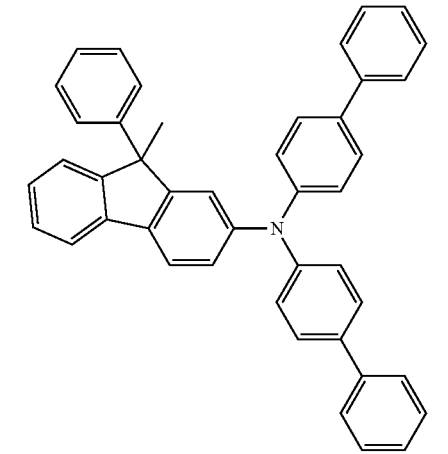
(2-7) | 85% |
| 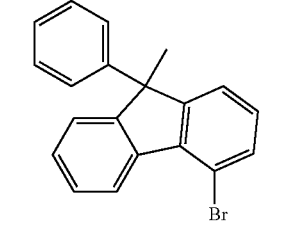 [SMILES: CC1(c2ccccc2)c2ccccc2-c2c(Br)cccc21] | 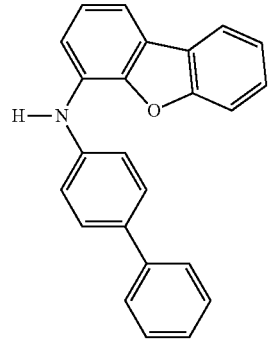 [SMILES: c1ccc(-c2ccc(Nc3cccc4c3oc3ccccc34)cc2)cc1] | 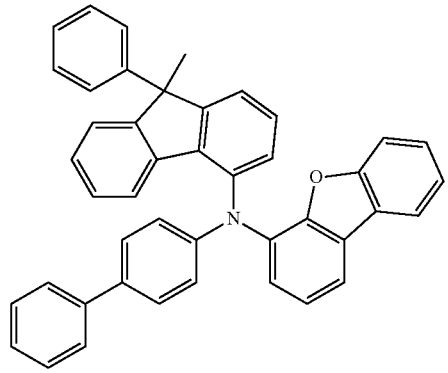
(2-8) | 78% |

Example 3

Synthesis of the compound biphenyl-4-ylbiphenyl-2-yl-(7,9-diphenyl-9-p-tolyl-9H-fluoren-2-yl)amine (3-1) and compounds (3-2) to (3-4)

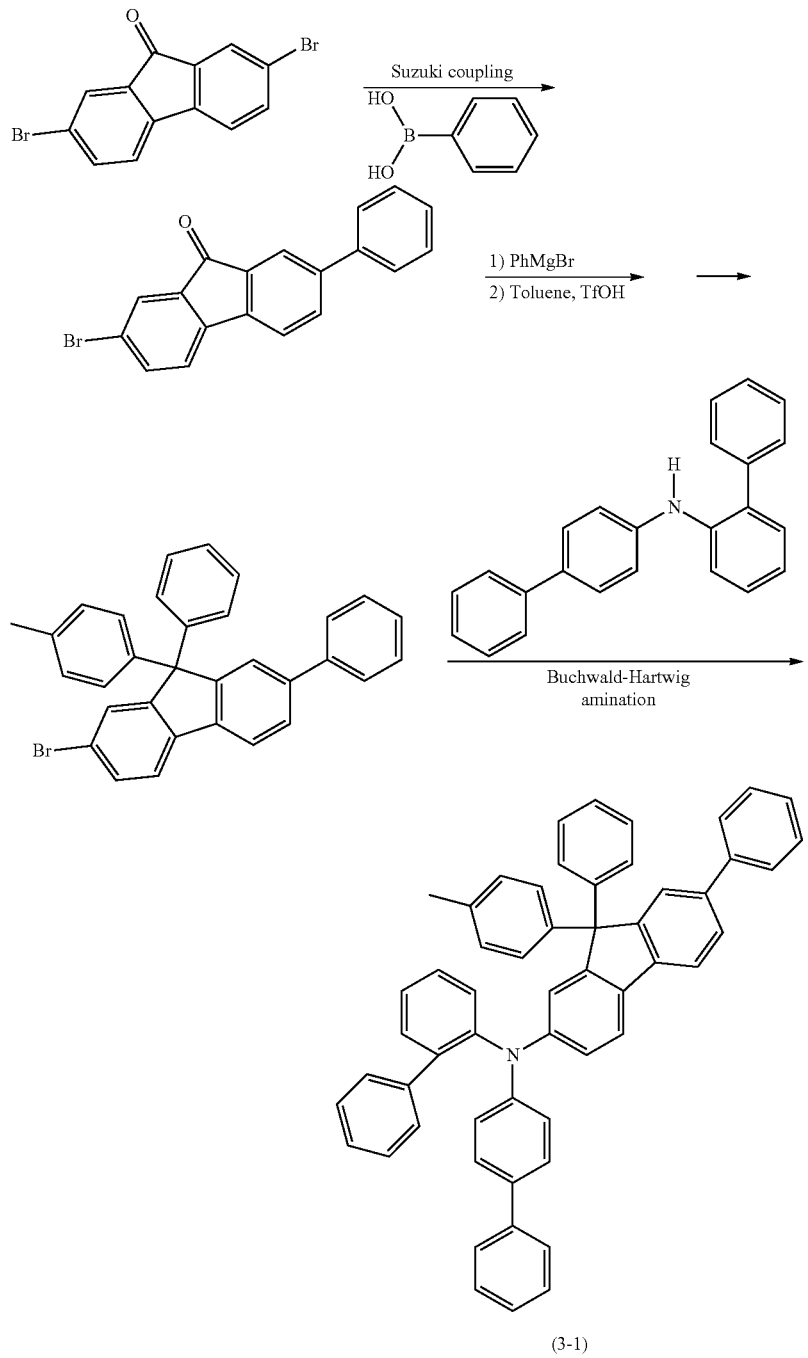

(3-1)

2-Bromo-7-phenylfluoren-9-one 21.6 g (178 mmol) of phenylboronic acid, 60 g (178 mmol) of 2,7-dibromo-fluorenone are suspended in 800 ml of dimethoxyethane and 265 ml of a 2 M sodium carbonate solution (533 mmol). 6.154 g (5 mmol) of tetrakis-(triphenylphosphine)palladium are added to this suspension, and the reaction mixture is heated under reflux for 18 h. After cooling of the reaction mixture, the organic phase is separated off, filtered through silica gel, washed three times with 100 ml of water and subsequently evaporated to dryness.

Filtration of the crude product through silica gel with toluene gives 38.6 g (85%) of 2-bromo-7-phenylfluoren-9-one.

The following brominated compounds are prepared analogously:

| Starting material 1 | Starting material 2 | Product | Yield |
|---|---|---|---|
|  |  | 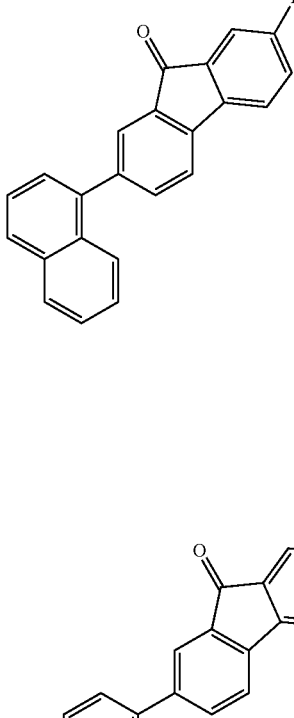 | 85% |
| 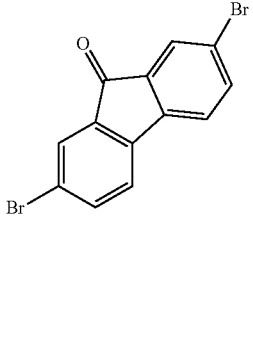 [SMILES: O=C1c2cc(Br)ccc2-c2ccc(Br)cc21] | 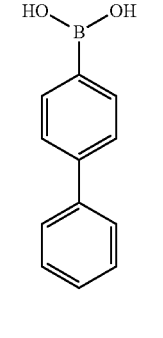 | 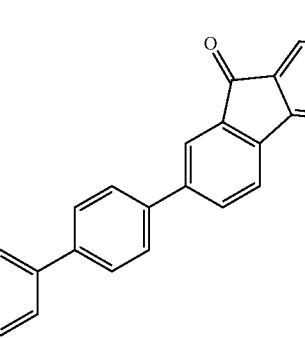 | 90% |

2-Bromo-7,9-diphenyl-9-p-tolyl-9H-fluorene 35 g (104 mmol) of 2-bromo-7-phenylfluorenone are dissolved in 600 ml of dried THF in a flask which has been dried by heating. The clear solution is cooled to −10° C., and 38.3 ml (115 mmol) of a 3 M phenylmagnesium bromide solution are then added. The reaction mixture is slowly warmed to room temperature and then quenched using NH₄Cl (300 ml). The mixture is subsequently partitioned between ethyl acetate and water, the organic phase is washed three times with water, dried over Na₂SO₄ and evaporated in a rotary evaporator. 100 ml of toluene are added to the evaporated solution. The batch is heated to 50° C., and 20.4 ml of trifluoromethanesulfonic acid (208 mmol) are subsequently added dropwise. After one hour, the reaction mixture is cooled to room temperature and poured into 1 l of water. The mixture is partitioned between toluene and water, the organic phase is washed three times with water and dried over Na₂SO₄ and evaporated in a rotary evaporator. Filtration of the crude product through silica gel with (heptane: ethyl acetate, 1:1) gives 41 g (61% of theory).

The following brominated compounds are prepared analogously:

| Starting material 1 | Starting material 2 | Starting material 3 | Product | Yield |
|---|---|---|---|---|
| 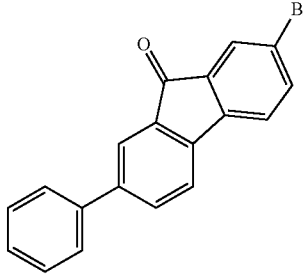 | 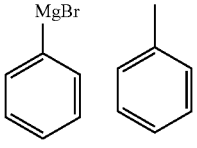 | 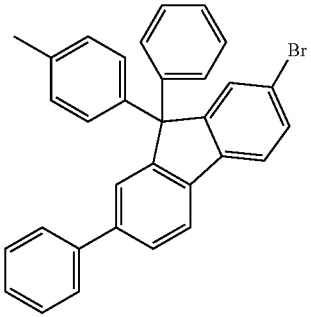 [SMILES: Cc1ccc(C2(c3ccccc3)c3cc(Br)ccc3-c3ccc(-c4ccccc4)cc32)cc1] | 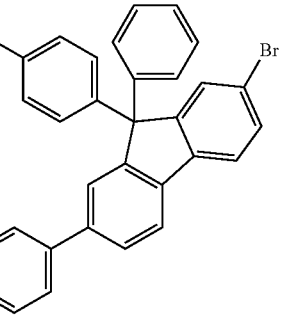 | 60% |

-continued

| Starting material 1 | Starting material 2 | Starting material 3 | Product | Yield |
|---|---|---|---|---|
| [2-bromo-7-(naphthalen-1-yl)-9H-fluoren-9-one] | PhMgBr | toluene | [9-(p-tolyl)-9-phenyl-2-bromo-7-(naphthalen-1-yl)fluorene] | 55% |
| [2-bromo-7-(biphenyl-4-yl)-9H-fluoren-9-one] | CH3MgBr | toluene | [9-methyl-9-(p-tolyl)-2-bromo-7-(biphenyl-4-yl)fluorene] | 60% |

Biphenyl-4-ylbiphenyl-2-yl-(7,9-diphenyl-9-p-tolyl-9H-fluoren-2-yl)amine (3-1)

13.18 g of biphenyl-2-ylbiphenyl-4-ylamine (41 mmol), 20 g of 2-bromo-7,9-diphenyl-9-p-tolyl-9H-fluorene (41 mmol) are dissolved in 350 ml of toluene: the solution is degassed and saturated with $N_2$. 1.6 ml (1.6 mmol) of tri-tert-butylphosphine and 184 mg (0.82 mmol) of palladium(II) acetate are then added. 9.86 g of sodium tert-butoxide (102 mmol) are subsequently added. The reaction mixture is heated at the boil for 5 h under protective atmosphere. The mixture is subsequently partitioned between toluene and water, the organic phase is washed three times with water, dried over $Na_2SO_4$ and evaporated in a rotary evaporator. After filtration of the crude product through silica gel with toluene, the residue which remains is recrystallised from heptane/toluene and finally sublimed in a high vacuum. The purity is 99.9%. The yield is 21.8 g (73% of theory).

The following compounds are prepared analogously:

| Starting material 1 | Starting material 2 | Product | Yield |
|---|---|---|---|
| [2-bromo-9-(p-tolyl)-9-phenyl-7-phenyl-fluorene] | [N-(biphenyl-4-yl)-biphenyl-4-ylamine] | [product (3-2)] | 85% |

(3-2)

| Starting material 1 | Starting material 2 | Product | Yield |
|---|---|---|---|
| | | | 82% (3-3) |
| | | | 80% (3-4) |

Example 4

Characterisation of the Compounds

OLEDs according to the invention and OLEDs in accordance with the prior art are produced by a general process in accordance with WO 04/058911, which is adapted to the circumstances described here (e.g. layer-thickness variation, materials).

The data of various OLEDs are presented in the following examples V1, V2 and E1 to E3 (see Tables 1 and 2). The substrates used are glass plates which have been coated with structured ITO (indium tin oxide) in a thickness of 50 nm. The OLEDs basically have the following layer structure: substrate/hole-injection layer (HIL1)/hole-transport layer (HTL)/hole-injection layer (HIL2)/electron-blocking layer (EBL)/emission layer (EML)/electron-transport layer (ETL)/electron-injection layer (EIL) and finally a cathode. The cathode is formed by an aluminium layer with a thickness of 100 nm. The precise structure of the OLEDs is shown in Table 1. The materials required for the production of the OLEDs are indicated above.

All materials are applied by thermal vapour deposition in a vacuum chamber. The emission layer here always consists of at least one matrix material (host material) and an emitting dopant (emitter) with which the matrix material or matrix materials is (are) admixed in a certain proportion by volume by co-evaporation. An expression such as H1:SEB1 (95%:5%) here means that material H1 is present in the layer in a proportion by volume of 95% and SEB1 is present in the layer in a proportion of 5%. Analogously, the electron-transport layer may also consist of a mixture of two materials.

The OLEDs are characterised by standard methods. For this purpose, the electroluminescence spectra, the current efficiency (measured in cd/A), the power efficiency (measured in lm/W) and the external quantum efficiency (EQE, measured in per cent) as a function of the luminous density, calculated from current/voltage/luminous density characteristic lines (IUL characteristic lines) assuming Lambert emission characteristics, and the lifetime are determined. The electroluminescence spectra are determined at a luminous density of 1000 cd/m$^2$, and the CIE 1931 x and y colour coordinates are calculated therefrom. The expression EQE @ 1000 cd/m$^2$ denotes the external quantum efficiency at an operating luminous density of 1000 cd/m$^2$. LT80 @

6000 cd/m² is the lifetime by which the OLED at a luminosity of 6000 cd/m² has dropped to 80% of the initial intensity, i.e. to 4800 cd/m². The data of the various OLEDs are summarised in Table 2.

Use of Compounds According to the Invention as Hole-transport Materials in Fluorescent OLEDs Compounds according to the invention are particularly suitable as HIL, HTL or EBL in OLEDs. They are suitable as a single layer, but also as mixed component as HIL, HTL, EBL or within the EML.

Compared with NPB reference components (V1), the samples comprising the compounds according to the invention exhibit both higher efficiencies and also significantly improved lifetimes in singlet blue.

Compared with reference material HTMV1 (V2), compounds (2-7), (2-4), (2-5), (1-11), (2-1) and (2-8) according to the invention (E1-E4) have a better lifetime.

In green triplet components, compounds (2-7), (2-4), (2-1) according to the invention exhibit better efficiencies and better lifetimes compared with reference components V3 (NPB) and V4 (HTMV1).

TABLE 1

Structure of the OLEDs
(Layer structure: substrate/IL/HTL/IL/EBL/EML/ETL/EIL (1 nm LiQ)/cathode)

| Ex. | HIL1 Thickness/nm | HTL Thickness/nm | HIL2 Thickness/nm | EBL Thickness/nm | EML Thickness/nm | ETL Thickness/nm |
|---|---|---|---|---|---|---|
| V1 | HIL1 5 nm | HIL2 140 nm | HIL1 5 nm | NPB 20 nm | H1(95%):SEB1(5%) 20 nm | ETM1(50%):LiQ(50%) 30 nm |
| V2 | HIL1 5 nm | HIL2 140 nm | HIL1 5 nm | HTMV1 20 nm | H1(95%):SEB1(5%) 20 nm | ETM1(50%):LiQ(50%) 30 nm |
| E1 | HIL1 5 nm | HIL2 140 nm | HIL1 5 nm | (2-7) 20 nm | H1(95%):SEB1(5%) 20 nm | ETM1(50%):LiQ(50%) 30 nm |
| E2 | HIL1 5 nm | HIL2 140 nm | HIL1 5 nm | (2-4) 20 nm | H1(95%):SEB1(5%) 20 nm | ETM1(50%):LiQ(50%) 30 nm |
| E3 | HIL1 5 nm | HIL2 140 nm | HIL1 5 nm | (2-5) 20 nm | H1(95%):SEB1(5%) 20 nm | ETM1(50%):LiQ(50%) 30 nm |
| E4 | HIL1 5 nm | HIL2 140 nm | HIL1 5 nm | (1-11) 20 nm | H1(95%):SEB1(5%) 20 nm | ETM1(50%):LiQ(50%) 30 nm |
| E5 | HIL1 5 nm | HIL2 140 nm | HIL1 5 nm | (2-1) 20 nm | H1(95%):SEB1(5%) 20 nm | ETM1(50%):LiQ(50%) 30 nm |
| E6 | HIL1 5 nm | HIL2 140 nm | HIL1 5 nm | (2-8) 20 nm | H1(95%):SEB1(5%) 20 nm | ETM1(50%):LiQ(50%) 30 nm |

TABLE 2

Data of the OLEDs

| Ex. | EQE @ 1000 cd/m2 % | LT80 @ 6000 cd/m² [h] | CIE x | CIE y |
|---|---|---|---|---|
| V1 | 4.8 | 70 | 0.14 | 0.17 |
| V2 | 7.0 | 130 | 0.13 | 0.15 |
| E1 | 6.1 | 155 | 0.13 | 0.15 |
| E2 | 7.0 | 161 | 0.14 | 0.15 |
| E3 | 6.9 | 158 | 0.13 | 0,14 |
| E4 | 8.5 | 155 | 0.13 | 0.15 |
| E5 | 7.0 | 155 | 0.14 | 0.15 |
| E6 | 6.9 | 160 | 0.14 | 0.15 |

TABLE 3

Structure of the OLEDs
(Layer structure: substrate/HTL/HIL2/EBL/EML/ETL/cathode)

| Ex. | HTL Thickness/nm | HIL2 Thickness/nm | EBL Thickness/nm | EML Thickness/nm | ETL Thickness/nm |
|---|---|---|---|---|---|
| V3 | HIL2 70 nm | HIL1 5 nm | NPB 20 nm | H2(88%):Irpy(12%) 30 nm | ETM1(50%):LiQ(50%) 40 nm |
| V4 | HIL2 70 nm | HIL1 5 m | HTMV1 20 nm | H2(88%):Irpy(12%) 30 nm | ETM1(50%):LiQ(50%) 40 nm |
| E7 | HIL2 70 nm | HIL1 5 nm | (2-7) 20 nm | H2(88%):Irpy(12%) 30 nm | ETM1(50%):LiQ(50%) 40 nm |
| E8 | HIL2 70 nm | HIL1 5 nm | (2-4) 20 nm | H2(88%):Irpy(12%) 30 nm | ETM1(50%):LiQ(50%) 40 nm |
| E9 | HIL2 70 nm | HIL1 5 nm | (2-1) 20 nm | H2(88%):Irpy(12%) 30 nm | ETM1(50%):LiQ(50%) 40 nm |

TABLE 4

| | Data of the OLEDs | | | |
|---|---|---|---|---|
| | Efficiency @ 1000 cd/m2 | LT80 @ 8000 cd/m² | CIE | |
| Ex. | % | [h] | x | Y |
| V3 | 13.4 | 85 | 0.36 | 0.61 |
| V4 | 17.0 | 170 | 0.35 | 0.62 |
| E7 | 17.5 | 190 | 0.34 | 0.62 |
| E8 | 18.3 | 215 | 0.35 | 0.62 |
| E9 | 18.5 | 225 | 0.37 | 0.60 |

The invention claimed is:

1. An electroluminescent device comprising at least one compound of the general formula (2)

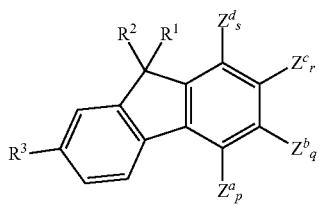

formula (2)

where the following applies to the symbols and indices used:

p, q, r, s
  are 0 or 1, where p+q+r+s=1;

$Z^a_0$, $Z^b_0$, $Z^c_0$, $Z^d_0$
  are, identically or differently on each occurrence, equal to $R^4$ $Z^a_1$, $Z^b_1$, $Z^c_1$, $Z^d_1$ are equal to

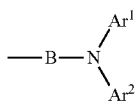

B
  is a single bond, a divalent aryl group having 6 to 30 ring atoms or a divalent heteroaryl group having 5 to 30 ring atoms, each of which is optionally substituted by one or more radicals $R^6$, where, if B is a single bond, the nitrogen atom is bonded directly to the fluorene;

$Ar^1$ and $Ar^2$ are selected, identically or differently on each occurrence, from the following groups of the formulae (42) to (107), (119)-(121) and (123)-(142)

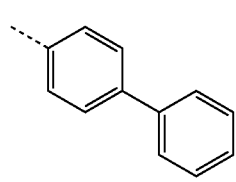

formula (42)

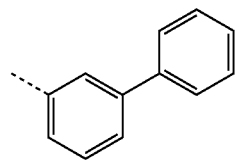

formula (43)

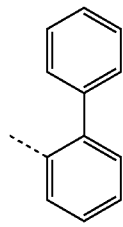

formula (44)

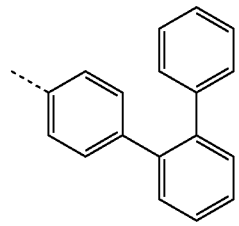

formula (45)

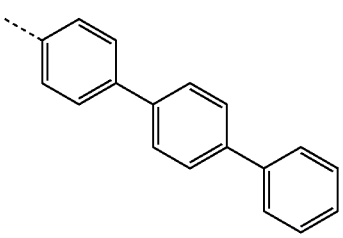

formula (46)

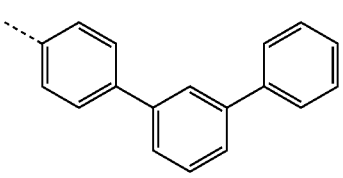

formula (47)

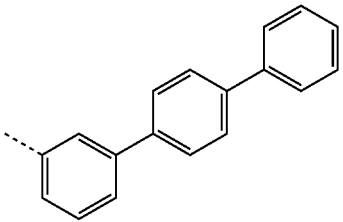

formula (48)

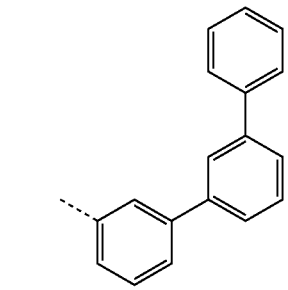

formula (49)

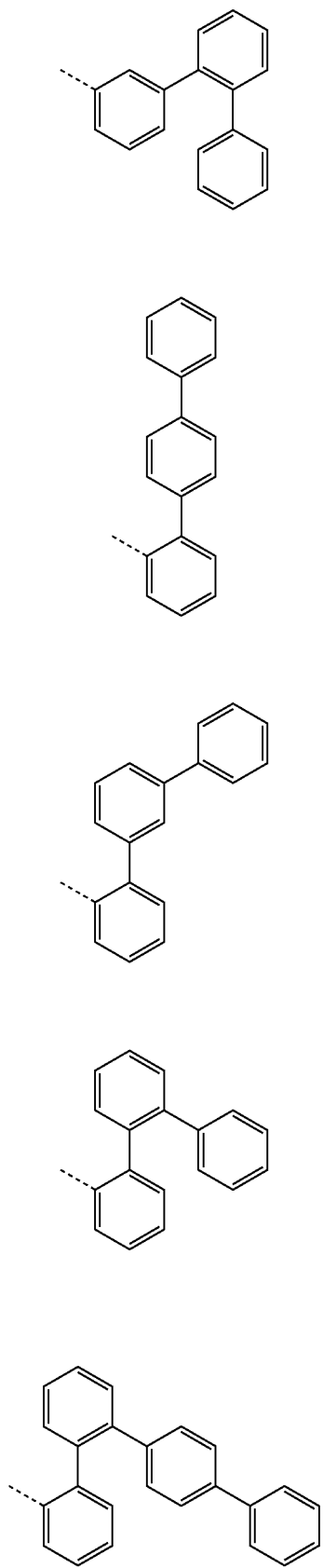
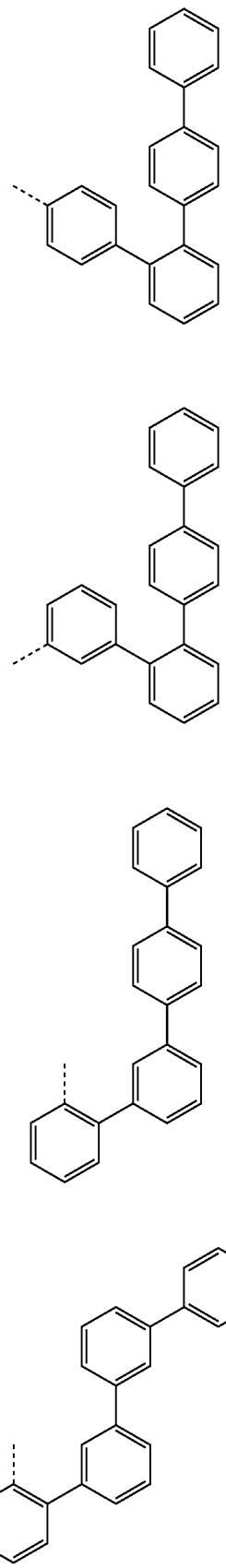
formula (50)
formula (51)
formula (52)
formula (53)
formula (54)
formula (55)
formula (56)
formula (57)
formula (58)

formula (59)
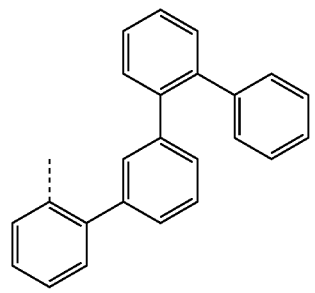
formula (60)
formula (61)
formula (62)
formula (63)
formula (64)
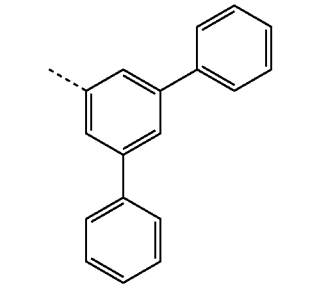
formula (65)
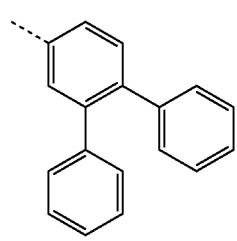
formula (66)
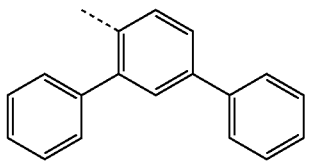
formula (67)
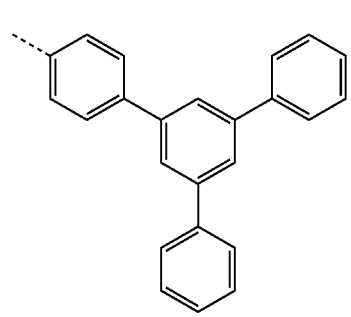
formula (68)
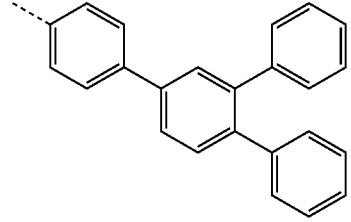
formula (69)
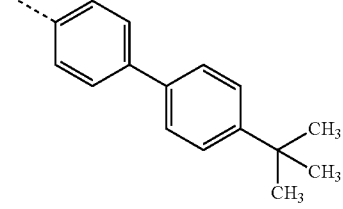
formula (70)
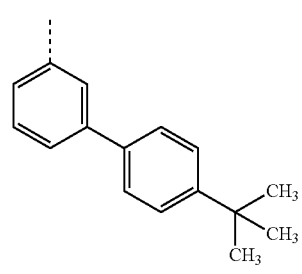

-continued
formula (71)
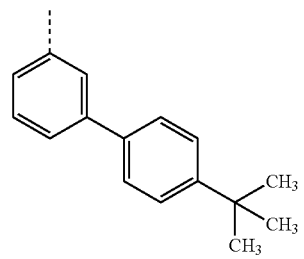
formula (72)
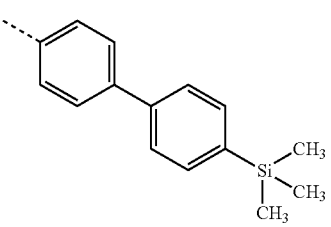
formula (73)
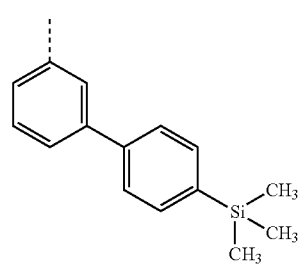
formula (74)
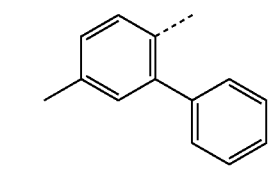
formula (75)
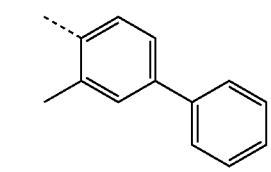
formula (76)
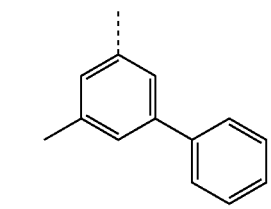
formula (77)
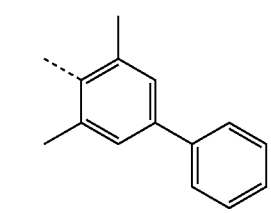
formula (78)
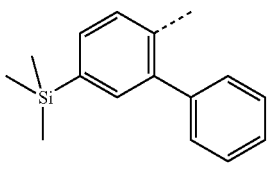
formula (79)
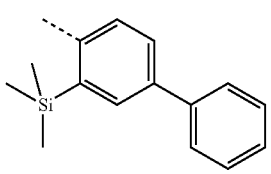
formula (80)
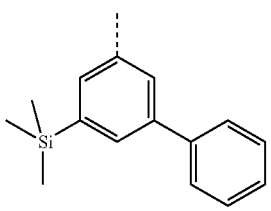
formula (81)
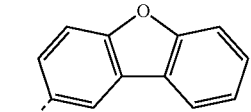
formula (82)
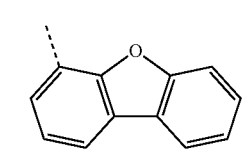
formula (83)
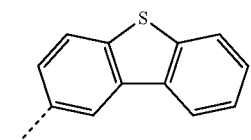
formula (84)
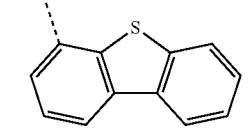
formula (85)
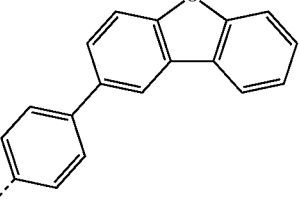
formula (86)
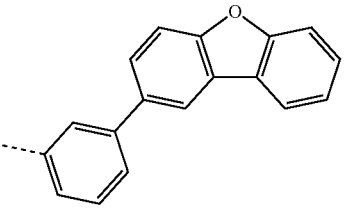

155
-continued
156
-continued
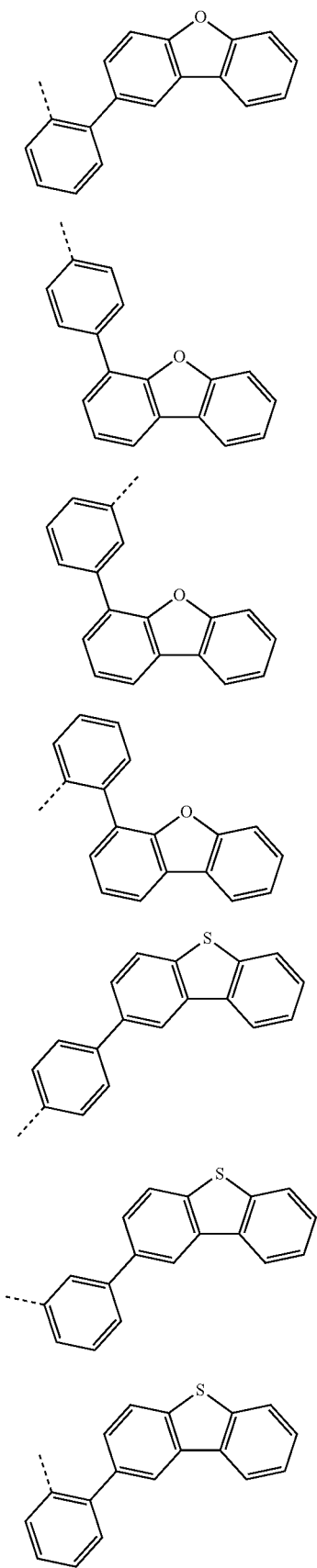
formula (87)
formula (88)
formula (89)
formula (90)
formula (91)
formula (92)
formula (93)
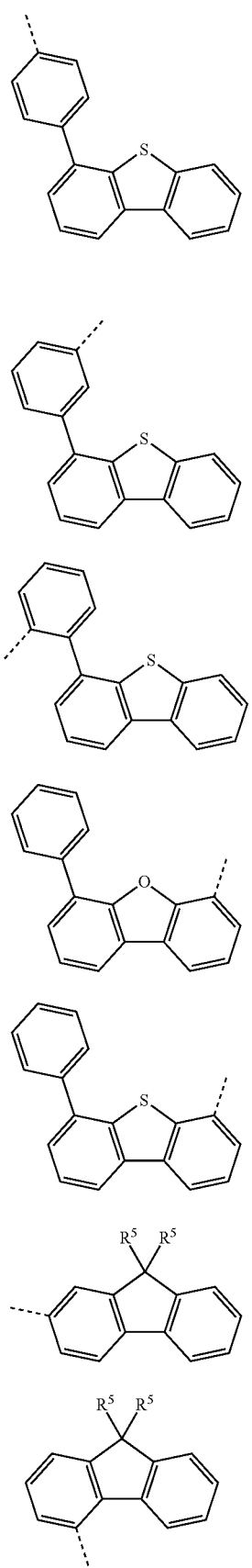
formula (94)
formula (95)
formula (96)
formula (97)
formula (98)
formula (99)
formula (100)

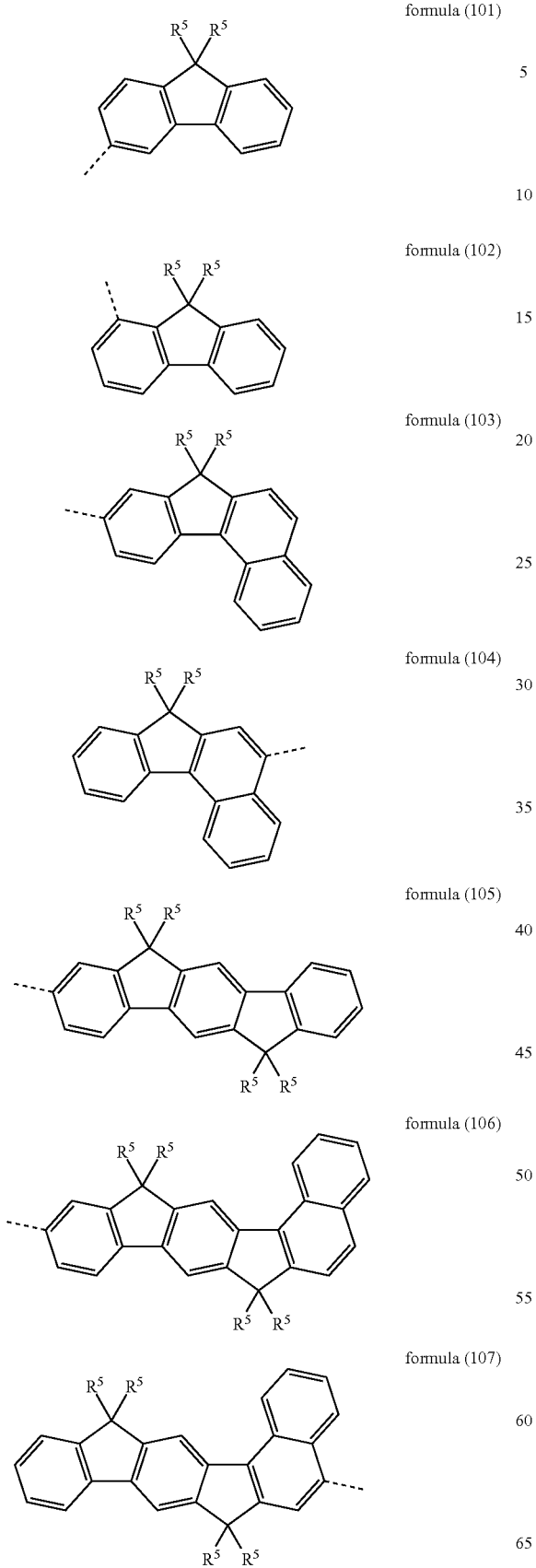
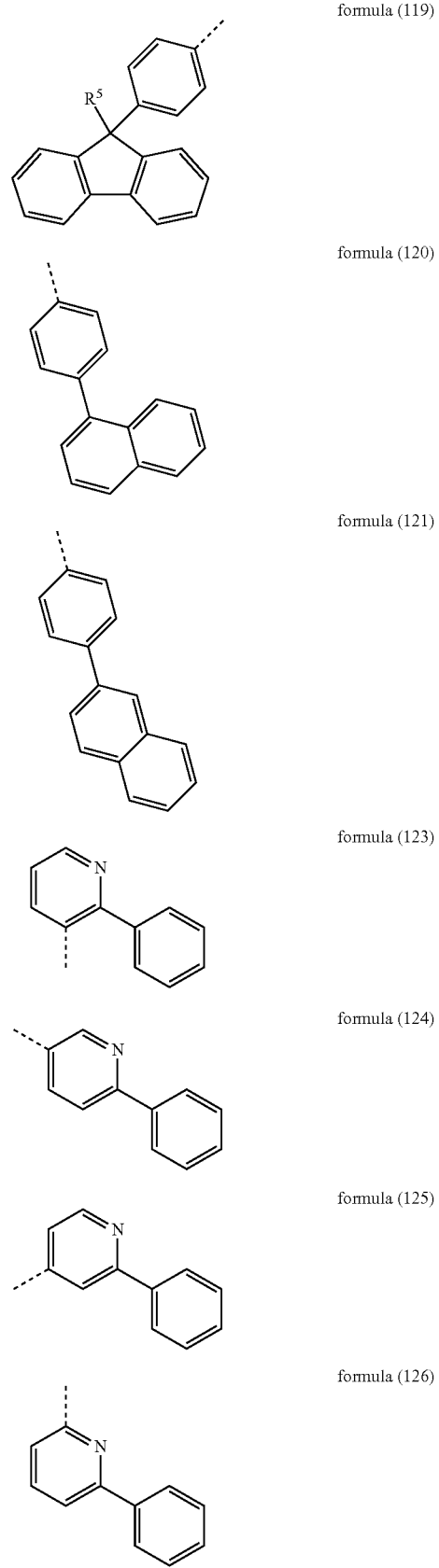

formula (127) 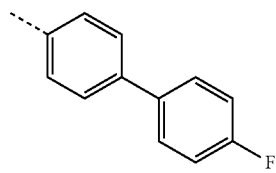

formula (128) 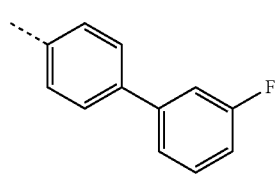

formula (129) 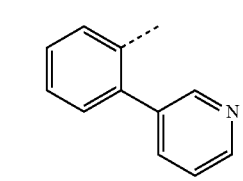

formula (130) 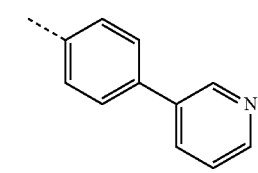

formula (131) 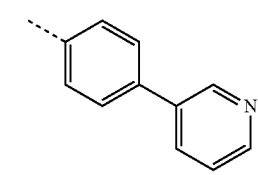

formula (132) 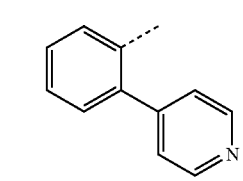

formula (133) 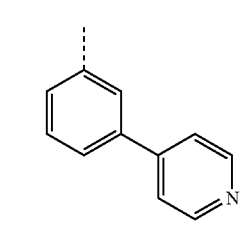

formula (134) 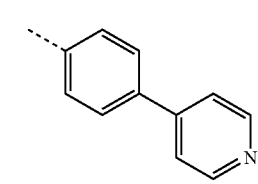

formula (135) 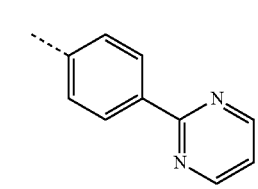

formula (136) 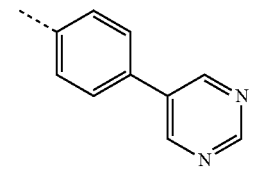

formula (137) 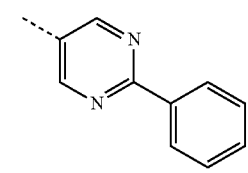

formula (138) 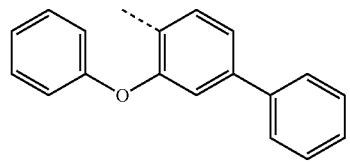

formula (139) 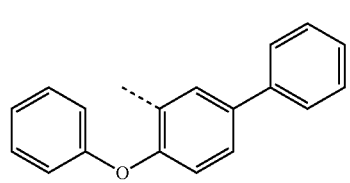

formula (140) 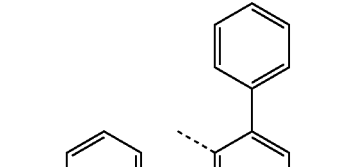

formula (141) 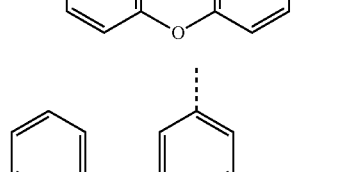

formula (142) 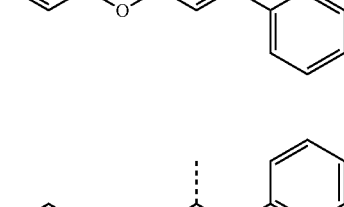

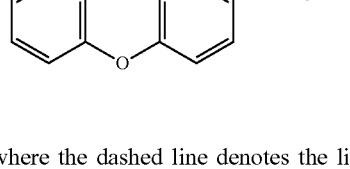

where the dashed line denotes the linking position to the nitrogen atom;

$R^2$, $R^4$, and $R^5$ are H, D, F, Cl, Br, I, C(=O)$R^6$, CN, Si($R^6$)$_3$, NO$_2$, N($R^6$)$_2$, P(=O)($R^6$)$_2$, S(=O)$R^6$, S(=O)$_2R^6$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals R⁶ and where one or more CH₂ groups in the above-mentioned groups is optionally replaced by —R⁶C═CR⁶—, —C≡C—, Si(R⁶)₂, C═O, C═S, C═NR⁶, —C(═O)O—, —C(═O)NR⁶—, P(═O)(R⁶), —O—, —S—, SO or SO₂ and where one or more H atoms in the above-mentioned groups is optionally replaced by D, F, Cl, Br, I, CN or NO₂, or an aromatic or heteroaromatic ring system having 6 to 30 aromatic ring atoms, which may in each case be substituted by one or more radicals R⁶, or an aryloxy group having 5 to 60 aromatic ring atoms, which is optionally substituted by one or more radicals R⁶, or an aralkyl group having 5 to 60 aromatic ring atoms, which may in each case be substituted by one or more radicals R⁶;

R¹
is H, D, F, Cl, Br, I, C(═O)R⁶, CN, Si(R⁶)₃, NO₂, N(R⁶)₂, P(═O)(R⁶)₂, S(═O)R⁶, S(═O)₂R⁶, a straight-chain alkoxy or thioalkyl group having 1 to 20 C atoms or a branched or cyclic alkoxy or thioalkyl group having 3 to 20 C atoms or an alkynyl group having 2 to 20 C atoms, where the above-mentioned groups may each be substituted by one or more radicals R⁶ and where one or more CH₂ groups in the above-mentioned groups is optionally replaced by —R⁶C═CR⁶, —C≡C—, Si(R⁶)₂, C═O, C═S, C═NR⁶, —C(═O)O—, —C(═O)NR⁶—, P(═O)(R⁶), —O—, —S—, SO or SO₂ and where one or more H atoms in the above-mentioned groups is optionally replaced by D, F, Cl, Br, I, CN or NO₂, or an aromatic or heteroaromatic ring system having 6 to 30 aromatic ring atoms, which may in each case be substituted by one or more radicals R⁶, or an aryloxy group having 5 to 60 aromatic ring atoms, which is optionally substituted by one or more radicals R⁶, or an aralkyl group having 5 to 60 aromatic ring atoms, which may in each case be substituted by one or more radicals R⁶, where the radicals R¹ and R² cannot be identical and the radicals R³ to R⁵ may on each occurrence be identical or different, but is optionally identical to either R¹ or to R²;

R³ is H;

R⁶
is on each occurrence, identically or differently, H, D, F, Br, I, C(═O)R⁷, CN, Si(R⁷)₃, NO₂, P(═O)(R⁷)₂, S(═O)R⁷, S(═O)₂R⁷, N(R⁷)₂, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals R⁷ and where one or more CH₂ groups in the above-mentioned groups is optionally replaced by —R⁷C═CR⁷—, —C≡C—, Si(R⁷)₂, C═O, C═S, C═NR⁷, —C(═O)O—, —C(═O)NR⁷—, P(═O)(R⁷), —O—, —S—, SO or SO₂ and where one or more H atoms in the above-mentioned groups is optionally replaced by D, F, Cl, Br, I, CN or NO₂, or an aromatic or heteroaromatic ring system having 5 to 30 aromatic ring atoms, which may in each case be substituted by one or more radicals R⁷, or an aryloxy or heteroaryloxy group having 5 to 30 aromatic ring atoms, which is optionally substituted by one or more radicals R⁷, where two or more adjacent substituents R⁶ may form a mono- or polycyclic ring system with one another;

R⁷
is selected from the group consisting of H, D, F, an aliphatic hydrocarbon radical having 1 to 20 C atoms or an aromatic or heteroaromatic ring system having 5 to 30 C atoms, in which one or more H atoms is optionally replaced by D or F, where two or more adjacent substituents R⁷ may form a mono- or polycyclic ring system with one another, and wherein the compound of formula (2) is a monoamine compound.

2. The device according to claim 1, wherein p=1 or r=1.

3. The device according to claim 1, wherein the compound has the general formula (3)

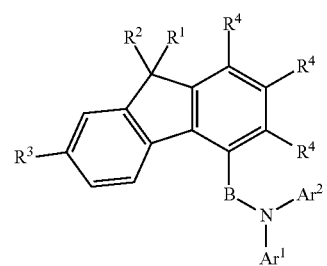

formula (3)

where the symbols and indices indicated are defined as indicated in claim 1.

4. The device according to claim 1, wherein the compound has the general formula (4)

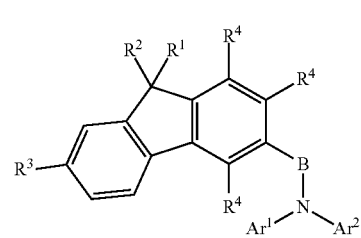

formula (4)

where the symbols and indices indicated are defined as indicated in claim 1.

5. The device according to claim 1, wherein the compound has the general formula (5)

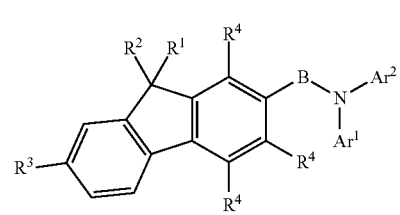

formula (5)

where the symbols and indices indicated are defined as indicated in claim 1.

6. The device according to claim 1, wherein the compound has the general formula (6)

formula (6)

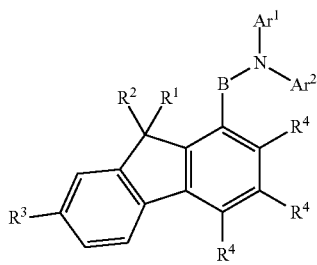

where the symbols and indices indicated are defined as indicated in claim 1.

7. The device according to claim 1, wherein B is a single bond or a phenylene, biphenylene, terphenylene, naphthylene, pyridinylene, pyrimidinylene, pyrazin-ylene, pyridazinylene, triazinylene, dibenzofuranylene, dibenzothiophenylene fluorenylene, or carbazoylene group, which is optionally substituted by one or more radicals $R^6$.

8. The device according to claim 1, wherein B is a single bond or a phenylene group, which is optionally substituted by one or more radicals $R^6$.

9. The device according to claim 1, wherein the device is an organic light-emitting transistor (OLETs), an organic field-quench device (OFQDs), an organic light-emitting electrochemical cells (OLECs, LECs or LEECs), an organic laser diode (O-laser) and an organic light-emitting diode (OLEDs).

10. The device according to claim 1, wherein the at least one compound of the formula (2)

formula (2)

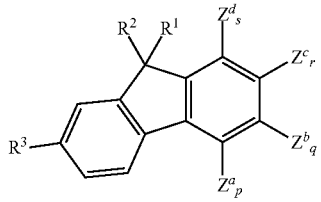

is employed with the following functions and in the following layers in the device:
  as hole-transport material in a hole-transport or hole-injection layer,
  as exciton-blocking material,
  as electron-blocking material,
  as matrix material in an emitting layer or
  as emitter in an emitting layer.

11. A compound of the general formula (2)

formula (2)

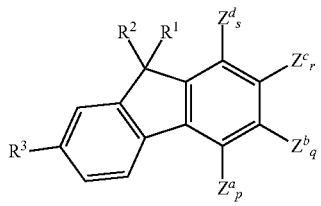

where the following applies to the symbols and indices used:

p, q, r, s
  are 0 or 1, where p+q+r+s=1;

$Z^a_0, Z^b_0, Z^c_0, Z^d_0$
  are, identically or differently on each occurrence, equal to $R^4$ $Z^a_1, Z^b_1, Z^c_1, Z^d_1$ are equal to

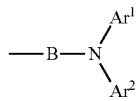

B
  is a single bond, a divalent aryl group having 6 to 30 ring atoms or a divalent heteroaryl group having 5 to 30 ring atoms, each of which is optionally substituted by one or more radicals $R^6$, where, if B is a single bond, the nitrogen atom is bonded directly to the fluorene;

$Ar^1$ and $Ar^2$ are selected, identically or differently on each occurrence, from the following groups of the formulae (42) to (107) (119)-(121) and (123)-(142)

formula (42)

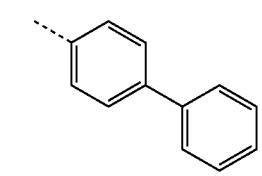

formula (43)

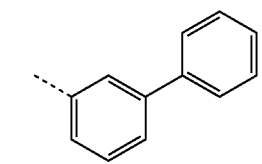

formula (44)

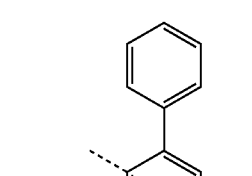

formula (45)

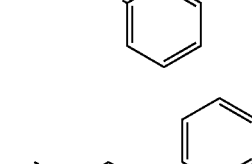

formula (46)

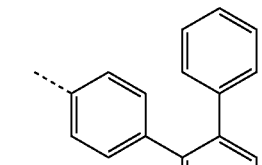

formula (47)
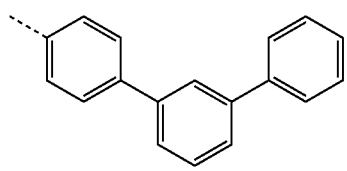
formula (48)
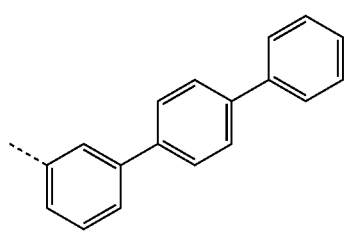
formula (49)
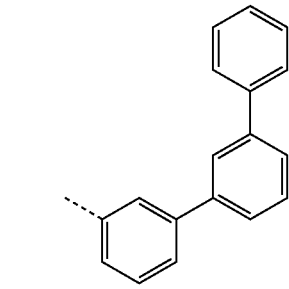
formula (50)
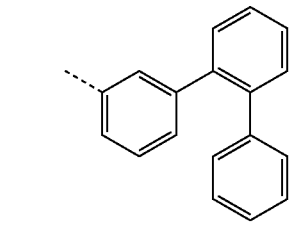
formula (51)
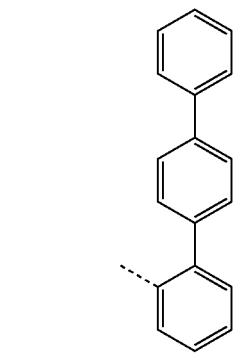
formula (52)
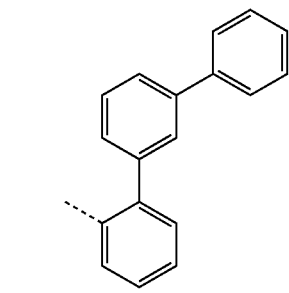
formula (53)
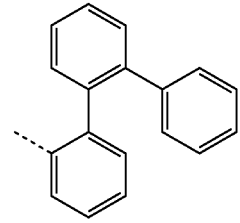
formula (54)
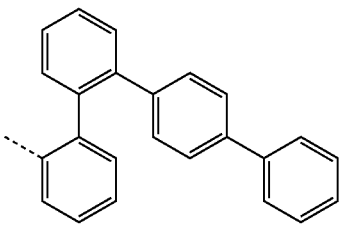
formula (55)
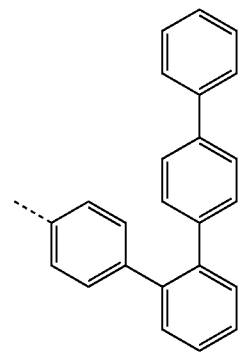
formula (56)
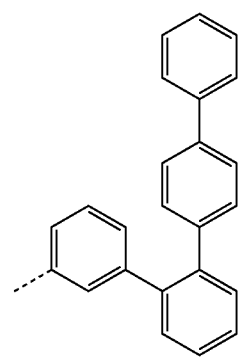
formula (57)
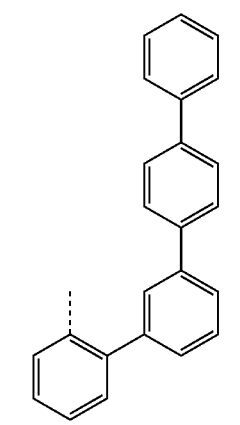

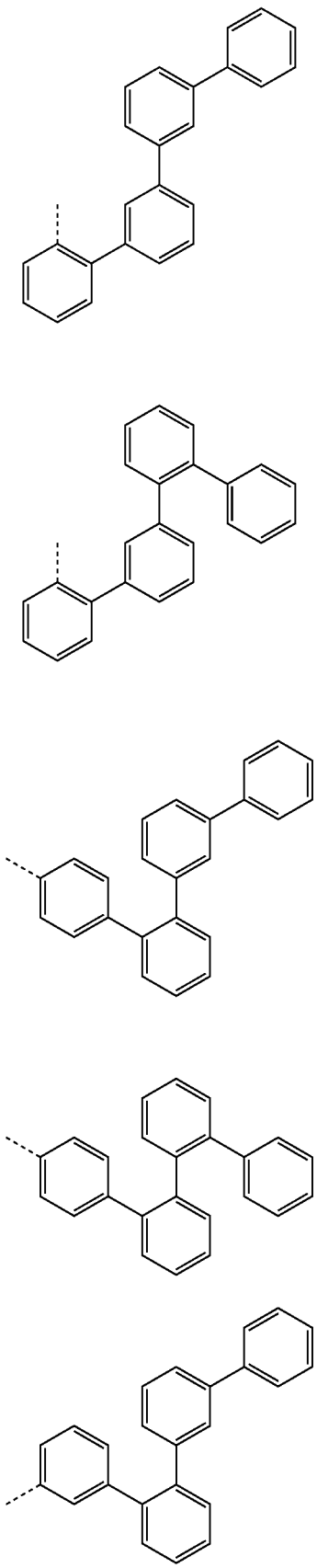
formula (58)
formula (59)
formula (60)
formula (61)
formula (62)
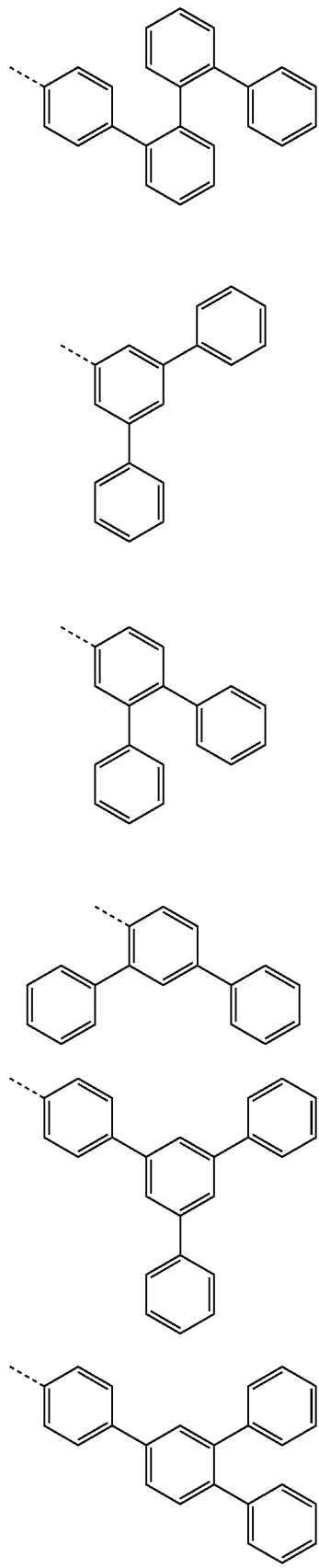
formula (63)
formula (64)
formula (65)
formula (66)
formula (67)
formula (68)

formula (69)
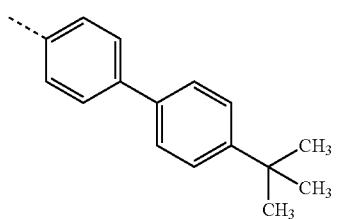
formula (70)
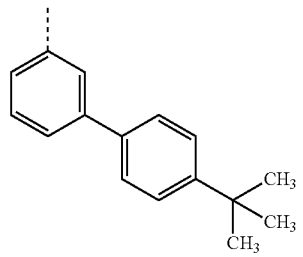
formula (71)
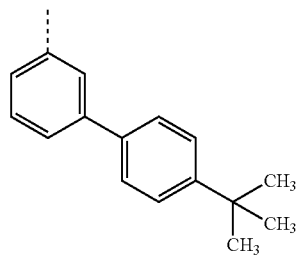
formula (72)
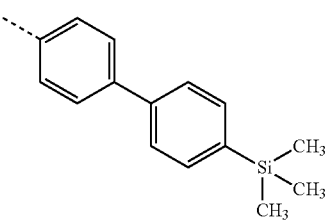
formula (73)
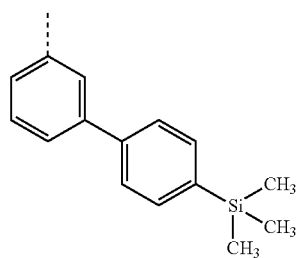
formula (74)
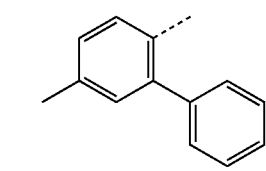
formula (75)
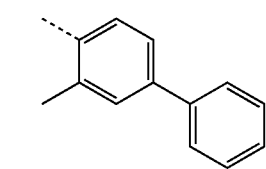
formula (76)
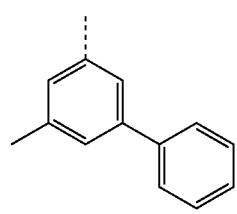
formula (77)
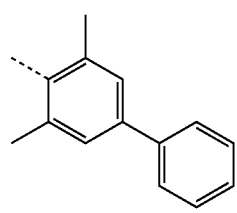
formula (78)
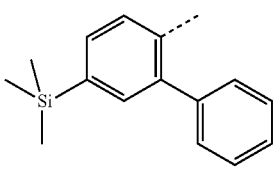
formula (79)
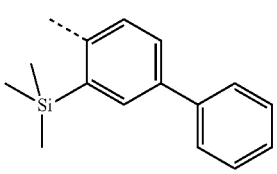
formula (80)
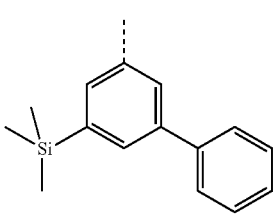
formula (81)
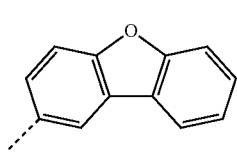
formula (82)
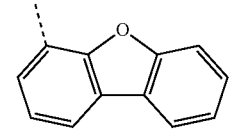
formula (83)
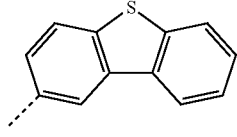
formula (84)
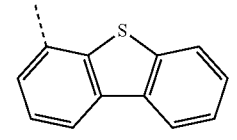

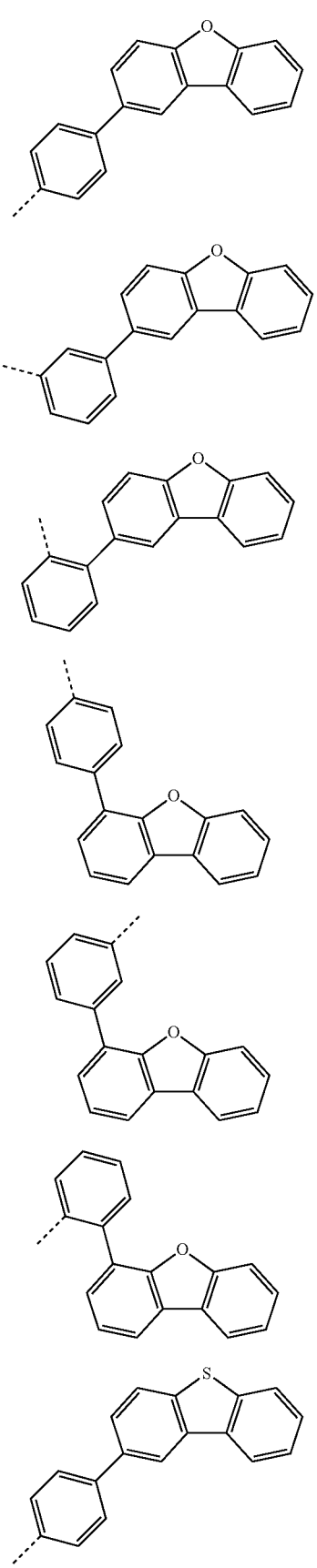
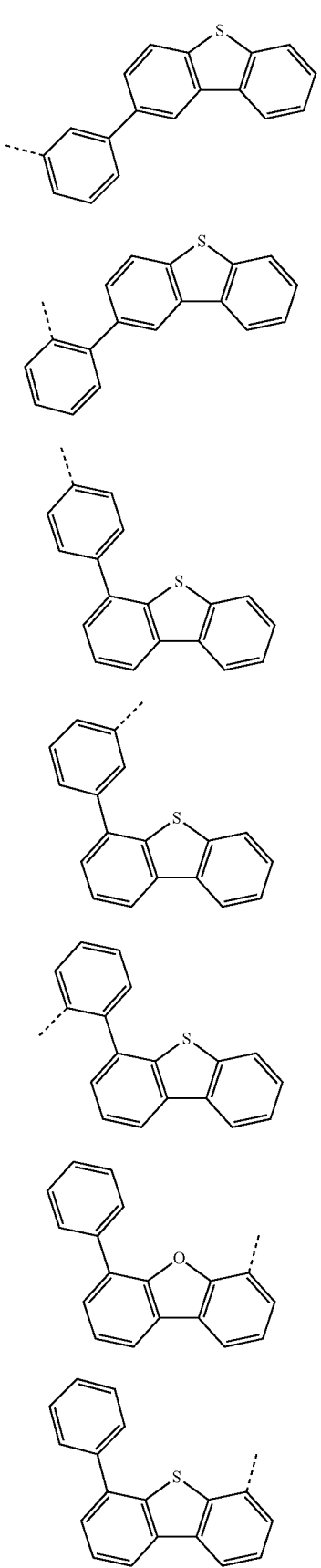

formula (99)
formula (100)
formula (101)
formula (102)
formula (103)
formula (104)
formula (105)
formula (106)
formula (107)
formula (119)
formula (120)
formula (121)
formula (123)
formula (124)
formula (125)

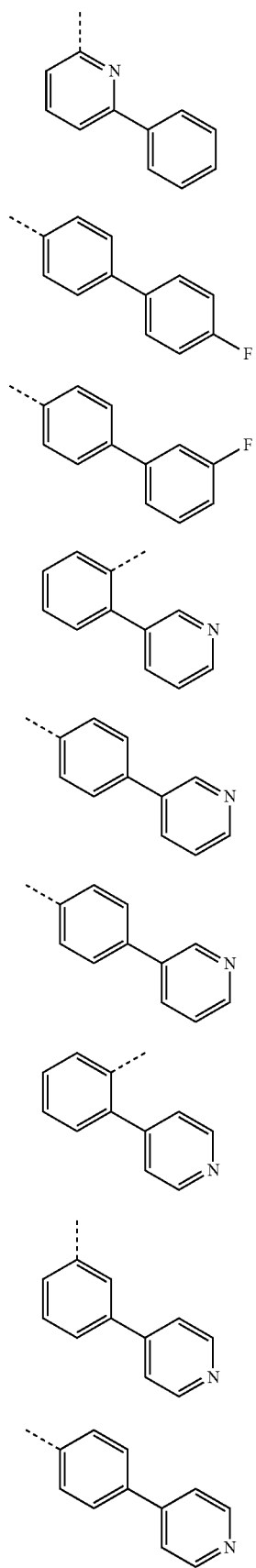
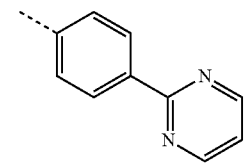
formula (135)
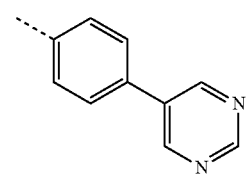
formula (136)
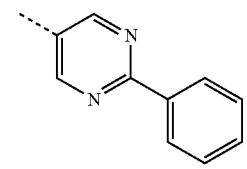
formula (137)
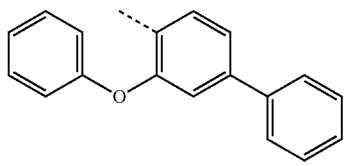
formula (138)
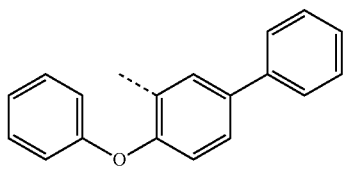
formula (139)
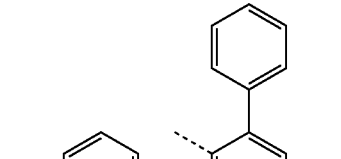
formula (140)
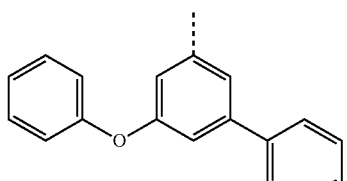
formula (141)
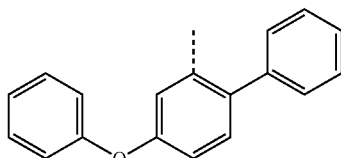
formula (142)
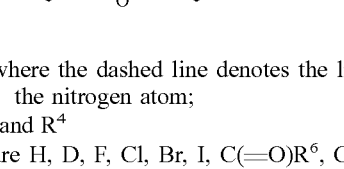
where the dashed line denotes the linking position to the nitrogen atom;
$R^2$ and $R^4$
are H, D, F, Cl, Br, I, C(=O)$R^6$, CN, Si($R^6$)$_3$, NO$_2$, N($R^6$)$_2$, P(=O)($R^6$)$_2$, S(=O)$R^6$, S(=O)$_2R^6$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals $R^6$ and where one or more $CH_2$ groups in the above-mentioned groups is optionally replaced by $-R^6C=CR^6-$, $-C\equiv C-$, $Si(R^6)_2$, $C=O$, $C=S$, $C=NR^6$, $-C(=O)O-$, $-C(=O)NR^6-$, $P(=O)(R^6)$, $-O-$, $-S-$, $SO$ or $SO_2$ and where one or more H atoms in the above-mentioned groups is optionally replaced by D, F, Cl, Br, I, CN or $NO_2$, or an aromatic or heteroaromatic ring system having 6 to 30 aromatic ring atoms, which may in each case be substituted by one or more radicals $R^6$, or an aryloxy group having 5 to 60 aromatic ring atoms, which is optionally substituted by one or more radicals $R^6$, or an aralkyl group having 5 to 60 aromatic ring atoms, which may in each case be substituted by one or more radicals $R^6$, and where at least one of the radicals from $R^1$ and $R^2$ represents an aromatic or heteroaromatic ring system having 6 to 30 aromatic ring atoms, which may in each case be substituted by one or more radicals $R^6$;

$R^1$ is H, D, F, Cl, Br, I, $C(=O)R^6$, CN, $Si(R^6)_3$, $NO_2$, $N(R^6)_2$, $P(=O)(R^6)_2$, $S(=O)R^6$, $S(=O)_2R^6$, a straight-chain alkoxy or thioalkyl group having 1 to 20 C atoms or a branched or cyclic alkoxy or thioalkyl group having 3 to 20 C atoms or an alkynyl group having 2 to 20 C atoms, where the above-mentioned groups may each be substituted by one or more radicals $R^6$ and where one or more $CH_2$ groups in the above-mentioned groups is optionally replaced by $-R^6C=CR^6-$, $-C\equiv C-$, $Si(R^6)_2$, $C=O$, $C=S$, $C=NR^6$, $-C(=O)O-$, $-C(=O)NR^6-$, $P(=O)(R^6)$, $-O-$, $-S-$, $SO$ or $SO_2$ and where one or more H atoms in the above—mentioned groups is optionally replaced by D, F, Cl, Br, I, CN or $NO_2$, or an aromatic or heteroaromatic ring system having 6 to 30 aromatic ring atoms, which may in each case be substituted by one or more radicals $R^6$, or an aryloxy group having 5 to 60 aromatic ring atoms, which is optionally substituted by one or more radicals $R^6$, or an aralkyl group having 5 to 60 aromatic ring atoms, which may in each case be substituted by one or more radicals $R^6$, where the radicals $R^1$ and $R^2$ cannot be identical and the radicals $R^3$ to $R^5$ may on each occurrence be identical or different, but is optionally identical to either $R^1$ or to $R^2$;

$R^3$ is H;

$R^5$ is H, D, $C(=O)R^6$, CN, $Si(R^6)_3$, $NO_2$, $N(R^6)_2$, $P(=O)(R^6)_2$, $S(=O)R^6$, $S(=O)_2R^6$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals $R^6$ and where one or more $CH_2$ groups in the above-mentioned groups is optionally replaced by $-R^6C=CR^6-$, $-C\equiv C-$, $Si(R^6)_2$, $C=O$, $C=S$, $C=NR^6$, $-C(=O)O-$, $-C(=O)NR^6-$, $P(=O)(R^6)$, $-O-$, $-S-$, $SO$ or $SO_2$ and where one or more H atoms in the above-mentioned groups is optionally replaced by D, F, Cl, Br, I, CN or $NO_2$, or an aromatic or heteroaromatic ring system having 6 to 30 aromatic ring atoms, which may in each case be substituted by one or more radicals $R^6$, or an aryloxy group having 5 to 60 aromatic ring atoms, which is optionally substituted by one or more radicals $R^6$, or an aralkyl group having 5 to 60 aromatic ring atoms, which may in each case be substituted by one or more radicals $R^6$, $R^6$ is on each occurrence, identically or differently, H, D, F, Br, I, $C(=O)R^7$, CN, $Si(R^7)_3$, $NO_2$, $P(=O)(R^7)_2$, $S(=O)R^7$, $S(=O)_2R^7$, $N(R^7)_2$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals $R^7$ and where one or more $CH_2$ groups in the above-mentioned groups is optionally replaced by $-R^7C=CR^7-$, $-C\equiv C-$, $Si(R^7)_2$, $C=O$, $C=S$, $C=NR^7$, $-C(=O)O-$, $-C(=O)NR^7-$, $P(=O)(R^7)$, $-O-$, $-S-$, $SO$ or $SO_2$ and where one or more H atoms in the above-mentioned groups is optionally replaced by D, F, Cl, Br, I, CN or $NO_2$, or an aromatic or heteroaromatic ring system having 5 to 30 aromatic ring atoms, which may in each case be substituted by one or more radicals $R^7$, or an aryloxy or heteroaryloxy group having 5 to 30 aromatic ring atoms, which is optionally substituted by one or more radicals $R^7$, where two or more adjacent substituents $R^6$ may form a mono- or polycyclic ring system with one another;

$R^7$ is selected from the group consisting of H, D, F, an aliphatic hydrocarbon radical having 1 to 20 C atoms or an aromatic or heteroaromatic ring system having 5 to 30 C atoms, in which one or more H atoms is optionally replaced by D or F, where two or more adjacent substituents $R^7$ may form a mono—or polycyclic ring system with one another; and wherein the compound of formula (2) is a monoamine compound.

12. A process for the preparation of the compound according to claim 11 by means of Buchwald coupling.

13. An electronic device which comprises the compound according to claim 11.

14. An electronic device comprising at least one compound according to claim 11, wherein the electronic device is selected from the group consisting of organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), and organic laser diodes O-lasers).

* * * * *